United States Patent
Liu et al.

(10) Patent No.: US 9,695,246 B2
(45) Date of Patent: Jul. 4, 2017

(54) ANTI-OX40 ANTIBODIES AND METHODS OF USING THE SAME

(71) Applicant: Board of Regents, The University of Texas System, Austin, TX (US)

(72) Inventors: Yong-Jun Liu, Pearland, TX (US); Kui Shin Voo, Pearland, TX (US); Laura Bover, Pearland, TX (US); Naoya Tsurushita, Palo Alto, CA (US); J. Yun Tso, Menlo Park, CA (US); Shankar Kumar, Pleasanton, CA (US)

(73) Assignee: Board of Regents, The University of Texas System, Austin, TX (US)

( * ) Notice: Subject to any disclaimer, the term of this patent is extended or adjusted under 35 U.S.C. 154(b) by 261 days.

(21) Appl. No.: 14/684,550

(22) Filed: Apr. 13, 2015

(65) Prior Publication Data

US 2015/0315281 A1 Nov. 5, 2015

Related U.S. Application Data

(62) Division of application No. 13/818,645, filed as application No. PCT/US2011/048752 on Aug. 23, 2011, now Pat. No. 9,006,399.

(60) Provisional application No. 61/375,999, filed on Aug. 23, 2010, provisional application No. 61/380,827, filed on Sep. 8, 2010.

(51) Int. Cl.
*C07K 16/28* (2006.01)
*A61K 39/395* (2006.01)
*A61K 39/00* (2006.01)

(52) U.S. Cl.
CPC .... *C07K 16/2878* (2013.01); *A61K 2039/505* (2013.01); *C07K 2317/24* (2013.01); *C07K 2317/56* (2013.01); *C07K 2317/565* (2013.01); *C07K 2317/74* (2013.01); *C07K 2317/75* (2013.01)

(58) Field of Classification Search
None
See application file for complete search history.

(56) References Cited

U.S. PATENT DOCUMENTS

| | | | |
|---|---|---|---|
| 6,312,700 B1 | 11/2001 | Weinberg | |
| 7,235,555 B2 | 6/2007 | Evenou et al. | |
| 7,358,253 B2 | 4/2008 | Evenou et al. | |
| 7,504,101 B2 | 3/2009 | Weinberg | |
| 7,534,808 B2 | 5/2009 | Evenou et al. | |
| 7,550,140 B2 | 6/2009 | Bakker et al. | |
| 7,622,444 B2 | 11/2009 | Weinberg | |
| 7,741,077 B2 | 6/2010 | Grawunder et al. | |
| 7,754,209 B2 | 7/2010 | Ledbetter et al. | |
| 7,758,852 B2 | 7/2010 | Soto-Jara et al. | |
| 7,858,765 B2 | 12/2010 | Soto-Jara et al. | |
| 7,960,515 B2 | 6/2011 | Min et al. | |
| 9,006,399 B2 * | 4/2015 | Liu | C07K 16/2878 424/154.1 |
| 9,163,085 B2 * | 10/2015 | Liu | C07K 16/2878 |
| 9,527,917 B2 * | 12/2016 | Liu | C07K 16/2878 |
| 2002/0004041 A1 | 1/2002 | Albert et al. | |
| 2003/0235584 A1 | 12/2003 | Kloetzer et al. | |
| 2006/0281072 A1 | 12/2006 | Bakker | |
| 2007/0190599 A1 | 8/2007 | Nakano et al. | |
| 2008/0260748 A1 | 10/2008 | Iwamoto et al. | |
| 2008/0286286 A1 | 11/2008 | Liu | |
| 2009/0214560 A1 | 8/2009 | Min et al. | |
| 2010/0136030 A1 | 6/2010 | Salah-Eddine et al. | |
| 2010/0136628 A1 | 6/2010 | Soto-Jara et al. | |
| 2010/0166740 A1 | 7/2010 | Endl et al. | |
| 2010/0196359 A1 | 8/2010 | Kato et al. | |
| 2010/0254978 A1 | 10/2010 | Lawson et al. | |
| 2011/0008368 A1 | 1/2011 | Liu et al. | |
| 2014/0308276 A1 | 10/2014 | Liu et al. | |

FOREIGN PATENT DOCUMENTS

| | | |
|---|---|---|
| CL | 2008-578 | 10/2008 |
| CL | 2011-1994 | 8/2011 |
| CL | 2014-631 | 9/2014 |
| CL | 2014-1193 | 12/2014 |
| EP | 1060247 | 12/2000 |
| EP | 1321477 | 6/2003 |
| EP | 1490355 | 12/2004 |
| EP | 1525223 | 4/2005 |
| WO | WO 99-42585 | 8/1999 |

(Continued)

OTHER PUBLICATIONS

"GSK-3174998," Pharmaprojects, Citeline Inc., latest change date Feb. 25, 2016.
"GSK-3174998," Thomson Reuters Cortellis, created Jun. 15, 2016.
"OX-40 antibody, GlaxoSmithKline," Pharmaprojects, Citeline Inc., last change date Dec. 9, 2013.
Bi et al., "In vivo characterization of ipilimumab T cell modulation and antitumor activity in a tumor bearing humanized NSG mouse model," Abstract A054, CRI-CIMT-EATI-AACR Inaugural International Cancer Immunotherapy Conference: Translating Science into Survival, New York, NY, 2015.

(Continued)

*Primary Examiner* — Ilia Ouspenski
(74) *Attorney, Agent, or Firm* — Parker Highlander PLLC

(57) ABSTRACT

Human antibodies, preferably recombinant human antibodies, both humanized and chimeric, which specifically bind to human OX40 are disclosed. Preferred antibodies have high affinity for OX40 receptor and activate the receptor in vitro and in vivo. The antibody can be a full-length antibody or an antigen-binding portion thereof. The antibodies, or antibody portions, are useful for modulating receptor activity, e.g., in a human subject suffering from a disorder in which OX40 activity is detrimental. Nucleic acids, vectors and host cells for expressing the recombinant human antibodies are provided, and methods of synthesizing the recombinant human antibodies, are also provided.

9 Claims, 50 Drawing Sheets

(56) References Cited

FOREIGN PATENT DOCUMENTS

| WO | WO 2002/065093 | 8/2002 |
|---|---|---|
| WO | WO 03-068819 | 8/2003 |
| WO | WO 03-082859 | 10/2003 |
| WO | WO 03-082919 | 10/2003 |
| WO | WO 03-106498 | 12/2003 |
| WO | WO 2004-037321 | 5/2004 |
| WO | WO 2005-013958 | 2/2005 |
| WO | WO 2005-017148 | 2/2005 |
| WO | WO 2006-041763 | 4/2006 |
| WO | WO 2006/059110 | 6/2006 |
| WO | WO 2006-063067 | 6/2006 |
| WO | WO 2007-062245 | 5/2007 |
| WO | WO 2007/062445 | 6/2007 |
| WO | WO 2007-084559 | 7/2007 |
| WO | WO 2008-036374 | 3/2008 |
| WO | WO 2008-051424 | 5/2008 |
| WO | WO 2008/106116 | 9/2008 |
| WO | WO 2008/149143 | 12/2008 |
| WO | WO 2009-079335 | 6/2009 |
| WO | WO 2010/096418 | 8/2010 |
| WO | WO 2011-071871 | 6/2011 |
| WO | WO 2013/038191 | 3/2013 |
| WO | WO 2013/068563 | 5/2013 |
| WO | WO 2014/140180 | 9/2014 |
| WO | WO 2016/059602 | 4/2016 |

OTHER PUBLICATIONS

Infante et al., "Engage-1: A first in human study of the OX40 agonist GSK3174998 alone and in combination with pembrolizumab in patients with advanced solid tumors," Abstract TPS3107, Annual Meeting of the American Society of Clinical Oncology (ASCO), Chicago, IL, 2016.
Liu et al., "Effects of BRAF and MEK inhibitors, dabrafenib and trametinib, on the immune system and in combination with immunomodulatory antibodies targeting PD1, PD-L1 and CTLA-4," Abstract 5031, 105th Annual Meeting of the American Association for Cancer Research (AACR), San Diego, CA, 2014.
Liu et al., "The BRAF and MEK inhibitors dabrafenib and trametinib: Effects on immune function and in combination with immunomodulatory antibodies targeting PD-1, PD-L1, and CTLA-4," *Clinical Cancer Research*, 21(7):1639-1651, 2015.
Phillips et al., "Cell-specific expression of B lymphocyte (April, BLyS)- and Th2 (CD30L/CD153)—promoting tumor necrosis factor superfamily ligands in human placentas," *Journal of Leukocyte Biology*, 74(1):81-87, 2003.
Sica et al., "RELT, a new member of the tumor necrosis factor receptor superfamily, is selectively expressed in hematopoietic tissues and activates transcription factor NF-κB," *Blood*, 97(9):2702-2707, 2001.
Stables et al., "Transcriptomic analyses of murine resolution-phase macrophages," *Blood*, 118(26):e192-e208, 2011.
Tian et al., "The effect of blocking CD28 and CD134 co-stimulatory pathways in rat cardiac transplant," 9th Basic Science Symposium of the International Transplantation Society, La Baule, France, 2005.
Toniatti et al. "Engaging the immune system with GSK3174998, a potent anti-OX40 agonist antibody," Abstract 4864, 107th Annual Meeting of the American Association for Cancer Research (AACR), New Orleans, LA, 2016.
"Anti-Mouse CD134 (OX40) PE, Clone, OX-86," Affymetrix, e-Bioscience, downloaded at http://www.ebioscience.com/mouse-cd134-antibody-pe-ox-86.htm, downloaded 2015.
Office Action issued in Chilean Application No. 545-2013, mailed May 22, 2015.
Ruby and Weinberg, "The effect of aging on OX40 agonist-mediated cancer immunotherapy," *Cancer Immunol. Immunother.*, 58:1941-1947, 2009.
Summons to Attend Oral Proceedings issued in European Application No. 11820495.7, mailed Dec. 11, 2015.

Janeway et al., "The interaction of the antibody molecule with specific antigen," *Immunobiology: The Immune System in Health and Disease*, 5th Edition, New York: Garland Science, 2001.
Database GenBank AAO23242.1, immunoglobulin heavy chain variable region, partial [Mus musculus], 2003.
Database GenBank ABY66176.1, immunoglobulin E monoclonal antibody 63E8 light chain variable region, partial [Mus musculus], 2008.
Redmond and Weinberg, "Targeting OX40 and OX40L for the treatment of autoimmunity and cancer," *Critical Reviews in Immunology*, 27(5):415-436, 2007. (Abstract only).
Search Report issued in Eurasian Application No. 201500204, issued Sep. 2, 2015.
Extended European Search Report issued in European Application No. 11820495.7, mailed Feb. 18, 2014.
Extended European Search Report issued in European Application No. 12825007.3, mailed May 20, 2015.
Gough et al., "OX40 agonist therapy enhances CD8 infiltration and decreases immune suppression in the tumor," *Cancer Research*, 68(13):5206-5215, 2008.
Lepisto et al., "Expression and function of the OX40/OX40L costimulatory pair during herpes stromal keratits," *Journal of Leukocyte Biology*, 81:766-774, 2007.
Office Action issued in Australian Application No. 2011293558, mailed Oct. 10, 2013.
Office Action issued in Australian Application No. 2012299421, mailed Mar. 16, 2015.
Office Action issued in Chinese Application No. 20118051223.5, mailed Mar. 23, 2015, and English language translation thereof.
Office Action issued in Chinese Application No. 201180051223.5, mailed Jul. 11, 2014, and English language translation thereof.
Office Action issued in Colombian Application No. 13-044.004, mailed Feb. 20, 2014.
Office Action issued in Colombian Application No. 13-440004, mailed Jan. 19, 2015.
Office Action issued in Eurasian Application No. 201390278/28, mailed Oct. 29, 2014, and English language translation thereof.
Office Action issued in European Application No. 11820495.7, mailed Sep. 25, 2014.
Office Action issued in European Application No. 11820495.7, mailed Apr. 23, 2015.
Office Action issued in New Zealand Application No. 608033, mailed Jul. 26, 2013.
Office Action issued in New Zealand Application No. 608033, mailed Jul. 2, 2014.
Office Action issued in Russian Application No. 2014110955, mailed Dec. 24, 2014, and English language translation thereof.
Office Action issued in U.S. Appl. No. 13/818,645, mailed May 14, 2014.
Office Action issued in U.S. Appl. No. 14/240,535, mailed Dec. 3, 2014.
Office Action issued in U.S. Appl. No. 14/240,535, mailed Feb. 24, 2015.
PCT International Preliminary Report on Patentability issued in International Application No. PCT/US2012/024570, mailed Mar. 6, 2014.
PCT International Preliminary Report on Patentability issued in International Application No. PCT/US2011/048752, mailed Feb. 26, 2013.
PCT International Search Report issued in International Application No. PCT/US2012/024570, mailed Sep. 24, 2012.
PCT International Search Report issued in International Application No. PCT/US2011/048752, mailed Mar. 22, 2012.
Piconese et al., "OX40 triggering blocks suppression by regulatory T cells and facilitates tumor rejection," *The Journal of Experimental Medicine*, 205(4):825-839, 2008.
Weinberg et al., "Anti-OX40 (CD134) administration to nonhuman primates: immunostimulatory effects and toxicokinetic study," *J Immunother.*, 29(6):575-585, 2006.
Weinberg et al., "Science gone translational: the OX40 agonist story," *Immunological Reviews*, 244:218-231, 2011.

(56) References Cited

OTHER PUBLICATIONS

Xiao et al., "OX40/OX40L costimulation affects induction of Foxp3+ regulatory T cells in part by expanding memory T cells in vivo," *The Journal of Immunology*, 181(5):3193-3201, 2008.
Office Action issued in United Arab Emirates Application No. P1942013, mailed May 1, 2017.

* cited by examiner

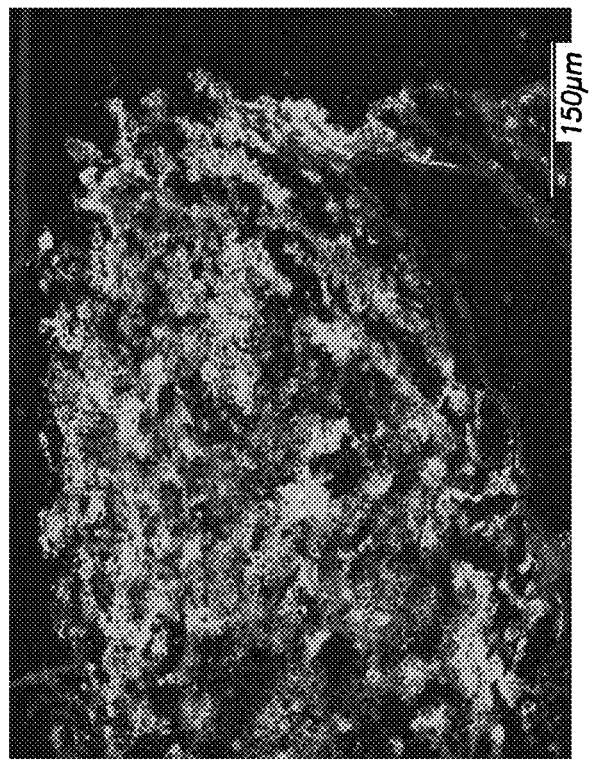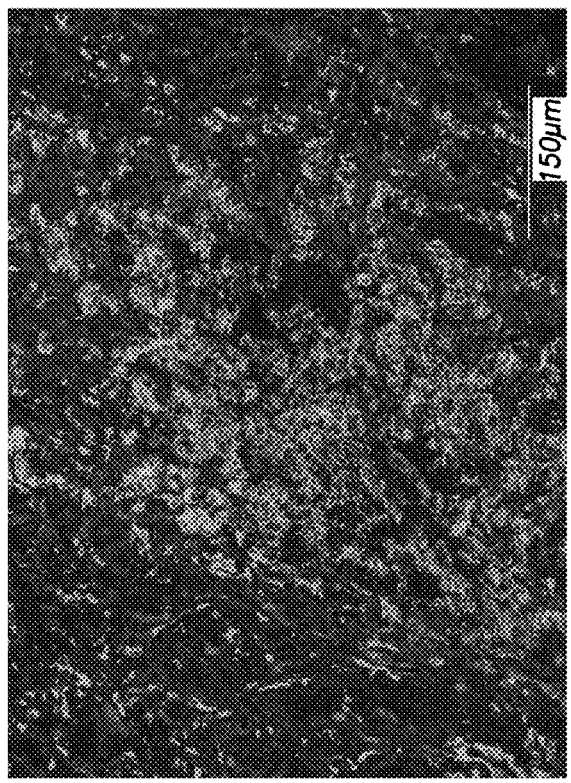
FIG. 1

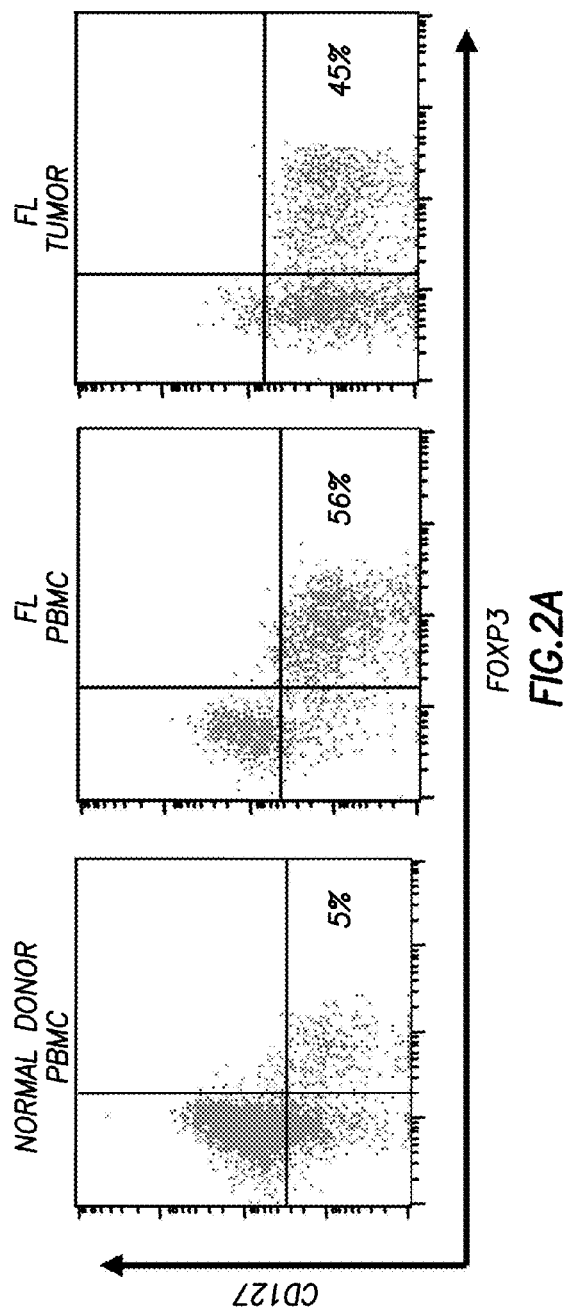
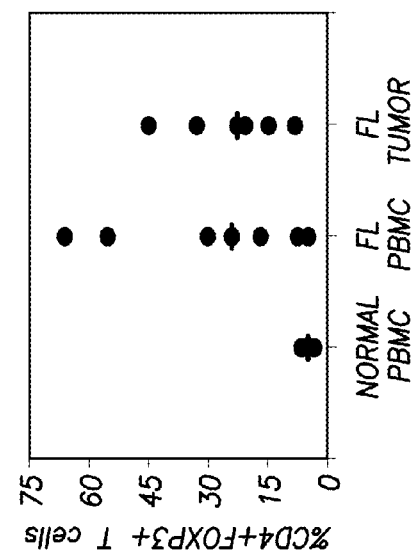
FIG.2A
FIG.2B

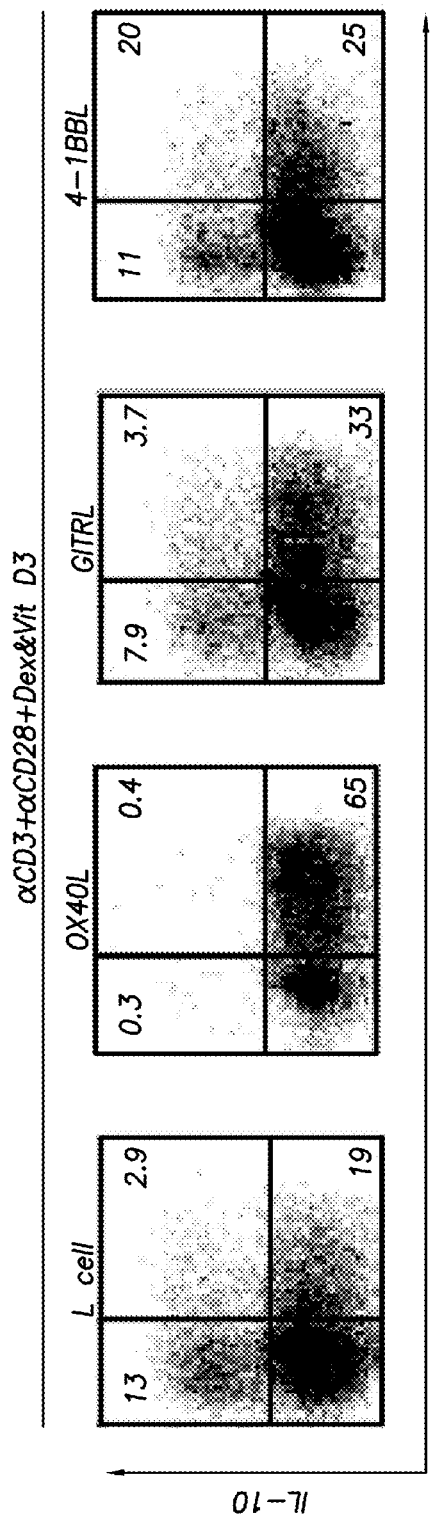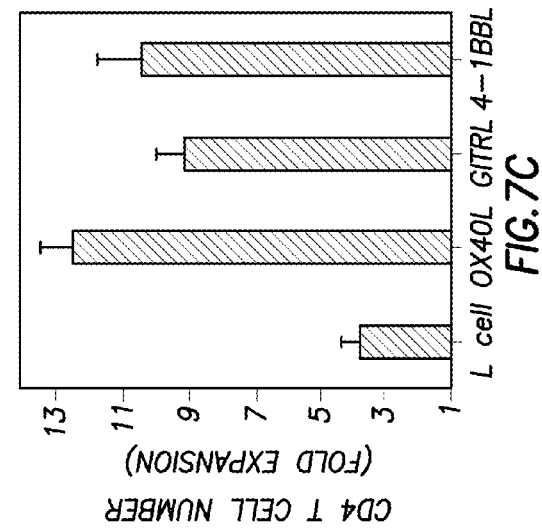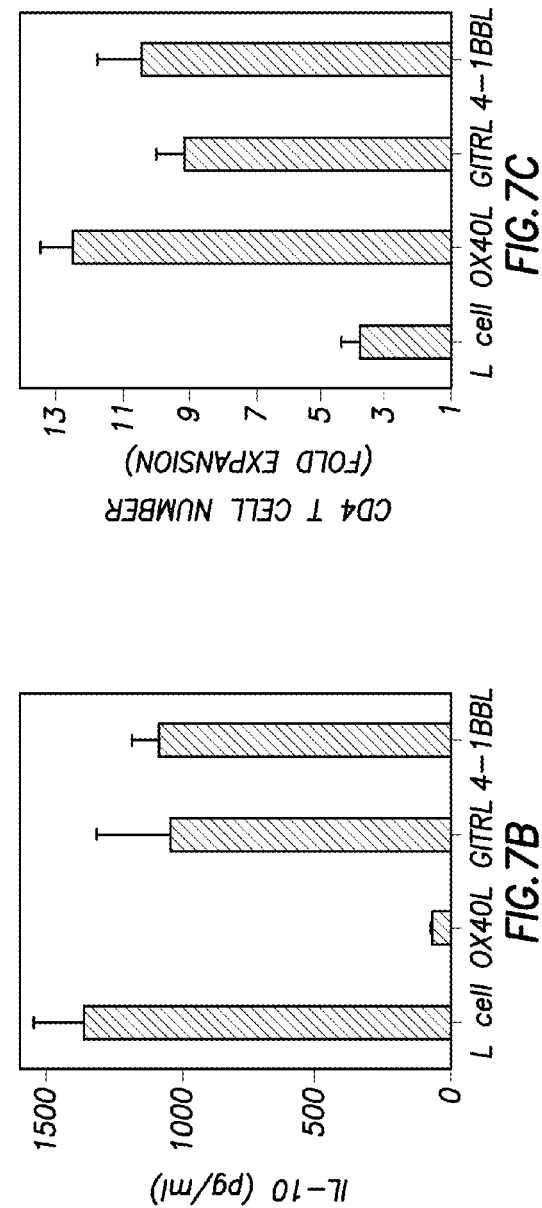

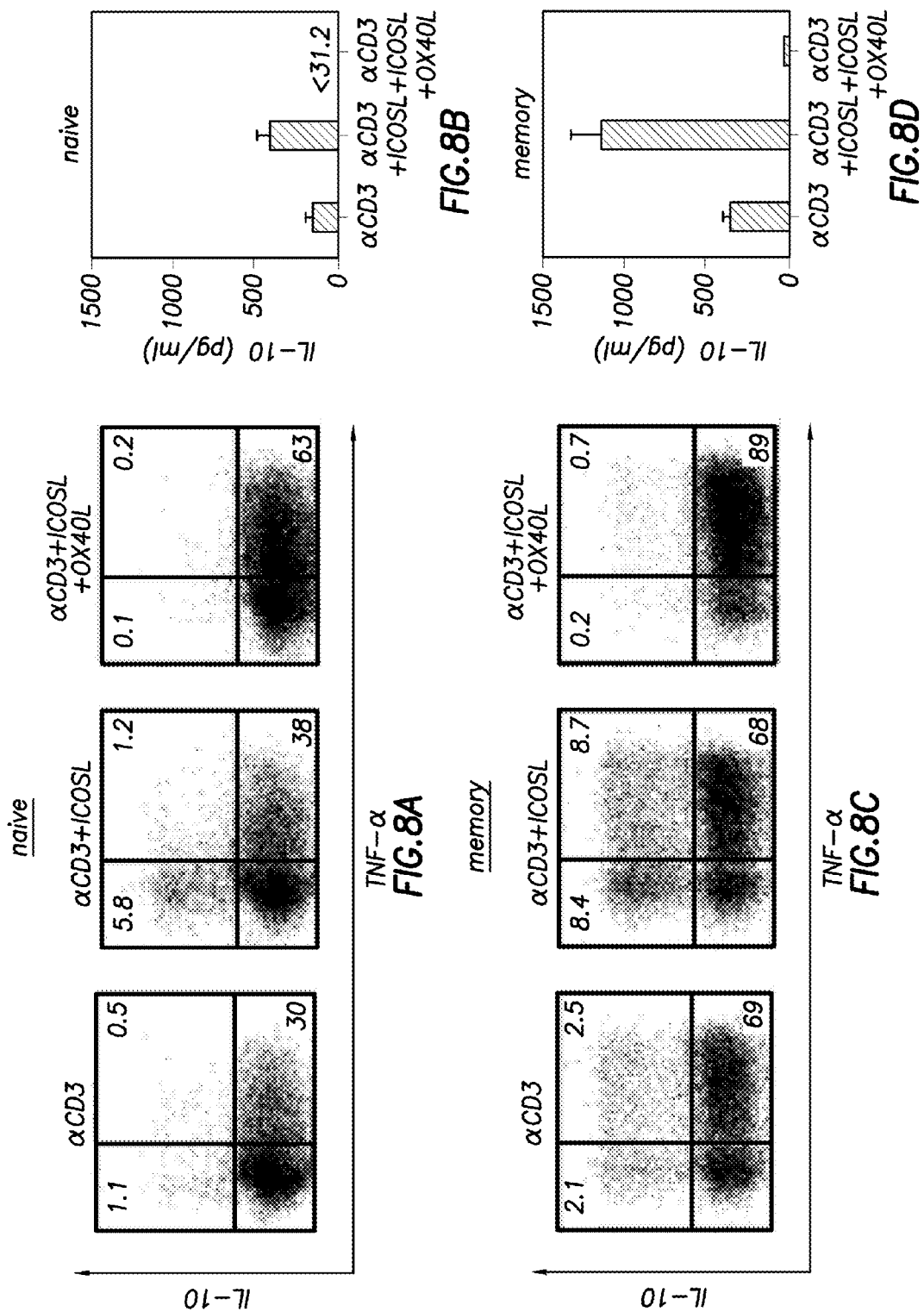

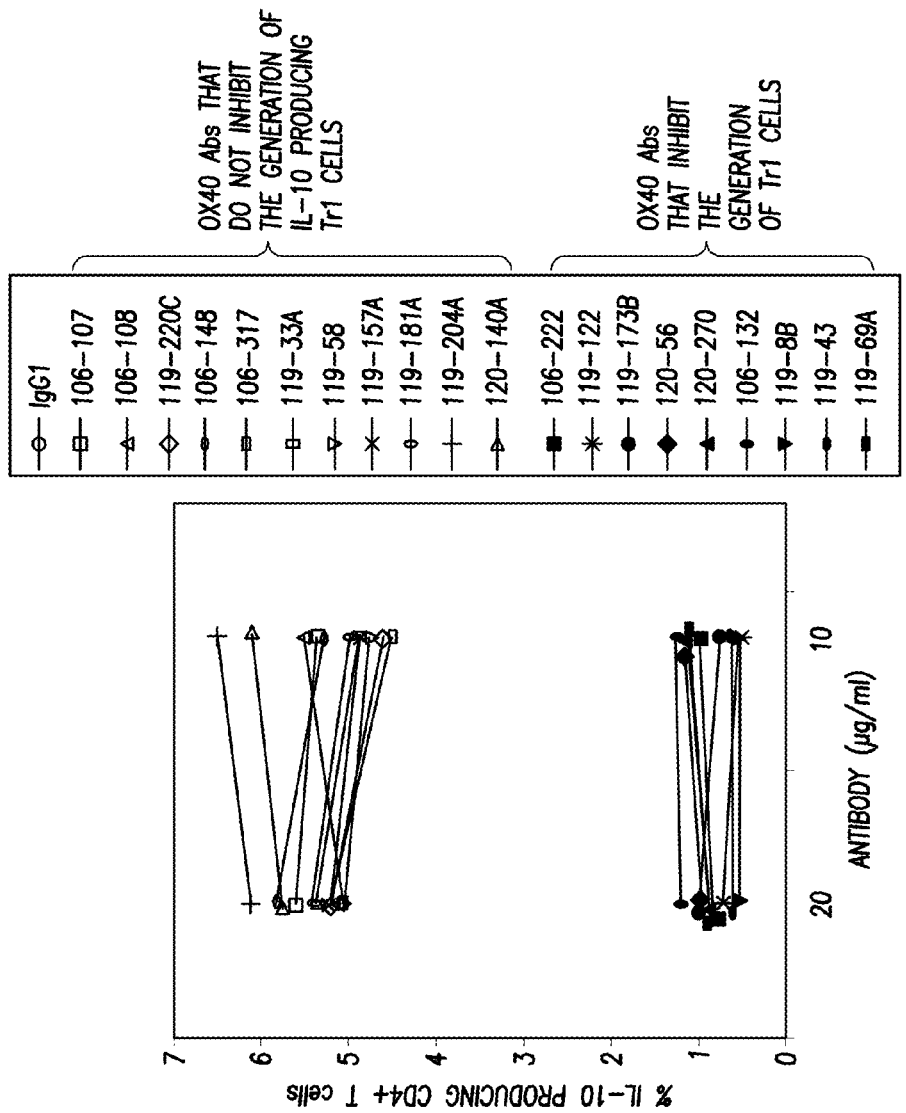
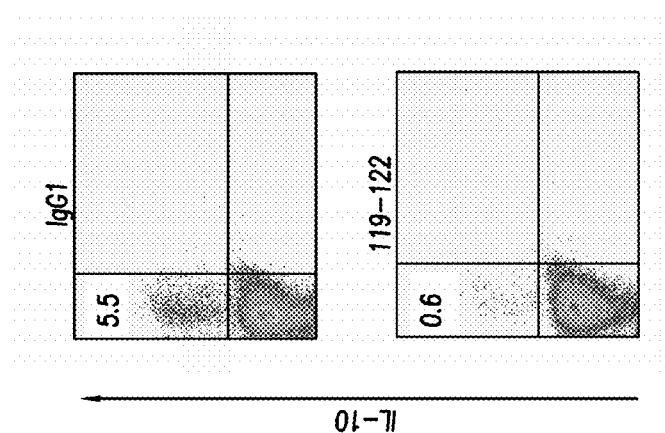
FIG. 13B
FIG. 13A

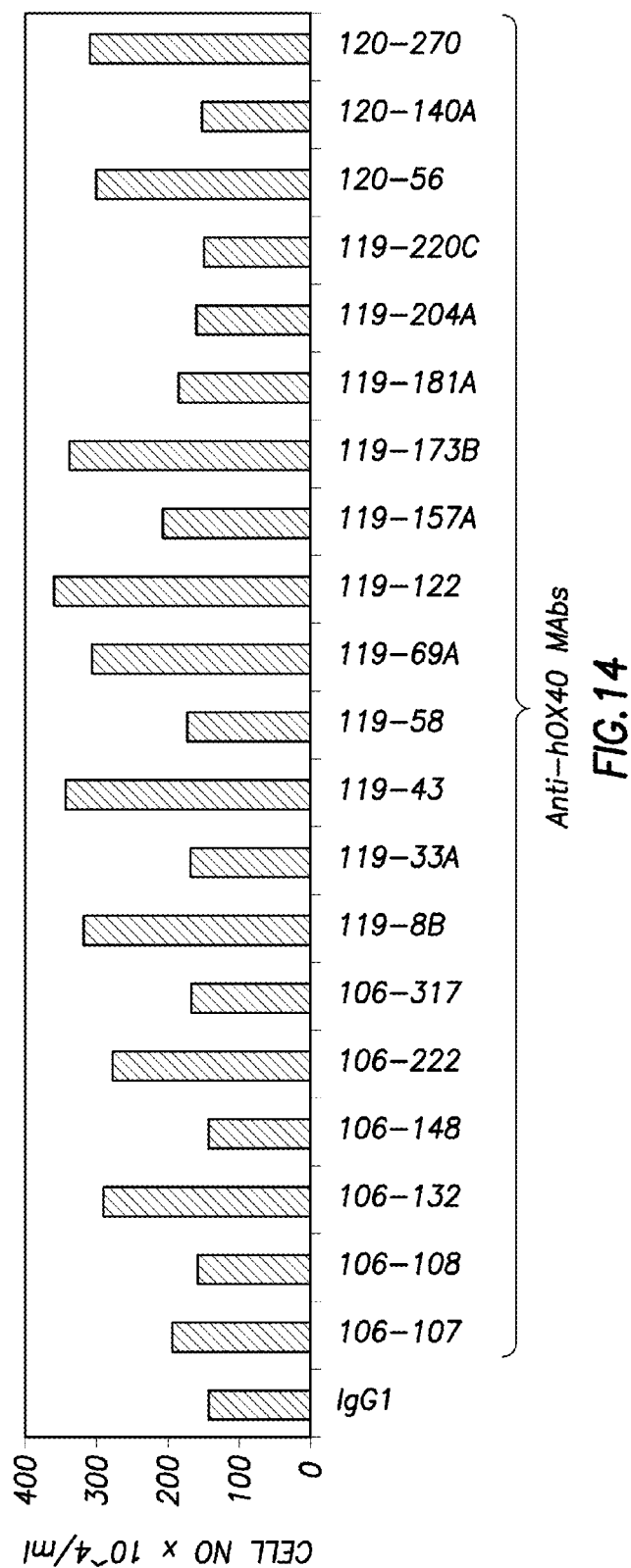

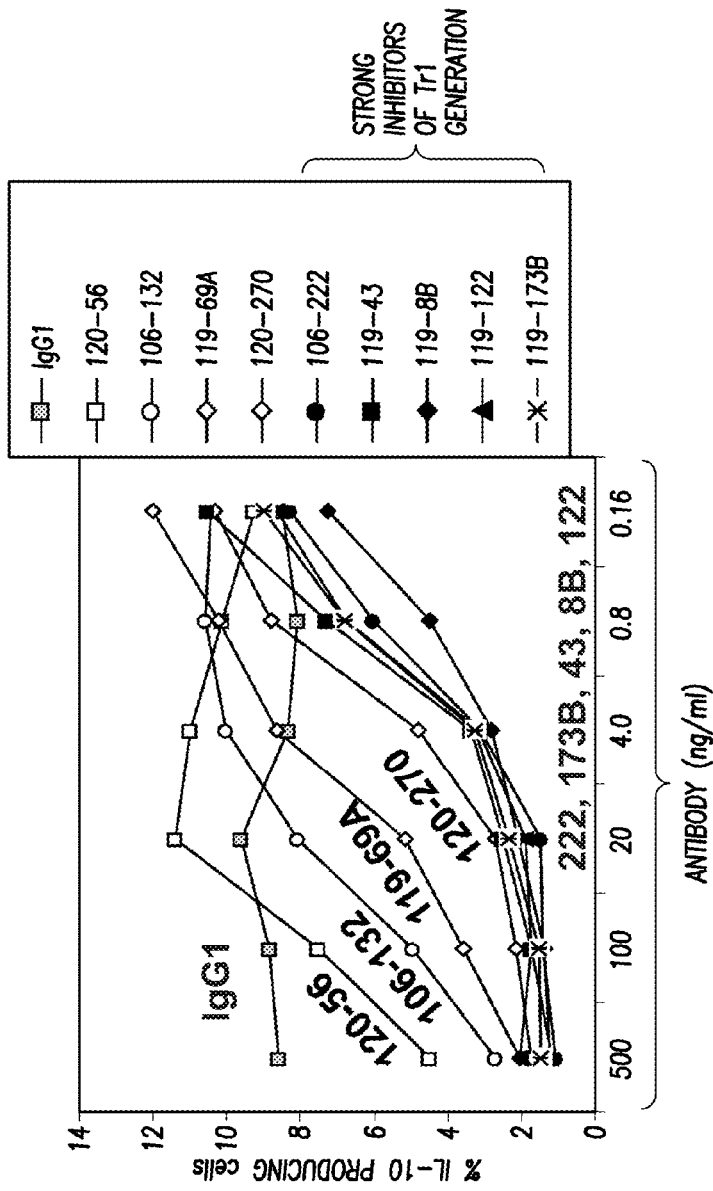
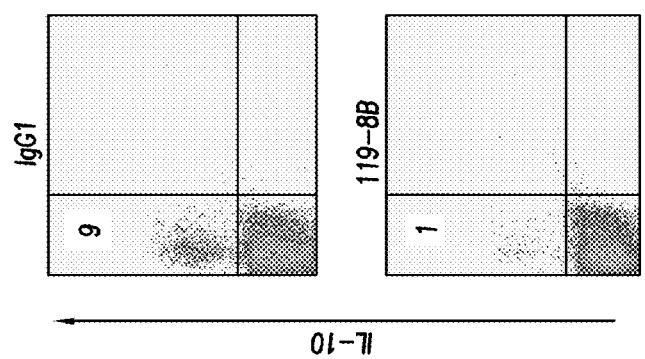
FIG. 15B
FIG. 15A

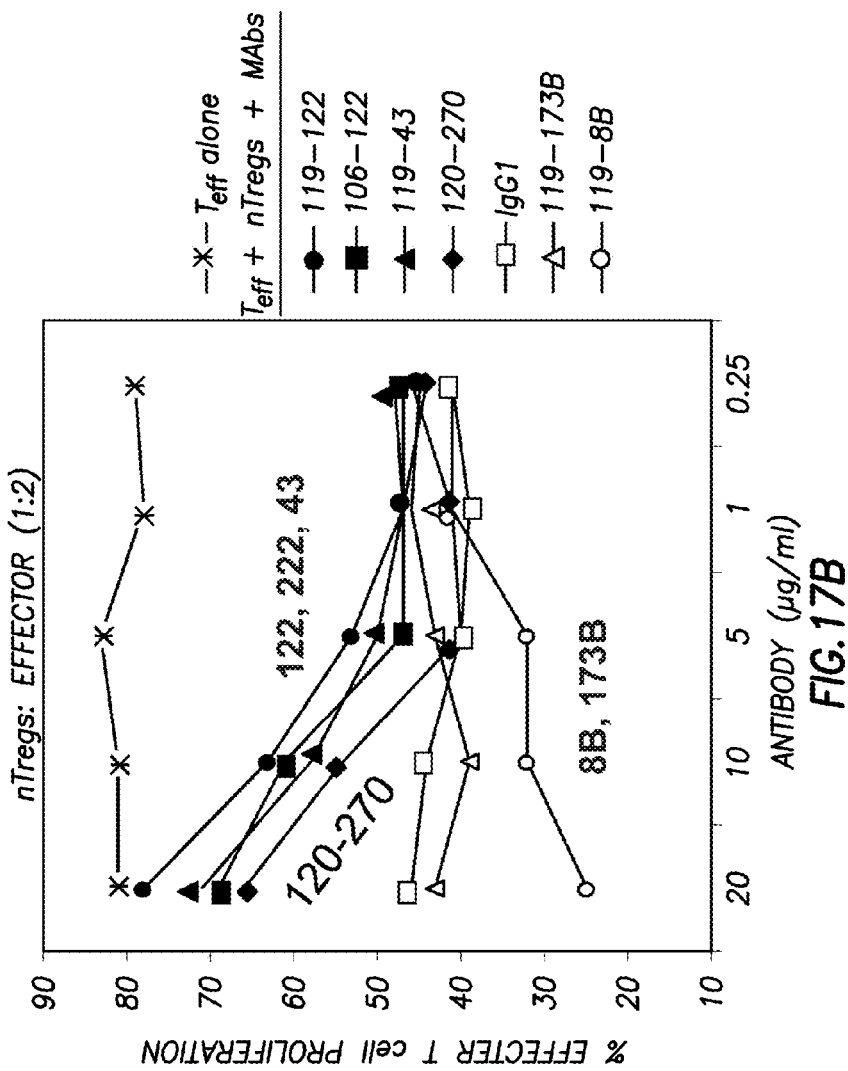
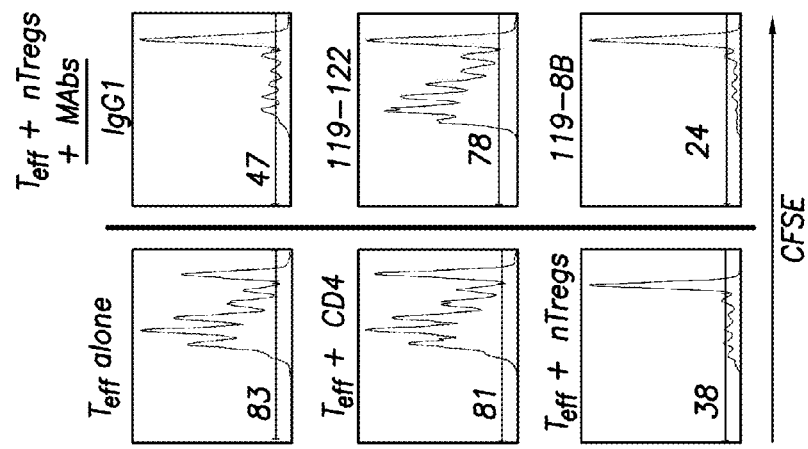
FIG. 17B
FIG. 17A

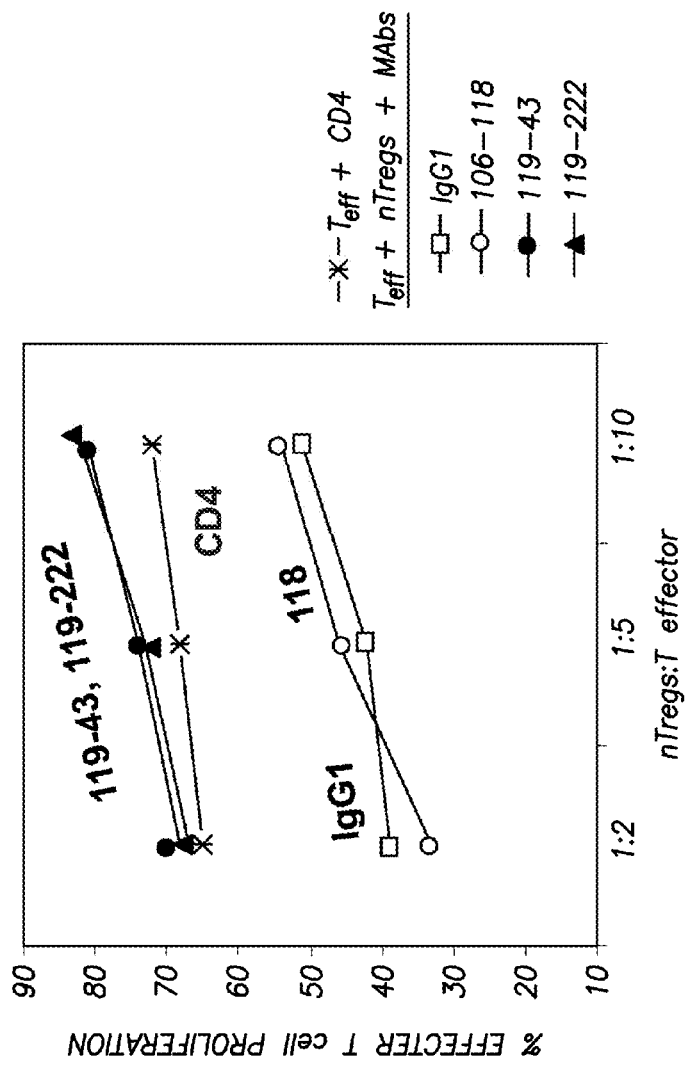
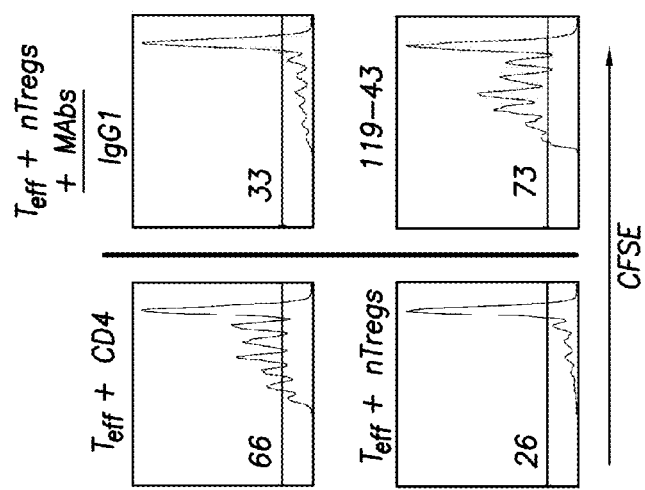

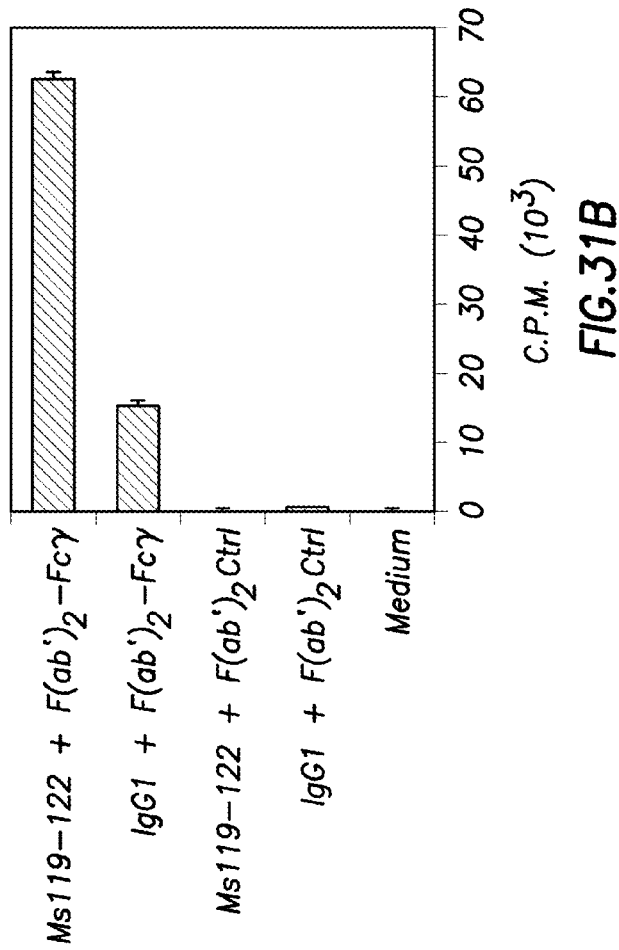
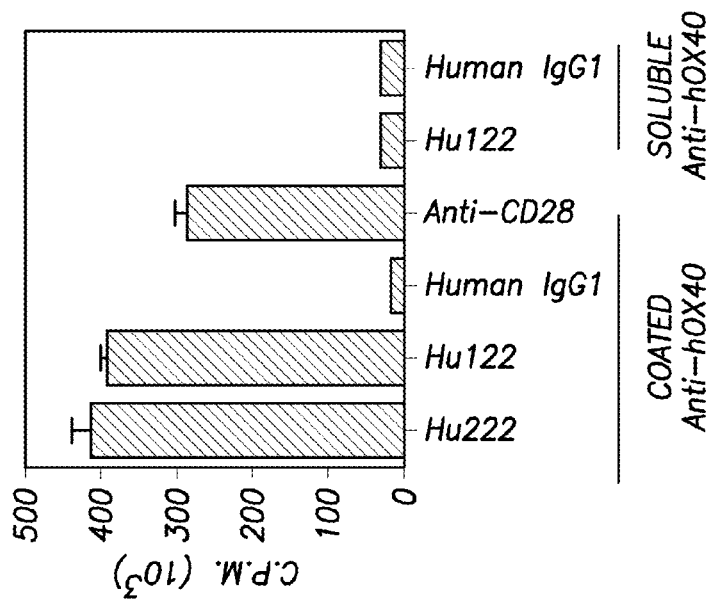
FIG. 31B
FIG. 31A

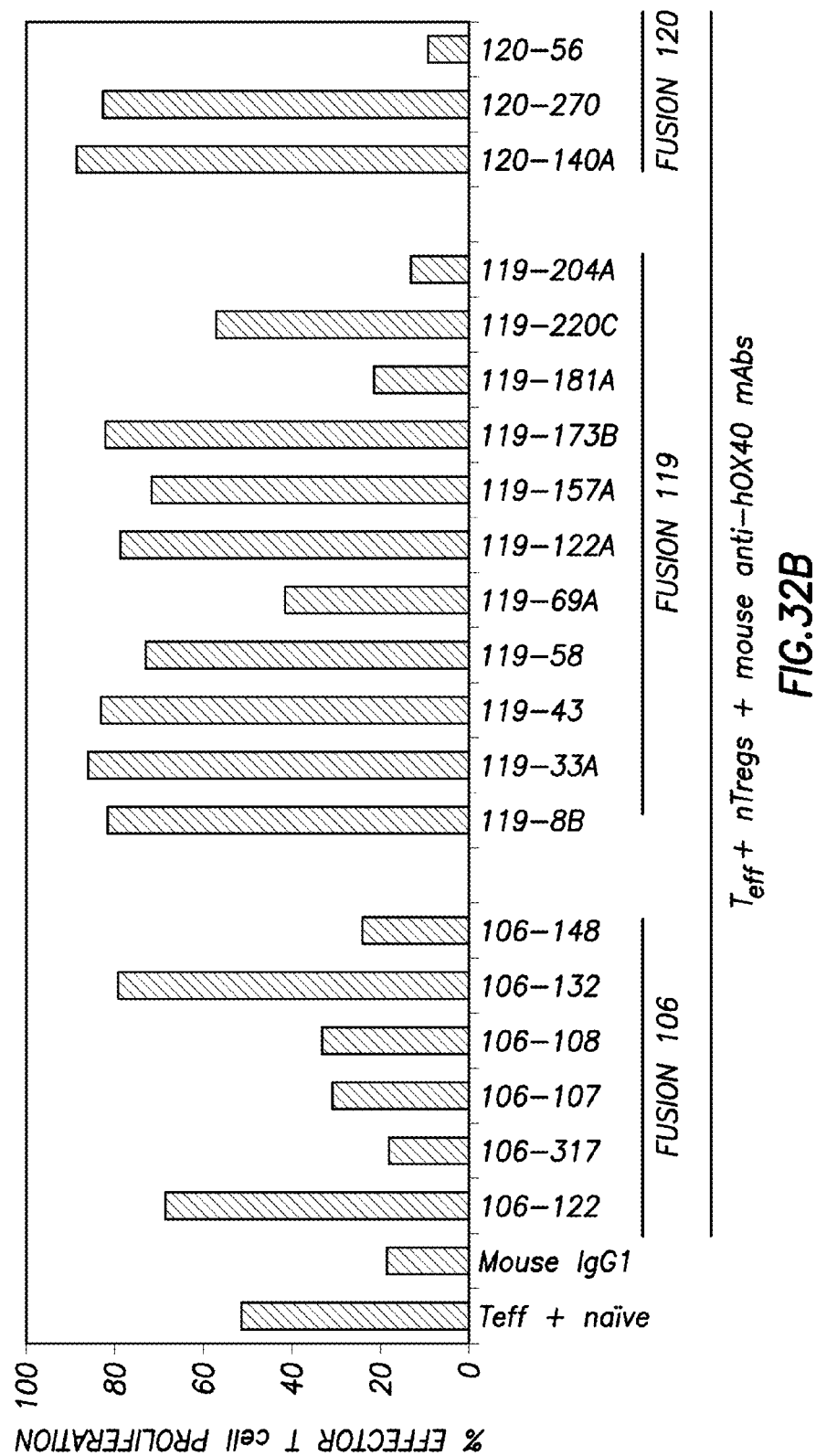

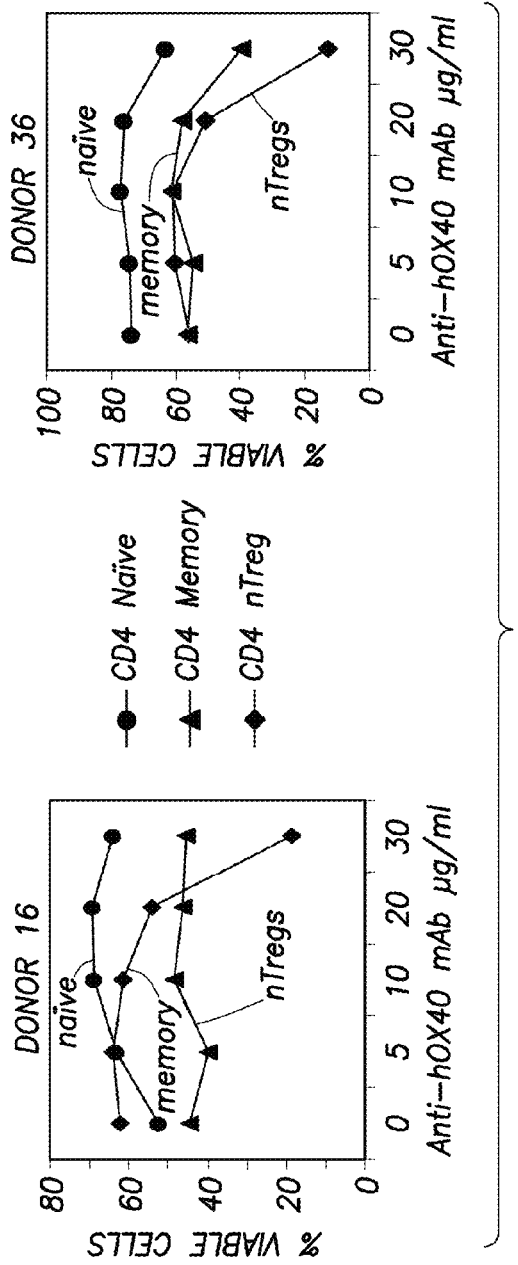
FIG. 33A
FIG. 33B
FIG. 33C 106-222 VH

```
                         1                   2                    3
             123456789  0123456789  0123456789  0123456789         CDR1 SEQ ID No.1
106-222 VH   QIQLVQSGP  ELKKPGETVK  ISCKASGYTF  TDYSMHWVKQ
Hu106 VH     QVQLVQSGS  ELKKPGASVK  VSCKASGYTF  TDYSMHWVRQ
X61012       QVQLVQSGS  ELKKPGASVK  VSCKASGYTF  T----WVRQ 4          5           6           7
             0123456789  0122345678  9 0123456789  0123456789
                              a             CDR2 SEQ1D No.2
106-222 VH   APGKGLKWMG  WINTETGEPTY  ADDFKGRFAF  SLETSASTAY
Hu106 VH     APGQGLKWMG  WINTETGEPTY  ADDFKGRFVF  SLDTSVSTAY
X61012       APGQGLEWMG  ----------   ----RFVF    SLDTSVSTAY 1          1
                  8           9          0           
             0122223456789  0123456789  00000012345678 9 0123
                  abc                        abcde           CDR3 SEQ ID No.3
106-222 VH   LQINNLKNEDTAT  YFCANPYYDY  VSYYAMDYWGHGTSV  TVSS
Hu106 VH     LQISSLKAEDTAV  YYCANPYYDY  VSYYAMDYWGQGTTV  TVSS
X61012       LQISSLKAEDTAV  YYCAR----   ----------WGKGTTV TVSS
```

SEQ ID No.4 106-222 VH
SEQ ID No.5 Hu106 VH
SEQ ID NO. 25 X61012

```
                                      CDR1 SEQ ID No.7
                           1          2        3
              123456789 0123456789 0123456789 0123456789
SEQ ID No.10  106-222 VL  DIVMTQSHK FMSTSVRDRV SITCKASQDV STAVAWYQQK
SEQ ID No.11  Hu106 VL    DIQMTQSPS SLSASVGDRV TITCKASQDV STAVAWYQQK
SEQ ID No.26  AJ388641    DIQMTQSPS SLSASVGDRV TITC------ -----WYQQK

CDR2 SEQ ID No.8
                          4        5         6          7
              0123456789 0123456789 0123456789 0123456789
106-222 VL    PGQSPKLLIY SASYLYTGVP DRFTGSGSGT DFTFTISSVQ
Hu106 VL      PGKAPKLLIY SASYLYTGVP SRFSGSGSGT DFTFTISSLQ
AJ388641      PGKAPKLLIY ------GVP SRFSGSGSGT DFTFTISSLQ

CDR3 SEQ ID No.9
                          8        9         1        
                                             0        
              0123456789 0123456789 01234567
106-222 VL    AEDLAVYYCQ QHYSTPRTFG GGTKLEIK
Hu106 VL      PEDIATYYCQ QHYSTPRTFG QGTKLEIK
AJ388641      PEDIATYYC- ------FG QGTKLEIK
```

FIG.37

Hu106-222 VH
SpeI
ACTAGTACCACCATGGCTTGGGTGTGGACCTTGCTATTCCTGATGGCAGCTGCCAAAGT
          M  A  W  V  W  T  L  L  F  L  M  A  A  A  Q  S

SEQ ID No.6

ATCCAAGCACAGGTTCAGTTGGTGCAGTCTGGAGCTGAAGAAGCCTGAGGCTCA
 I  Q  A  Q  V  Q  L  V  Q  S  G  S  E  L  K  K  P  G  A  S

GTCAAGGTTTCCTGCAAGGCTTCTGGTTATACCTTCACAGACTATTCAATGCACTGGGTG
 V  K  V  S  C  K  A  S  G  Y  T  F  T  D  Y  S  M  H  W  V

CGACAGGCTCCAGGACAAGGTTTAAAGTGGATGGGCTGGATAAACACTGAGACTGGTGAG
 R  Q  A  P  G  Q  G  L  K  W  M  G  W  I  N  T  E  T  G  E

CCAACATATGCAGATGACTTCAAGGGACGGTTTGTCTTCTCTTTGGACACCTCTGTCAGC
 P  T  Y  A  D  D  F  K  G  R  F  V  F  S  L  D  T  S  V  S

ACTGCCTATTTGCAGATCAGCAGCCTCAAAGCTGAGGACACGGCTGTGTATTACTGTGCT
 T  A  Y  L  Q  I  S  S  L  K  A  E  D  T  A  V  Y  Y  C  A

AATCCCTACTATGATTACGTCTCTTACTATGCTATGGACTACTGGGGTCAGGGAACCACG
 N  P  Y  Y  D  Y  V  S  Y  Y  A  M  D  Y  W  G  Q  G  T  T

HindIII
GTCACCGTCTCCTCAGGTAAGAATGGCCTCTCAAGCTT
 V  T  V  S  S

NheI

SEQ ID No.12 GCTAGCACCACCATGGAGTCACAGATTCAGGTCTTTGTATTCGTGTTTCTCTGGTTGTCT
            M  E  S  Q  I  Q  V  F  V  F  L  W  L  S

GGTGTTGACGGAGACATTCAGATGACCCAGTCTCCATCCTCCCTGTCCGCATCAGTGGGA
 G  V  D  G  D  I  Q  M  T  Q  S  P  S  S  L  S  A  S  V  G

GACAGGGTCACCATCACCTGCAAGGCCAGTCAGGATGTGAGTACTGCTGTAGCCTGGTAT
 D  R  V  T  I  T  C  K  A  S  Q  D  V  S  T  A  V  A  W  Y

CAACAGAAACCAGGAAAAGCCCCTAAACTACTGATTTACTCGGCATCCTACCTCTACACT
 Q  Q  K  P  G  K  A  P  K  L  L  I  Y  S  A  S  Y  L  Y  T

GGAGTCCCCTTCAGCGCTTCAGTGGCAGTGGATCTGGGACGGATTTCACTTTCACCATCAGC
 G  V  P  S  R  F  S  G  S  G  S  G  T  D  F  T  F  T  I  S

AGTCTGCAGCCTGAAGACATTGCAACATATTACTGTCAGCAACATTATAGTACTCCTCGG
 S  L  Q  P  E  D  I  A  T  Y  Y  C  Q  Q  H  Y  S  T  P  R

EcoRI
ACGTTCGGTCAGGGCACCAAGCTGGAAATCAAACGTAAGTAGAATCCAAAGAATTC
 T  F  G  Q  G  T  K  L  E  I  K 119-122 VH

```
                              1          2          3
             123456789 0123456789 0123456789 0123456789          CDR1 SEQ ID No.13
119-122 VH   EVQLVESGG  GLVQPGESLK LSCESNEYEF PSHDMSWVRK
Hu119  VH    EVQLVESGG  GLVQPGGSLR LSCAASEYEF PSHDMSWVRQ
Z14189       EVQLVESGG  GLVQPGGSLR LSCAASGFTF S-----WVRQ 4           5            6          7
             0123456789 01222456789 0123456789 0123456789        CDR2 SEQ ID No.14
                              a
119-122 VH   TPEKRLELVA AINSDGGSTYY PDTMERRFII SRDNTKKTLY
Hu119  VH    APGKGLELVA AINSDGGSTYY PDTMERRFTI SRDNAKNSLY
Z14189       APGKGLEWVA ---------- -------RFTI SRDNAKNSLY 1          1
                 8          9          0000123456789 0123        CDR3 SEQ ID No.15
             0122223456789 0123456789          abc
119-122 VH   LQMSSLRSEDTAL YYCARHYDDY YAWFAYWGQGTLV TVSA
Hu119  VH    LQMNSLRAEDTAV YYCARHYDDY YAWFAYWGQGTMV TVSS
Z14189       LQMNSLRAEDTAV YYCAR----- -----WGQGTMV TVSS
```

SEQ ID No.16    119-122 VH
SEQ ID No.17    Hu119 VH
SEQ ID No.27    Z14189

```
                          1                   2                              3
            123456789 0123456789 01234567777789 0123456789   CDR1 SEQ ID No.19
                                          abcd
SEQ ID No.22  119-122 VL  DIVLTQSPA SLAVSLGQRA TISCRASKSVSTSG YSYMHWYQQK
SEQ ID No.23  Hu119 VL    EIVLTQSPA TLSLSPGERA TLSCRASKSVSTSG YSYMHWYQQK
SEQ ID No.28  M29469      EIVLTQSPA TLSLSPGERA TLSC---------- ----WYQQK
                                                 CDR2 SEQ ID No.20
                       4         5          6          7
            0123456789 0123456789 0123456789 0123456789
119-122 VL  PGQPPKLLIY LASNLESGVP ARFSGSGSGT DFTLNIHPVE
Hu119 VL    PGQAPRLLIY LASNLESGVP ARFSGSGSGT DFTLTISSLE
M29469      PGQAPRLLIY -------GVP ARFSGSGSGT DFTLTISSLE
              CDR3 SEQ ID No.21
                       8          9          0          1
            0123456789 0123456789 01234567
119-122 VL  EEDAATYYCQ HSRELPLTFG AGTKLELK
Hu119 VL    PEDFAVYYCQ HSRELPLTFG GGTKVEIK
M29469      PEDFAVYYC- --------FG GGTKVEIK
```

FIG.41

Hu119-122 VH
SpeI
ACTAGTACCACCATGGAGACTTCGGGGCTCAGCTTGGTTTTCCTTGTCCTTATTTTAAAAAGT
          M  D  F  G  L  S  L  V  F  L  V  L  I  L  K  S

GTACAGTGTGAGGTGCAGCTGGTGGAGTCTGGGGGAGGCTTAGTGCAGCCTGGAGGGTCC
 V  Q  C  E  V  Q  L  V  E  S  G  G  G  L  V  Q  P  G  G  S

CTGAGACTCTCCTGTGCAGCCTCTGAATACGAGTTCCCTTCCCATGACATGTCTTGGGTC
 L  R  L  S  C  A  A  S  E  Y  E  F  P  S  H  D  M  S  W  V

CGCCAGGCTCCGGGGAAGGGGCTGGAGTTGGTCGCAGCCATTAATAGTGATGGTGGTAGC
 R  Q  A  P  G  K  G  L  E  L  V  A  A  I  N  S  D  G  G  S

ACCTACTATCCAGACACCATGGAGAGACGATTCACCATCTCCAGAGACAATGCCAAGAAC
 T  Y  Y  P  D  T  M  E  R  R  F  T  I  S  R  D  N  A  K  N

TCACTGTACCTGCAAATGAACAGTCTGAGGGCCGAGGACACAGCCGTGTATTACTGTGCA
 S  L  Y  L  Q  M  N  S  L  R  A  E  D  T  A  V  Y  Y  C  A

AGAGACACTATGATGATTACGCCTGGTTTGCTTACTGGGGCCAAGGGACTATGGTCACT
 R  H  Y  D  D  Y  Y  A  W  F  A  Y  W  G  Q  G  T  M  V  T

HindIII
GTCTCTTCAGGTGAGTCCTAACTTCAAGCTT
 V  S  S

SEQ ID No.18

FIG.42

119-122 VL
NheI
GCTAGCACCACCATGGAGACAGACACTCCTGTTATGGGTACTGCTGCTCTGGGTTCCA
         M  E  T  D  T  L  L  L  W  V  L  L  L  W  V  P

GGTTCCACTGGTGAAATTGTGCTGACACAGTCTCCTGCTACCTTATCTTTGTCTCCAGGG
 G  S  T  G  E  I  V  L  T  Q  S  P  A  T  L  S  L  S  P  G

GAAAGGGCCACCCTCTCATGCAGGGCCAGCCAGAAAGTGTCAGTACACATCTGGCTATAGTTAT
 E  R  A  T  L  S  C  R  A  S  Q  S  V  S  T  S  G  Y  S  Y

ATGCACTGGTACCAACAGAAACCAGGACAGGCTCCCAGACTCCTCATCTATCTTGCATCC
 M  H  W  Y  Q  Q  K  P  G  Q  A  P  R  L  L  I  Y  L  A  S

AACCTAGAATCTGGGGTCCCTGCCAGGTTCAGTGGCAGTGGGTCTGGGACAGACTTCACC
 N  L  E  S  G  V  P  A  R  F  S  G  S  G  S  G  T  D  F  T

CTCACCATCAGCAGCAGCCTAGAGCCTGAGGATTTTGCAGTTTATTACTGTCAGCACAGTAGG
 L  T  I  S  S  L  E  P  E  D  F  A  V  Y  Y  C  Q  H  S  R

GAGCTTCCGCTCACGTTCGGGCGGAGGGACCAAGGTCGAGATCAAACGTAAGTACACTTTT
 E  L  P  L  T  F  G  G  G  T  K  V  E  I  K

EcoRI
CTGAATTC

SEQ ID No.24

FIG.43

SEQUENCE LISTING

```
<160> NUMBER OF SEQ ID NOS: 30

<210> SEQ ID NO 1
<211> LENGTH: 5
<212> TYPE: PRT
<213> ORGANISM: Mus sp.

<400> SEQUENCE: 1

Asp Tyr Ser Met His
1               5

<210> SEQ ID NO 2
<211> LENGTH: 17
<212> TYPE: PRT
<213> ORGANISM: Mus sp.

<400> SEQUENCE: 2

Trp Ile Asn Thr Glu Thr Gly Glu Pro Thr Tyr Ala Asp Asp Phe Lys
1               5                   10                  15

Gly

<210> SEQ ID NO 3
<211> LENGTH: 13
<212> TYPE: PRT
<213> ORGANISM: Mus sp.

<400> SEQUENCE: 3
```

```
Pro Tyr Tyr Asp Tyr Val Ser Tyr Ala Met Asp Tyr
1               5                   10
```

```
<210> SEQ ID NO 4
<211> LENGTH: 122
<212> TYPE: PRT
<213> ORGANISM: Mus sp.

<400> SEQUENCE: 4

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Asn Pro Tyr Tyr Asp Tyr Val Ser Tyr Tyr Ala Met Asp Tyr Trp
            100                 105                 110

Gly His Gly Thr Ser Val Thr Val Ser Ser
        115                 120
```

```
<210> SEQ ID NO 5
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Ser Met His Trp Val Arg Gln Ala Pro Gly Gln Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Asn Pro Tyr Tyr Asp Tyr Val Ser Tyr Tyr Ala Met Asp Tyr Trp
            100                 105                 110

Gly Gln Gly Thr Thr Val Thr Val Ser Ser
        115                 120
```

```
<210> SEQ ID NO 6
<211> LENGTH: 458
<212> TYPE: DNA
<213> ORGANISM: Artificial Sequence
<220> FEATURE:
<223> OTHER INFORMATION: Description of Artificial Sequence: Synthetic
      polynucleotide
```

-continued

```
<400> SEQUENCE: 6
actagtacca ccatggcttg ggtgtggacc ttgctattcc tgatggcagc tgcccaaagt      60
atccaagcac aggttcagtt ggtgcagtct ggatctgagc tgaagaagcc tggagcctca     120
gtcaaggttt cctgcaaggc ttctggttat accttcacag actattcaat gcactgggtg     180
cgacaggctc caggacaagg tttaaagtgg atgggctgga taaacactga gactggtgag     240
ccaacatatg cagatgactt caagggacgg tttgtcttct ctttggacac ctctgtcagc     300
actgcctatt tgcagatcag cagcctcaaa gctgaggaca cggctgtgta ttactgtgct     360
aatcccract atgattacgt ctcttactat gctatggact actggggtca gggaaccacg     420
gtcaccgtct cctcaggtaa gaatggcctc tcaagctt                             458
```

```
<210> SEQ ID NO 7
<211> LENGTH: 11
<212> TYPE: PRT
<213> ORGANISM: Mus sp.

<400> SEQUENCE: 7

Lys Ala Ser Gln Asp Val Ser Thr Ala Val Ala
1               5                   10

<210> SEQ ID NO 8
<211> LENGTH: 7
<212> TYPE: PRT
<213> ORGANISM: Mus sp.

<400> SEQUENCE: 8

Ser Ala Ser Tyr Leu Tyr Thr
1               5

<210> SEQ ID NO 9
<211> LENGTH: 9
<212> TYPE: PRT
<213> ORGANISM: Mus sp.

<400> SEQUENCE: 9

Gln Gln His Tyr Ser Thr Pro Arg Thr
1               5

<210> SEQ ID NO 10
<211> LENGTH: 107
<212> TYPE: PRT
<213> ORGANISM: Mus sp.

<400> SEQUENCE: 10

Asp Ile Val Met Thr Gln Ser His Lys Phe Met Ser Thr Ser Val Arg
1               5                   10                  15

Asp Arg Val Ser Ile Thr Cys Lys Ala Ser Gln Asp Val Ser Thr Ala
                20                  25                  30

Val Ala Trp Tyr Gln Gln Lys Pro Gly Gln Ser Pro Lys Leu Leu Ile
            35                  40                  45

Tyr Ser Ala Ser Tyr Leu Tyr Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Arg
                85                  90                  95

Thr Phe Gly Gly Gly Thr Lys Leu Glu Ile Lys
            100                 105
```

```
                100             105

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Leu Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln His Tyr Ser Thr Pro Arg
                85                  90                  95

Thr Phe Gly Gln Gly Thr Lys Leu Glu Ile Lys
            100                 105

<210> SEQ ID NO 12
<211> LENGTH: 416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gctagcacca ccatggagtc acagattcag gtctttgtat tcgtgtttct ctggttgtct     60
ggtgttgacg gagacattca gatgacccag tctccatcct ccctgtccgc atcagtggga    120
gacagggtca ccatcacctg caaggccagt caggatgtga gtactgctgt agcctggtat    180
caacagaaac caggaaaagc ccctaaacta ctgatttact cggcatccta cctctacact    240
ggagtccctt cacgcttcag tggcagtgga tctgggacgg atttcacttt caccatcagc    300
agtctgcagc ctgaagacat tgcaacatat tactgtcagc aacattatag tactcctcgg    360
acgttcggtc agggcaccaa gctggaaatc aaacgtaagt agaatccaaa gaattc        416

<210> SEQ ID NO 13
<211> LENGTH: 5
<212> TYPE: PRT
<213> ORGANISM: Mus sp.

<400> SEQUENCE: 13

Ser His Asp Met Ser
1               5

<210> SEQ ID NO 14
<211> LENGTH: 17
<212> TYPE: PRT
<213> ORGANISM: Mus sp.

<400> SEQUENCE: 14

Ala Ile Asn Ser Asp Gly Gly Ser Thr Tyr Tyr Pro Asp Thr Met Glu
```

-continued

```
1               5                   10                  15
Arg

<210> SEQ ID NO 15
<211> LENGTH: 11
<212> TYPE: PRT
<213> ORGANISM: Mus sp.

<400> SEQUENCE: 15

His Tyr Asp Asp Tyr Tyr Ala Trp Phe Ala Tyr
1               5                   10

<210> SEQ ID NO 16
<211> LENGTH: 120
<212> TYPE: PRT
<213> ORGANISM: Mus sp.

<400> SEQUENCE: 16

Glu Val Gln Leu Val Glu Ser Gly Gly Gly Leu Val Gln Pro Gly Glu
1               5                   10                  15

Ser Leu Lys Leu Ser Cys Glu Ser Asn Glu Tyr Glu Phe Pro Ser His
            20                  25                  30

Asp Met Ser Trp Val Arg Lys Thr Pro Glu Lys Arg Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Ile Ile Ser Arg Asp Asn Thr Lys Lys Thr Leu Tyr
65                  70                  75                  80

Leu Gln Met Ser Ser Leu Arg Ser Glu Asp Thr Ala Leu Tyr Tyr Cys
                85                  90                  95

Ala Arg His Tyr Asp Asp Tyr Tyr Ala Trp Phe Ala Tyr Trp Gly Gln
            100                 105                 110

Gly Thr Leu Val Thr Val Ser Ala
        115                 120

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Glu Tyr Glu Phe Pro Ser His
            20                  25                  30

Asp Met Ser Trp Val Arg Gln Ala Pro Gly Lys Gly Leu Glu Leu Val
        35                  40                  45

Ala Ala Ile Asn Ser Asp Gly Gly Ser Thr Tyr Tyr Pro Asp Thr Met
    50                  55                  60

Glu Arg Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Asp Asp Tyr Tyr Ala Trp Phe Ala Tyr Trp Gly Gln
            100                 105                 110
```

-continued

```
Gly Thr Met Val Thr Val Ser Ser
         115                 120
```

<210> SEQ ID NO 18
<211> LENGTH: 451
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
actagtacca ccatggactt cgggctcagc ttggttttcc ttgtccttat tttaaaaagt    60
gtacagtgtg aggtgcagct ggtggagtct gggggaggct tagtgcagcc tggagggtcc   120
ctgagactct cctgtgcagc ctctgaatac gagttcccct cccatgacat gtcttgggtc   180
cgccaggctc cggggaaggg gctggagttg gtcgcagcca ttaatagtga tggtggtagc   240
acctactatc agacaccat ggagagacga ttcaccatct ccagacaca tgccaagaac    300
tcactgtacc tgcaaatgaa cagtctgagg gccgaggaca cagccgtgta ttactgtgca   360
agacactatg atgattacta cgcctggttt gcttactggg gccaagggac tatggtcact   420
gtctcttcag gtgagtccta acttcaagct t                                   451
```

<210> SEQ ID NO 19
<211> LENGTH: 15
<212> TYPE: PRT
<213> ORGANISM: Mus sp.

<400> SEQUENCE: 19

```
Arg Ala Ser Lys Ser Val Ser Thr Ser Gly Tyr Ser Tyr Met His
1               5                   10                  15
```

<210> SEQ ID NO 20
<211> LENGTH: 7
<212> TYPE: PRT
<213> ORGANISM: Mus sp.

<400> SEQUENCE: 20

```
Leu Ala Ser Asn Leu Glu Ser
1               5
```

<210> SEQ ID NO 21
<211> LENGTH: 9
<212> TYPE: PRT
<213> ORGANISM: Mus sp.

<400> SEQUENCE: 21

```
Gln His Ser Arg Glu Leu Pro Leu Thr
1               5
```

<210> SEQ ID NO 22
<211> LENGTH: 111
<212> TYPE: PRT
<213> ORGANISM: Mus sp.

<400> SEQUENCE: 22

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45
```

```
Lys Leu Leu Ile Tyr Leu Ala Ser Asn Leu Glu Ser Gly Val Pro Ala
             50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                 85                  90                  95

Glu Leu Pro Leu Thr Phe Gly Ala Gly Thr Lys Leu Glu Leu Lys
            100                 105                 110
```

<210> SEQ ID NO 23
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Lys Ser Val Ser Thr Ser
             20                  25                  30

Gly Tyr Ser Tyr Met His Trp Tyr Gln Gln Lys Pro Gly Gln Ala Pro
         35                  40                  45

Arg Leu Leu Ile Tyr Leu Ala Ser Asn Leu Glu Ser Gly Val Pro Ala
     50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
                 85                  90                  95

Glu Leu Pro Leu Thr Phe Gly Gly Gly Thr Lys Val Glu Ile Lys
            100                 105                 110
```

<210> SEQ ID NO 24
<211> LENGTH: 428
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
gctagcacca ccatggagac agacacactc ctgttatggg tactgctgct ctgggttcca      60
ggttccactg gtgaaattgt gctgacacag tctcctgcta ccttatcttt gtctccaggg     120
gaaagggcca cctctcatg cagggccagc aaaagtgtca gtacatctgg ctatagttat      180
atgcactggt accaacagaa accaggacag gctcccagac tcctcatcta tcttgcatcc     240
aacctagaat ctggggtccc tgccaggttc agtggcagtg gtctgggac agacttcacc      300 ctcaccatca gcagcctaga gcctgaggat tttgcagttt attactgtca gcacagtagg     360
gagcttccgc tcacgttcgg cggagggacc aaggtcgaga tcaaacgtaa gtacactttt     420
ctgaattc                                                              428
```

<210> SEQ ID NO 25
<211> LENGTH: 87
<212> TYPE: PRT
<213> ORGANISM: Homo sapiens

<400> SEQUENCE: 25

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Trp Val
            20                  25                  30

Arg Gln Ala Pro Gly Gln Gly Leu Glu Trp Met Gly Arg Phe Val Phe
        35                  40                  45

Ser Leu Asp Thr Ser Val Ser Thr Ala Tyr Leu Gln Ile Ser Ser Leu
    50                  55                  60

Lys Ala Glu Asp Thr Ala Val Tyr Tyr Cys Ala Arg Trp Gly Lys Gly
65                  70                  75                  80

Thr Thr Val Thr Val Ser Ser
                85

<210> SEQ ID NO 26
<211> LENGTH: 80
<212> TYPE: PRT
<213> ORGANISM: Homo sapiens

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
        35                  40                  45

Ser Gly Thr Asp Phe Thr Phe Thr Ile Ser Ser Leu Gln Pro Glu Asp
    50                  55                  60

Ile Ala Thr Tyr Tyr Cys Phe Gly Gln Gly Thr Lys Leu Glu Ile Lys
65                  70                  75                  80

<210> SEQ ID NO 27
<211> LENGTH: 87
<212> TYPE: PRT
<213> ORGANISM: Homo sapiens

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Trp Val
            20                  25                  30

Arg Gln Ala Pro Gly Lys Gly Leu Glu Trp Val Ala Arg Phe Thr Ile
        35                  40                  45

Ser Arg Asp Asn Ala Lys Asn Ser Leu Tyr Leu Gln Met Asn Ser Leu
    50                  55                  60

Arg Ala Glu Asp Thr Ala Val Tyr Tyr Cys Ala Arg Trp Gly Gln Gly
65                  70                  75                  80

Thr Met Val Thr Val Ser Ser
                85

<210> SEQ ID NO 28
<211> LENGTH: 80
<212> TYPE: PRT
<213> ORGANISM: Homo sapiens

<400> SEQUENCE: 28

Glu Ile Val Leu Thr Gln Ser Pro Ala Thr Leu Ser Leu Ser Pro Gly
1               5                   10                  15

```
Glu Arg Ala Thr Leu Ser Cys Trp Tyr Gln Gln Lys Pro Gly Gln Ala
            20                  25                  30

Pro Arg Leu Leu Ile Tyr Gly Val Pro Ala Arg Phe Ser Gly Ser Gly
        35                  40                  45

Ser Gly Thr Asp Phe Thr Leu Thr Ile Ser Ser Leu Glu Pro Glu Asp
    50                  55                  60

Phe Ala Val Tyr Tyr Cys Phe Gly Gly Gly Thr Lys Val Glu Ile Lys
65                  70                  75                  80

<210> SEQ ID NO 29
<211> LENGTH: 8
<212> TYPE: PRT
<213> ORGANISM: Artificial Sequence
<220> FEATURE:
<223> OTHER INFORMATION: Synthetic peptide

<400> SEQUENCE: 29

Ala Pro Glu Leu Leu Gly Gly Pro
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide

<400> SEQUENCE: 30

Ala Pro Glu Ala Ala Gly Gly Pro
1               5
```

ANTI-OX40 ANTIBODIES AND METHODS OF USING THE SAME

CROSS-REFERENCE TO RELATED APPLICATION

This application is a divisional of U.S. application Ser. No. 13/818,645, filed Feb. 22, 2013, which is a national phase application under 35 U.S.C. §371 of International Application No. PCT/US2011/048752, filed Aug. 23, 2011, which claims the benefit of and priority to U.S. Provisional Patent Application No. 61/375,999, filed Aug. 23, 2010, and U.S. Provisional Patent Application No. 61/380,827, filed Sep. 8, 2010. The entire text of each of the above-referenced disclosures is herein incorporated by reference.

STATEMENT REGARDING FEDERALLY SPONSORED RESEARCH OR DEVELOPMENT

This invention was made with government support under R01 AI061645-01, R01 AI062888-01, and U19 AI071130-01 awarded by the National Institutes of Health. The government has certain rights in the invention.

REFERENCE TO SEQUENCE LISTING

This disclosure includes a sequence listing submitted as a text file pursuant to 37 C.F.R. §1.52(e)(v) named "UTSCP1193USD1.txt", created on Apr. 9, 2015, with a size of ~14 KB, which is incorporated herein by reference. The attached sequence descriptions and Sequence Listing comply with the rules governing nucleotide and/or amino acid sequence disclosures in patent applications as set forth in 37 C.F.R. §§1.821-1.825. The Sequence Listing contains the one letter code for nucleotide sequence characters and the three letter codes for amino acids as defined in conformity with the IUPAC-IUBMB standards described in Nucleic Acids Res. 13:3021-3030 (1985) and in the Biochemical J. 219 (No. 2):345-373 (1984). The symbols and format used for nucleotide and amino acid sequence data comply with the rules set forth in 37 C.F.R. §1.822.

FIELD OF INVENTION

This invention relates generally to modulation of the OX40-receptor activation, and more particularly, to modulating the OX40-receptor to inhibit the immunosuppressive function of Interleukin 10 (IL-10) producing CD4$^+$ type 1 regulatory T cells ("Tr1 cells") and Foxp3$^+$-expressing regulatory T cells (also sometimes referred to herein as "Foxp3$^+$ T-reg" cells), and the generation of Tr1 cells from CD4$^+$ cells or naïve cells and IL-10 production.

THE NAMES OF THE PARTIES TO A JOINT RESEARCH AGREEMENT

None.

BACKGROUND OF THE INVENTION

Tr1 cells have a critical role in peripheral tolerance. Tr1 cells are particularly important in limiting tissue damage to the host during inflammatory immune responses. The generation of Tr1 cells accompanies both TH1 and TH2 immune responses in vivo and in vitro.

Tr1 cells are generated from naïve CD4$^+$ T cells during an antigen-driven T cell immune response. Tr1 cells are anergic in response to signaling through TCR, CD28 and IL-2 receptors and have the ability to suppress antigen-driven proliferation of naïve CD4$^+$ T cells in vivo and in vitro. Tr1 cells have the ability to inhibit the development of autoimmune diseases and limit the magnitude of immune responses to microbial pathogens.

While the molecular signals that lead to the Tr1 cells have been studied, little is known about the molecular signals that negatively regulate the generation of these cells. Although immunosuppressive drugs, cytokines, co-stimulatory molecules, and DCs have been implicated in the induction of Tr1 cells, signals that negatively regulate the generation of Tr1 cells remain elusive.

BRIEF SUMMARY OF THE INVENTION

Activation of the OX40 receptor blocks Tr1 generation from naïve or memory CD4$^+$ T cells as well as IL-10 production from Tr1 cells and the immunosuppressive function of the Tr1 cells. Activation of the OX40 receptor also blocks IL-10 production by Foxp3$^+$ T-reg cells and immunosuppressive function. As such, presented herein are agonist antibodies that bind to the OX40 receptor, whereby the agonist modulates the activation of the OX40 receptor to block IL-10 cytokine secretion and/or the Tr1 and Foxp3$^+$ T-reg cells overall immunosuppressive function. Essentially, the antibodies can mimic the OX40 ligand and trigger the OX40 receptor on Tr1 and/or on natural T regulatory cells ("nTregs"), also referred to as "Foxp3$^+$ T-regs."

As we shown in co-pending patent applications U.S. Ser. Nos. 11/659,266 and 12/861,135, OX40L inhibits the generation and function of IL-10-producing Tr1 cells from naïve and memory CD4+ T cells that were induced by the immunosuppressive drugs dexamethasone and vitamin D3. We discovered that OX40L inhibits the generation and function of IL-10 producing regulatory T cells. These discoveries demonstrate that signaling OX40 by OX40L suppresses the generation of human IL-10 producing immunosuppressive T cells in culture. This unique function of OX40L is not shared by two other co-stimulatory TNF-family members, GITR-ligand and 4-1BB-ligand. OX40L also strongly inhibits the generation and function of IL-10-producing Tr1 cells induced by two physiological stimuli provided by inducible co-stimulatory ligand and immature DCs. Signaling the OX40 receptor on human T cells by monoclonal antibodies, small molecules, or by the OX40L, or protein having at least 90 percent homology thereto, modulates and regulates the generation and function of IL-10 producing immunosuppressive T cells.

The discovery lends to numerous applications of treatment. For example, agonistic antibodies, small molecules, or OX40L could be used to suppress the generation and the function of IL-10 producing immunosuppressive T cells and therefore could be used to enhance immune responses to treat cancer and infectious diseases, or as an adjuvant for cancer vaccines. Antagonistic antibodies to OX40 or to OX40L, or antagonistic small molecules, could be used to enhance the generation and the function of IL-10-producing immunosuppressive T cells and therefore could be used for the development of therapies for autoimmune diseases and graft versus host diseases. Our discovery also provides for high throughput methods for screening antibodies or small molecules either activating the OX40 receptor (or conversely blocking OX40 signaling) on T cells for the development of therapeutics for cancer, or alternatively, autoimmune diseases, and graft versus host diseases.

Monoclonal and human antibodies (sometimes referred to herein as an "anti-OX40 antibody" and/or other variations of the same) that bind human OX40 receptor are provided herein. These antibodies are useful in the treatment or prevention of acute or chronic diseases or conditions whose pathology involves OX40. In one aspect, an isolated human antibody, or an antigen-binding portion thereof, that binds to human OX40 and is effective as a cancer treatment or treatment against an autoimmune disease is described. Any of the anti-OX40 antibodies disclosed herein may be used as a medicament. Any one or more of the anti-OX40 antibodies may be used to treat one or more a variety of cancers or autoimmune disease described herein.

Isolated humanized antibodies that bind to OX40 are provided herein. The isolated antibodies as described herein bind to OX40, and may bind to OX40 encoded from the following genes: NCBI Accession Number NP_003317, Genpept Accession Number P23510, or genes having 90 percent homology thereto. The isolated antibody provided herein may further bind to the OX40 receptor having one of the following GenBank Accession Numbers: AAB39944, CAE11757, or AAI05071.

As taught herein, exemplary is an isolated antibody which binds to OX40 comprising: (a) a heavy chain variable region CDR1 comprising the amino acid sequence of SEQ ID NO: 1; (b) a heavy chain variable region CDR2 comprising the amino acid sequence of SEQ ID NO: 2; (c) a heavy chain variable region CDR3 comprising the amino acid sequence of SEQ ID NO. 3; (d) a light chain variable region CDR1 comprising the amino acid sequence of SEQ ID NO. 7; (e) a light chain variable region CDR2 comprising the amino acid sequence of SEQ ID NO. 8; and (f) a light chain variable region CDR3 comprising the amino acid sequence of SEQ ID NO. 9.

Furthermore, another example is an isolated antibody which binds to OX40 comprising: (a) a heavy chain variable region CDR1 comprising the amino acid sequence of SEQ ID NO: 13; (b) a heavy chain variable region CDR2 comprising the amino acid sequence of SEQ ID NO: 14; (c) a heavy chain variable region CDR3 comprising the amino acid sequence of SEQ ID NO. 15; (d) a light chain variable region CDR1 comprising the amino acid sequence of SEQ ID NO. 19; (e) a light chain variable region CDR2 comprising the amino acid sequence of SEQ ID NO. 20; and (f) a light chain variable region CDR3 comprising the amino acid sequence of SEQ ID NO. 21.

Alternatively, an isolated antibody may have a heavy chain variable region CDR1 comprising the amino acid sequence of SEQ ID NO: 1 or 13; a heavy chain variable region CDR2 comprising the amino acid sequence of SEQ ID NO: 2 or 14; and/or a heavy chain variable region CDR3 comprising the amino acid sequence of SEQ ID NO: 3 or 15, or a heavy chain variable region CDR having 90 percent homology thereto.

Further, an isolated antibody may have a light chain variable region CDR1 comprising the amino acid sequence of SEQ ID NO: 7 or 19; a light chain variable region CDR2 comprising the amino acid sequence of SEQ ID NO: 8 or 20 and/or a light chain variable region CDR3 comprising the amino acid sequence of SEQ ID NO: 9 or 21, or a heavy chain variable region having 90 percent homology thereto.

The isolated antibody may have a light chain variable region ("VL") comprising the amino acid sequence of SEQ ID NO: 10, 11, 22 or 23, or an amino acid sequence with at least 90 percent identity to the amino acid sequences of SEQ ID NO: 10, 11, 22 or 23. The isolated antibody may have a heavy chain variable region ("VH") comprising the amino acid sequence of SEQ ID NO: 4, 5, 16 and 17, or an amino acid sequence with at least 90 percent identity to the amino acid sequences of SEQ ID NO: 4, 5, 16 and 17. As such, as an example, the isolated antibody may comprise a variable heavy sequence of SEQ ID NO:5 and a variable light sequence of SEQ ID NO: 11, or a sequence having 90 percent homology thereto. Similarly, the isolated antibody can have a variable heavy sequence of SEQ ID NO:17 and a variable light sequence of SEQ ID NO: 23 or a sequence having 90 percent homology thereto.

The isolated antibody may have variable light chain encoded by the nucleic acid sequence of SEQ ID NO: 12, or 24, or a nucleic acid sequence with at least 90 percent identity to the nucleotide sequences of SEQ ID NO: 12 or 24. The isolated antibody may have variable heavy chain encoded by a nucleic acid sequence of SEQ ID NO: 6 or 18, or a nucleic acid sequence with at least 90 percent identity to nucleotide sequences of SEQ ID NO: 6 or 18.

Also provided herein are monoclonal antibodies. The monoclonal antibodies may have a variable light chain comprising the amino acid sequence of SEQ ID NO: 10 or 22, or an amino acid sequence with at least 90 percent identity to the amino acid sequences of SEQ ID NO: 10 or 22. Further provided are monoclonal antibodies having a variable heavy chain comprising the amino acid sequence of SEQ ID NO: 4 or 16, or an amino acid sequence with at least 90 percent identity to the amino acid sequences of SEQ ID NO: 4 or 16.

Also provided herein is isolated nucleic acid encoding any of the anti-OX40 antibodies taught herein. Further provided herein are host cells, each comprising nucleic acid encoding any of the anti-OX40 antibodies described herein. Methods of producing an antibody (such as the host cell comprising nucleic acid encoding any of the anti-OX40 antibodies described herein) comprising culturing the host cell so that the antibody is produced, and/or recovering the antibody from the host cell, are further provided.

BRIEF DESCRIPTION OF THE DRAWINGS

So that the manner in which the above-recited features, aspects and advantages of the invention, as well as others that will become apparent, are attained and can be understood in detail, more particular description of the invention briefly summarized above can be had by reference to the embodiments thereof that are illustrated in the drawings that form a part of this specification. It is to be noted, however, that the appended drawings illustrate some embodiments of the invention and are, therefore, not to be considered limiting of the invention's scope, for the invention can admit to other equally effective embodiments.

FIG. 1 shows that FOXP3$^+$ Tregs infiltrated human follicular lymphoma (FL) tissues and co-localized with tumor B cells and monocytes. Left: Double immunostaining of FOXP3$^+$ Tregs (red) and CD20$^+$ B lymphoma cells (green); Right: FOXP3$^+$ Tregs (red) and CD11c$^+$ monocytes/macrophage/DC (green).

FIGS. 2A and 2B show increased numbers of CD4+ FOXP3$^+$ Tregs in patients with FL. Tumor cells and PBMCs were obtained from six patients with FL at initial diagnosis before therapy. PBMCs were also obtained from six normal donors for comparison. The percentages of regulatory T cells over total CD4$^+$ T cells were determined by flow cytometric analysis of CD4$^+$CD25$^+$CD127$^{low}$FOXP3$^+$ Tregs. FIG. 2A shows representative FACS analysis of Tregs. FL PBMC and FL tumor cells were divided from the same patient. FIG. 2B shows the percentage of Tregs of all donors. Horizontal bar indicate means.

FIG. 7A shows the intracellular analysis of cytokine production by naïve CD4$^+$ T cells as determined by flow cytometry according to an embodiment of a method of the present invention.

FIG. 7B shows IL-10 production by naïve CD4$^+$ T cells as determined by ELISA according to an embodiment of a method of the present invention.

FIG. 7C shows the number of viable T cells counted according to an embodiment of a method of the present invention.

FIG. 8A shows the intracellular analysis of cytokine production by naïve CD4$^+$ T cells as determined by flow cytometry according to an embodiment of a method of the present invention.

FIG. 8B shows IL-10 production by naïve CD4$^+$ T cells as determined by ELISA according to an embodiment of a method of the present invention.

FIG. 8C shows the intracellular analysis of cytokine production by memory CD4$^+$ T cells as determined by flow cytometry according to an embodiment of a method of the present invention.

FIG. 8D shows IL-10 production by memory CD4$^+$ T cells as determined by ELISA according to an embodiment of a method of the present invention.

FIGS. 13A-B show OX40-specific monoclonal antibodies that can inhibit the generation of IL-10 producing cells (Tr1) from CD4$^+$ T cells stimulated by vit D$_3$ (0.1 μM)/Dex (50 nm), CD32L/ICOSL and anti-CD3/CD28 (0.2 μg/ml) according to an embodiment of a method of the present invention. Representative Fluorescence Activated Cell Sorting (FACS) data are shown in A and the percentages of IL-10 producing cells for all OX40 monoclonal antibodies treatments are shown in B.

FIG. 14 shows the results of hOX40-specific monoclonal antibodies that inhibit Tr1 cell generation also stimulate CD4$^+$ T cell proliferation according to an embodiment of a method of the present invention.

FIGS. 15A and 15B details the titration of OX40 monoclonal antibodies for their ability to inhibit the generation of Tr1 cells from CD4$^+$ T cells according to an embodiment of a method of the present invention. Representative FACS data are shown in FIG. 15A and percentage of Tr1 cells after treatment with nine OX40 monoclonal antibodies are shown in FIG. 15B.

FIG. 16C is a monocyte-based proliferation assay showing that two of the antibodies blocked ICOS$^+$Treg function.

FIGS. 17A and 17B shows the identification of anti-hOX40 monoclonal antibodies that inhibit the generation of Tr1 cells and block FOXP3$^+$CD4$^+$CD25$^{high}$ Treg function according to an embodiment of a method of the present invention. Representative flow cytometry analyses are shown in FIG. 17A. Data for six monoclonal antibodies are shown in FIG. 17B.

FIGS. 19A and 19B shows anti-hOX40 agonist antibodies blocking lymphoma-derived CD4$^+$CD25$^{high}$ Treg function according to an embodiment of a method of the present invention. Representative FACS analyses are shown in FIG. 19A and data for all experiments are shown in FIG. 19B.

FIGS. 31A-B show humanized and mouse anti-human OX40 antibodies require cross-linking in order to enhance T cell proliferation.

FIGS. 32A-C show anti-human OX40 antibodies block the activity of CD4+FOXP3+nTregs using plate-bound antibodies.

FIGS. 33A-C show that a high concentration of mouse anti-human OX40 antibodies preferentially kills FOXP3+ Tregs.

FIG. 36 shows the alignment of the amino acid sequences of 106-222, humanized 106-222 (Hu106), and human acceptor X61012 (GenBank accession number) VH sequences are shown. Amino acid residues are shown in single letter code. Numbers above the sequences indicate the locations according to Kabat et al. (Sequences of Proteins of Immunological Interests, Fifth edition, NIH Publication No. 91-3242, U.S. Department of Health and Human Services, 1991). The same sequences as claimed herein are also provided in the Sequence Listing and the position numbers may be different. In FIG. 36, CDR sequences defined by Kabat et al. (1991) are underlined in 106-222 VH. CDR residues in X61012 VH are omitted in the figure. Human VH sequences homologous to the 106-222 VH frameworks were searched for within the GenBank database, and the VH sequence encoded by the human X61012 cDNA (X61012 VH) was chosen as an acceptor for humanization. The CDR sequences of 106-222 VH were first transferred to the corresponding positions of X61012 VH. Next, at framework positions where the three-dimensional model of the 106-222 variable regions suggested significant contact with the CDRs, amino acid residues of mouse 106-222 VH were substituted for the corresponding human residues. These substitutions were performed at positions 46 and 94 (underlined in Hu106 VH). In addition, a human framework residue that was found to be atypical in the corresponding V region subgroup was substituted with the most typical residue to reduce potential immunogenicity. This substitution was performed at position 105 (double-underlined in Hu106 VH).

FIG. 37 shows alignment of the amino acid sequences of 106-222, humanized 106-222 (Hu106), and human acceptor AJ388641 (GenBank accession number) VL sequences is shown. Amino acid residues are shown in single letter code. Numbers above the sequences indicate the locations according to Kabat et al. (1991). The same sequences as claimed herein are also provided in the Sequence Listing although the position numbers may be different. CDR sequences defined by Kabat et al. (1) are underlined in 106-222 VH. CDR residues in AJ388641 VL are omitted in the figure. Human VL sequences homologous to the 106-222 VL frameworks were searched for within the GenBank database, and the VL sequence encoded by the human AJ388641 cDNA (AJ388641 VL) was chosen as an acceptor for humanization. The CDR sequences of 106-222 VL were transferred to the corresponding positions of AJ388641 VL. No framework substitutions were performed in the humanized form.

FIG. 38 shows the nucleotide sequence of the Hu106 VH gene flanked by SpeI and HindIII sites (underlined) is shown along with the deduced amino acid sequence. Amino acid residues are shown in single letter code. The signal peptide sequence is in italic. The N-terminal amino acid residue (Q) of the mature VH is double-underlined. CDR sequences according to the definition of Kabat et al. (1991) are underlined. The same sequences as claimed herein are also provided in the Sequence Listing and the position numbers may be different in the Sequence Listing. The intron sequence is in italic. Hu106 VH gene fragment digested with SpeI and HindIII was cloned between the corresponding sites in the Expression Vector shown in FIG. 23.

FIG. 39 shows the nucleotide sequence of the Hu106-222 VL gene flanked by NheI and EcoRI sites (underlined) is shown along with the deduced amino acid sequence. Amino acid residues are shown in single letter code. The signal peptide sequence is in italic. The N-terminal amino acid residue (D) of the mature VL is double-underlined. CDR sequences according to the definition of Kabat et al. (1991) are underlined. The intron sequence is in italic. Hu106 VL gene fragment digested with NheI and EcoRI was cloned between the corresponding sites in the Expression Vector shown in FIG. 23. The same sequences as claimed herein are also provided in the Sequence Listing although the position numbers may be different in the Sequence Listing.

FIG. 40 shows the alignment of the amino acid sequences of 119-122, humanized 119-122 (Hu119), and human acceptor Z14189 (GenBank accession number) VH sequences are shown. Amino acid residues are shown in single letter code. Numbers above the sequences indicate the locations according to Kabat et al. (Sequences of Proteins of Immunological Interests, Fifth edition, NIH Publication No. 91-3242, U.S. Department of Health and Human Services, 1991). CDR sequences defined by Kabat et al. (1991) are underlined in 119-122 VH. CDR residues in Z14189 VH are omitted in the figure. Human VH sequences homologous to the 119-122 VH frameworks were searched for within the GenBank database, and the VH sequence encoded by the human Z14189 cDNA (Z14189 VH) was chosen as an acceptor for humanization. The CDR sequences of 119-122 VH were first transferred to the corresponding positions of Z14189 VH. Next, at framework positions where the three-dimensional model of the 119-122 variable regions suggested significant contact with the CDRs, amino acid residues of mouse 119-122 VH were substituted for the corresponding human residues. These substitutions were performed at positions 26, 27, 28, 30 and 47 (underlined in the Hu119 VH sequence) as shown on the figure. The same sequences as claimed herein are also provided in the Sequence Listing although the position numbers may be different in the Sequence Listing.

FIG. 41 shows the alignment of the amino acid sequences of 119-122, humanized 119-122 (Hu119), and human acceptor M29469 (GenBank accession number) VL sequences are shown. Amino acid residues are shown in single letter code. Numbers above the sequences indicate the locations according to Kabat et al. (1991). CDR sequences defined by Kabat et al. (1) are underlined in 119-122 VL. CDR residues in M29469 VL are omitted in the sequence. Human VL sequences homologous to the 119-122 VL frameworks were searched for within the GenBank database, and the VL sequence encoded by the human M29469 cDNA (M29469 VL) was chosen as an acceptor for humanization. The CDR sequences of 119-122 VL were transferred to the corresponding positions of M29469 VL. No framework substitutions were needed in the humanized form. The same sequences as claimed herein are also provided in the Sequence Listing although the position numbers may be different in the Sequence Listing.

FIG. 42 shows the nucleotide sequence of the Hu119 VH gene flanked by SpeI and HindIII sites (underlined) is shown along with the deduced amino acid sequence. Amino acid residues are shown in single letter code. The signal peptide sequence is in italic. The N-terminal amino acid residue (E) of the mature VH is double-underlined. CDR sequences according to the definition of Kabat et al. (1991) are underlined. The intron sequence is in italic. Hu119 VH gene fragment digested with SpeI and HindIII was cloned between the corresponding sites in the Expression Vector shown in FIG. 23. The same sequences as claimed herein are also provided in the Sequence Listing although the position numbers may be different in the Sequence Listing.

FIG. 43 shows nucleotide sequence of the Hu119 VL gene flanked by NheI and EcoRI sites (underlined) is shown along with the deduced amino acid sequence. Amino acid residues are shown in single letter code. The signal peptide sequence is in italic. The N-terminal amino acid residue (E) of the mature VL is double-underlined. CDR sequences according to the definition of Kabat et al. (1991) are underlined. The intron sequence is in italic. Hu119 VL gene fragment digested with NheI and EcoRI was cloned between the corresponding sites in the Expression Vector shown in FIG. 23. The same sequences as claimed herein are also provided in the Sequence Listing although the position numbers may be different in the Sequence Listing.

DETAILED DESCRIPTION OF THE INVENTION

Figure 3:
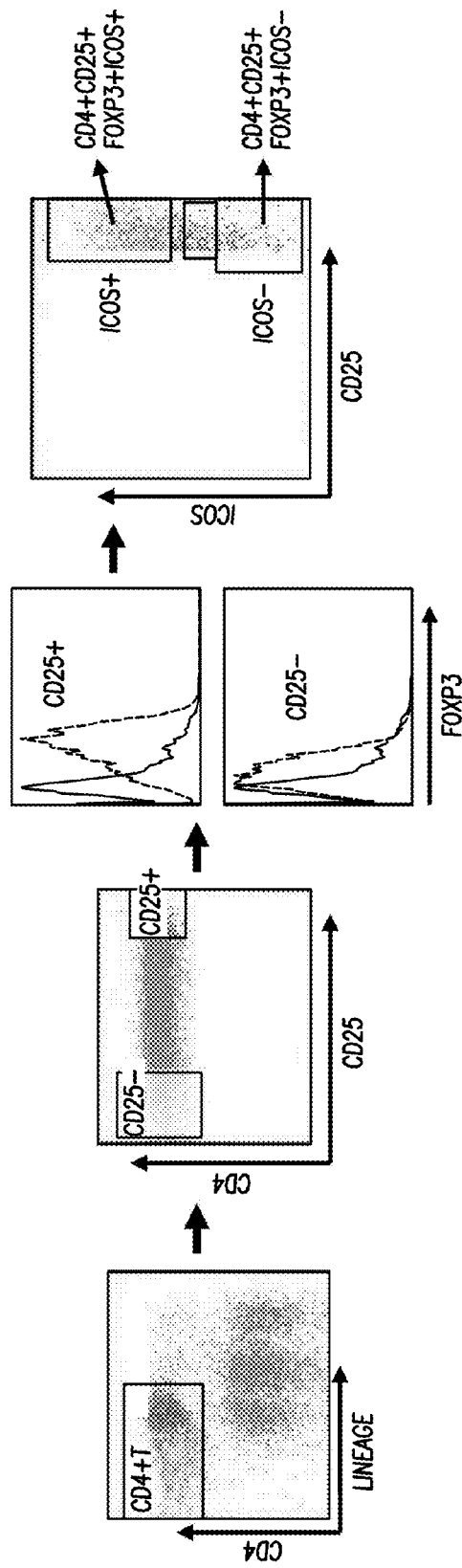
FIG. 3 shows the isolation of ICOS$^+$FOXP3$^+$ or ICOS$^-$FOXP3$^+$ Tregs from FL. Single cell suspension was obtained from a spleen specimen before any treatment. Cells were thawed on the day of assay. Enriched CD4$^+$CD8$^-$CD14$^-$CD16$^-$CD56$^-$CD11c$^-$TCRγδ$^-$ T cells were divided into CD25$^{low}$ and CD25$^{high}$ subsets. CD4$^+$CD25$^{high}$FOXP3$^+$ Tregs were further sorted into ICOS$^{high}$ and ICOS$^{low}$ subsets based on surface expression of ICOS. Intracellular expression of FOXP3 was determined in all subsets.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or "antibody portion") includes fragments of an antibody that retain the ability to specifically bind to an antigen (e.g., hOX40). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Still further, an antibody or antigen-binding portion thereof may be part of a larger immunoadhesion molecules, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101) and use of a cysteine residue, a marker peptide and a C-terminal polyhistidine tag to make bivalent and biotinylated scFv molecules (Kipriyanov, S. M., et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. Preferred antigen binding portions are complete domains or pairs of complete domains.

OX40/OX40-ligand (OX40 Receptor)/(OX40L) are a pair of costimulatory molecules critical for T cell proliferation, survival, cytokine production, and memory cell generation. Early in vitro experiments demonstrated that signaling through OX40 on CD4$^+$ T cells lead to TH2, but not TH1 development. These results were supported by in vivo studies showing that blocking OX40/OX40L interaction prevented the induction and maintenance of TH2-mediated allergic immune responses. However, blocking OX40/OX40L interaction ameliorates or prevents TH1-mediated diseases. Furthermore, administration of soluble OX40L or gene transfer of OX40L into tumors were shown to strongly enhance anti-tumor immunity in mice. Recent studies also suggest that OX40/OX40L may play a role in promoting CD8 T cell-mediated immune responses. As discussed herein, OX40 signaling blocks the inhibitory function of CD4$^+$CD25$^+$ naturally occurring regulatory T cells and the OX40/OX40L pair plays a critical role in the global regulation of peripheral immunity versus tolerance.

The terms "Kabat numbering", "Kabat definitions" and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) Ann. NY Acad. Sci. 190:382-391 and, Kabat, E. A., et al. (1991) Sequences of Proteins of Immunological Interest, Fifth Edition, U.S. Department of Health and Human Services, NIH Publication No. 91-3242).

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor, L. D., et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences (See Kabat, E. A., et al. (1991) Sequences of Proteins of Immunological Interest, Fifth Edition, U.S. Department of Health and Human Services, NIH Publication No. 91-3242).

An "isolated antibody" includes an antibody that is substantially free of other antibodies having different antigenic specificities (e.g., an isolated antibody that specifically binds hOX40 is substantially free of antibodies that specifically bind antigens other than hOX40). An isolated antibody that specifically binds hOX40 may bind OX40 molecules from other species. Moreover, an isolated antibody may be substantially free of other cellular material and/or chemicals.

The term "activity" includes activities such as the binding specificity/affinity of an antibody for an antigen, for example, an anti-human OX40 antibody that binds to an OX40 antigen and/or the activation potency of an antibody, for example, an anti-OX40 antibody whose binding to hOX40 receptor activates the biological activity of hOX40 or activation of receptor binding in a human L/OX40 cell assay.

The term "$K_{off}$", as used herein, is intended to refer to the off rate constant for dissociation of an antibody from the antibody/antigen complex. The term "$K_d$", as used herein, is intended to refer to the dissociation constant of a particular antibody-antigen interaction.

The phrase "surface plasmon resonance" includes an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 5 and Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "monoclonal antibody" (monoclonal antibody) refers to an antibody, or population of like antibodies, obtained from a population of substantially homogeneous antibodies, and is not to be construed as requiring production of the antibody by any particular method, including but not limited to, monoclonal antibodies can be made by the hybridoma method first described by Kohler and Milstein (Nature, 256: 495-497, 1975), or by recombinant DNA methods.

The term "chimeric antibody" (or "chimeric immunoglobulin") refers to a molecule comprising a heavy and/or light chain which is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al. (1984), infra; Morrison et al., Proc. Natl. Acad. Sci. U.S.A. 81:6851).

The term "humanized antibody" refers to forms of antibodies that contain sequences from non-human (eg, murine) antibodies as well as human antibodies. A humanized antibody can include conservative amino acid substitutions or non-natural residues from the same or different species that do not significantly alter its binding and/or biologic activity. Such antibodies are chimeric antibodies that contain minimal sequence derived from non-human immunoglobulins. For the most part, humanized antibodies are human immunoglobulins (recipient antibody) in which residues from a complementary-determining region (CDR) of the recipient are replaced by residues from a CDR of a non-human species (donor antibody) such as mouse, rat, camel, bovine, goat, or rabbit having the desired properties. Furthermore, humanized antibodies can comprise residues that are found neither in the recipient antibody nor in the imported CDR or framework sequences. These modifications are made to further refine and maximize antibody performance. Thus, in general, a humanized antibody will comprise all or substantially all of at least one, and in one aspect two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), or that of a human immunoglobulin (see, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1; Queen et al. (1989) Proc. Natl. Acad. Sci. USA, Vol 86:10029-10033).

Each of the antibodies described and claimed herein may be referred to, in the singular or plural, as: "anti-OX40 antibody;" "anti-hOX40 antibody;" "anti-hOX40 monoclonal antibody;" "anti-human OX40 antibody;" "anti-human OX40 mAb;" "anti-hOX40 mAb" "hOX40 specific monoclonal antibody;" "anti-OX40L antibody;" "anti-hOX40L antibody;" "anti-human OX40L antibody;" "human OX40 specific antibody;" "human OX40 specific monoclonal antibody;" "human OX40 specific antibody;" "anti-human OX40 specific antibody;" "anti-human OX40 specific monoclonal antibody;" "h-OX40 specific antibody;" "h-OX40 specific monoclonal antibody;" "hOX40 agonistic antibody;" "hOX40 antagonist" and/or other similar variations of the same.

As disclosed in U.S. patent application Ser. No. 11/659,266 titled "Methods to Treat Disease States by Influencing the Signaling of OX-40-Receptors and High Throughput Screening Methods and Identifying Substrates Thereof" which is herein incorporated by reference, it was discovered that a function of OX40L is the negative regulation of the generation of Tr1 cells induced by immunosuppressive agents Dex and vit D3, ICOSL, or immature DCs. This discovery demonstrates a general mechanism by which OX40L enhances immunity and breaks immunological tolerance.

Figure 4:
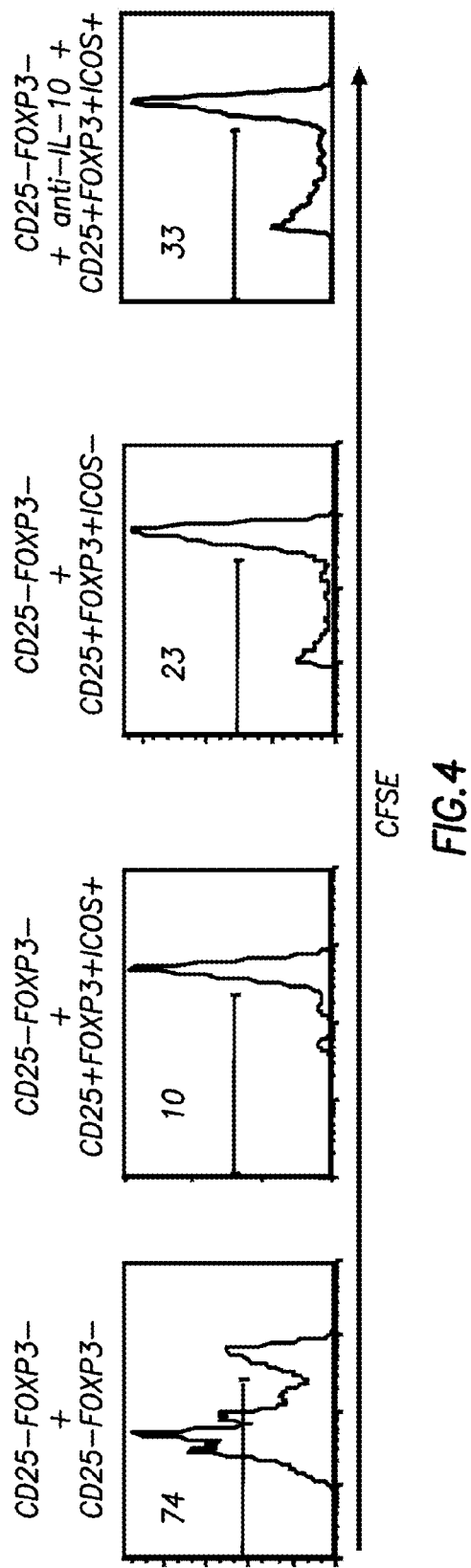
FIG. 4 shows intratumoral Tregs inhibit proliferation of infiltrating CD4$^+$CD25$^-$ T cells in FL, and the inhibition could be partially blocked by anti-IL-10 neutralization antibodies. CFSE-labeled CD4$^+$CD25$^-$ tumor-infiltrating T cells were cultured with autologous tumor cells preactivated by recombinant CD40L in the presence or absence of autologous ICOS$^+$FOXP3$^+$ Tregs or ICOS$^-$FOXP3$^+$ Tregs, or anti-IL-10 (10 μg/ml). After 72 hours of culture, proliferation of CD4$^+$CD25$^-$ cells was determined by flow cytometric analysis of CFSE dilution.

With the use of immunohistologic analysis (FIG. 1), intracellular staining (FIG. 2), and cell sorting (FIG. 3), we have shown that both $ICOS^+IL$-10-producing and ICOS-TGF-$\beta$-producing Tregs infiltrated human FL tissues. These FL-derived $FOXP3^+$ Tregs can strongly inhibit the proliferation of $FOXP3^-CD4^+CD25^-$ tumor-infiltrating T cells in response to $CD40^-$ ligand preactivated autologous lymphoma cells (FIG. 4). The suppressive activity of $ICOS^+$ Tregs could be partially blocked by a neutralizing anti-IL-10 antibody, confirming the role of $ICOS^+IL$-10 producing Tregs in FL (FIG. 4). In the experiment of FIG. 2, tumor cells and PBMCS were obtained from 7 patients with an initial diagnosis before therapy. PBMC's were also obtained from 7 healthy donors for comparison. The percentages of regulatory T cells over total $CD4^+$ T cells were determined by flow cytometric analysis of $CD4^+CD25^+CD127^{low}FOXP3^+$ Tregs. FIG. 2A provides representative FACS analysis of Tregs, while FIG. 2B shows the percentage of Tregs of all donors.

Figure 5A:
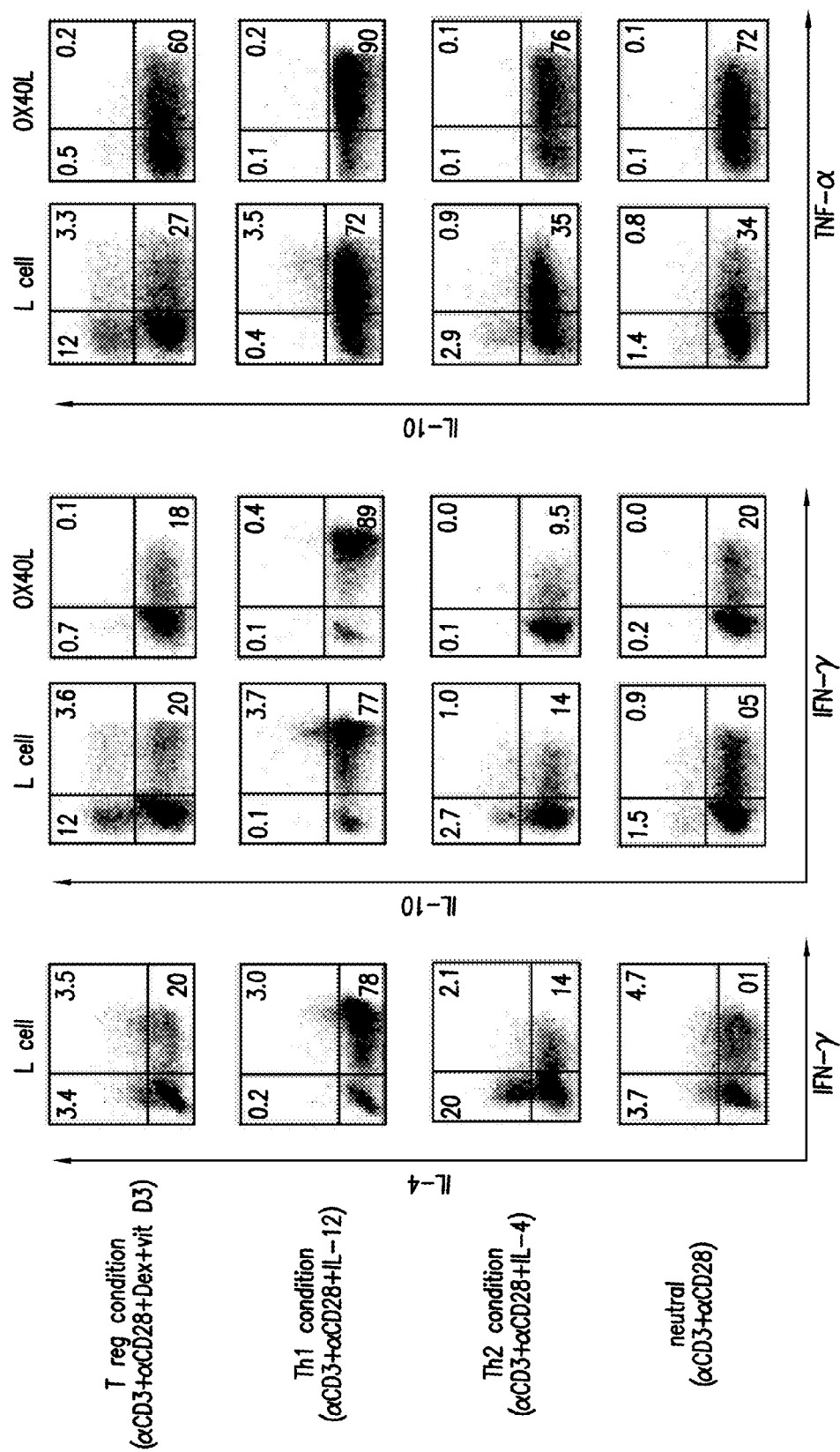
FIG. 5A shows the intracellular analysis of cytokine production by naïve CD4$^+$ T cells as determined by flow cytometry according to an embodiment of a method of the present invention.

It was also discovered that OX40L inhibits the generation of Tr1 cells from $CD4^+$ T cells induced by Dex and vit D3. It is known that a combination of the immunosuppressive drugs Dex and vit D3 consistently induce the differentiation of naïve $CD4^+$ T cells into Tr1 cells. To investigate whether OX40L can inhibit the generation and function of Tr1 cells, naïve $CD4^+$ T cells were cultured with anti-CD3 plus anti-CD28 monoclonal antibodies in the presence or absence of OX40L-transfected L cells in four different culture conditions including: (1) Tr1 (Dex and vit D3); (2) TH1 (IL-12); (3) TH2 (IL-4); or (4) neutral (medium alone) for 7 days (FIG. 5A). IL-10 production by the primed T cells was analyzed by intracellular cytokine staining and ELISA.

In the experiments of FIG. 5A, an intracellular analysis of cytokine production by naïve CD4+ T cells was conducted by flow cytometry. Naïve CD4+ T cells were cultured with anti-CD3 and anti-CD28 monoclonal antibodies in the presence of IL-2 on parental L cells or OX40L-L cells with the indicated recombinant cytokines or reagents for 7 days. Percentages of the respective cytokine-producing T cells are indicated in each dot blot profile. The results show that OX40L inhibits the generation of Tr1 cells from naïve CD4+ T cells induced by the different polarizing signals. As shown in FIG. 5A, between 2% to 4% of Tr1 cells were generated from naïve CD4+ T cells cultured in neutral or TH1 or TH2 conditions. More than 15% of Tr1 cells were generated in culture with Dex plus vit D3. The addition of OX40L completely blocked the generation of Tr 1 cells, while promoting the generation of TNF-α-producing T cells in all culture conditions.

Figure 5B:
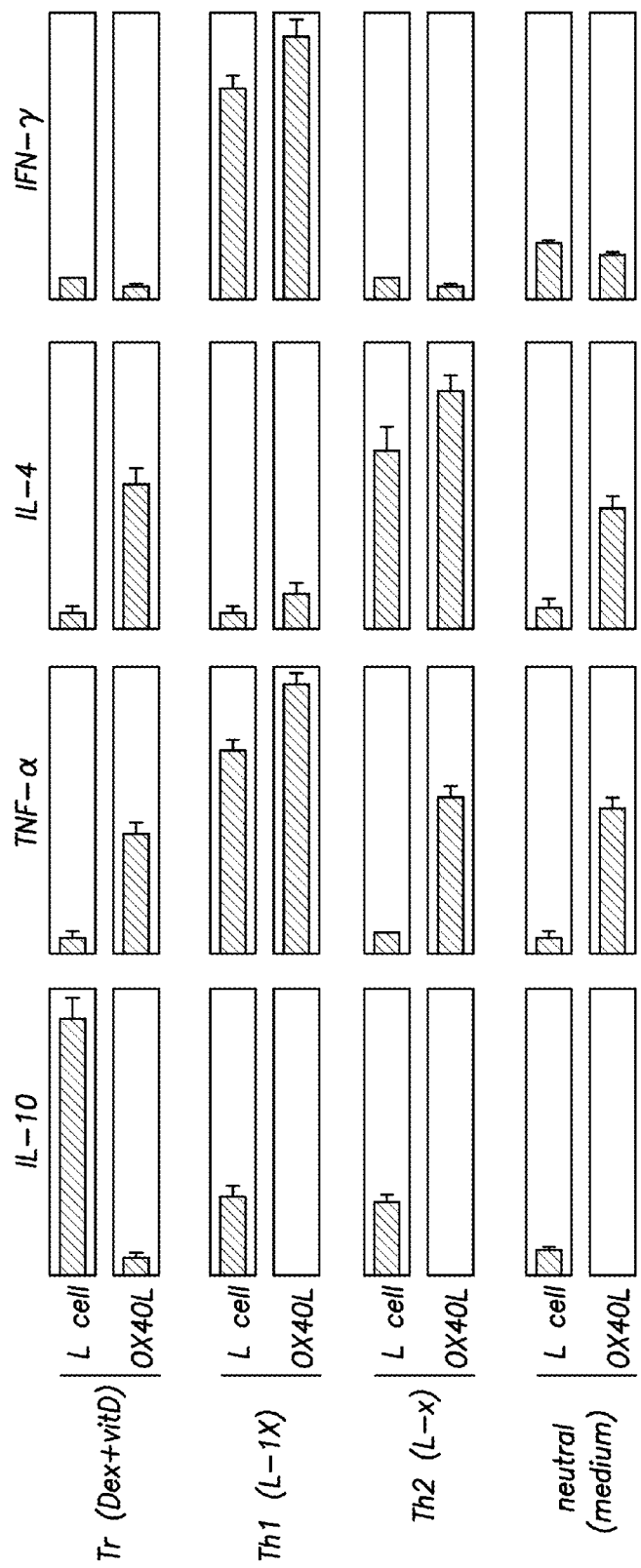
FIG. 5B shows cytokine production by naïve CD4$^+$ T cells as determined by ELISA according to an embodiment of a method of the present invention.

These data were confirmed by ELISA data (FIG. 5B). In the experiments of FIG. 5B, cytokine production by naïve CD4+ cells in supernatants after restimulation with anti-CD3 and anti-CD28 monoclonal antibodies for 24 h was measured by ELISA. Naïve CD4+ T cells were cultured with anti-CD3 and anti-CD28 monoclonal antibodies in the presence of IL-2 on parental L cells or OX40L-L cells with the indicated recombinant cytokines or reagents for 7 days. The data are shown as mean±standard error of the mean (SEM) of four independent experiments. The results show that OX40L inhibits the generation of Tr1 cells from naïve CD4+ T cells induced by the different polarizing signals.

Figure 5C:
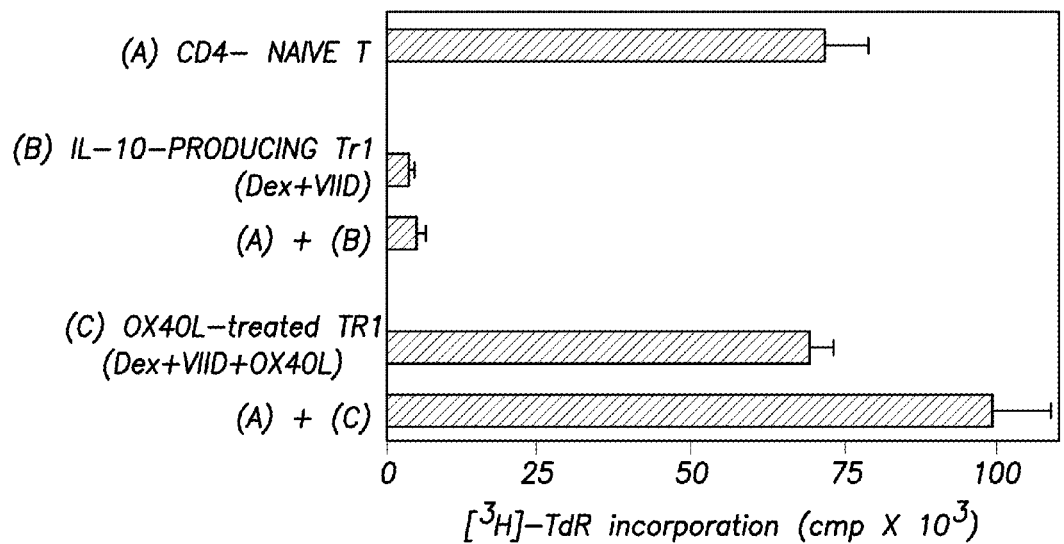
FIG. 5C shows suppressive function by IL-10-producing Tr1 cells as determined by [$^3$H]thymidine incorporation according to an embodiment of a method of the present invention.

Naïve CD4+ T cells primed with Tr1 condition (Dex plus vit D3) were anergic and had the ability to suppress the proliferation of naïve CD4+ T cells in response to anti-CD3 plus anti-CD28 monoclonal antibodies (FIG. 5C). In the experiments of FIG. 5C, suppressive function in T cells was measured by [$^3$H]thymidine incorporation. Mixtures of the indicated T cell populations were restimulated by anti-CD3 and anti-CD28 monoclonal antibodies. Error bars represent SEM of triplicate wells. It was discovered that naïve CD4+ T cells primed with the same Tr1 condition in the presence of OX40L proliferated vigorously and failed to inhibit the proliferation of naïve CD4+ T cells in response to anti-CD3 plus anti-CD28 monoclonal antibodies. The data suggest that OX40L blocks the generation of functional Tr1 cells from naïve CD4+ T cells induced by Dex and vit D3.

It was discovered that Tr1 cells can be generated from memory CD4+CD45RA− CD45RO+ T cells, and that OX40L can inhibit the generation of Tr1 cells from memory CD4+ T cells. Memory CD4+CD45RA−CD45RO+ T cells were cultured for 7 days with anti-CD3 plus anti-CD28 monoclonal antibodies in the presence or absence of OX40L-transfected L cells Tr1 condition (Dex plus vit D3). In the experiments of FIG. 6A, an intracellular analysis of cytokine production by CD4+ memory T cells was conducted by flow cytometry. Memory CD4+CD45RO+CD25− memory T cells were cultured with anti-CD3, anti-CD28 monoclonal antibodies, and IL-2 on parental L cells or OX40L-L cells in the presence or absence of Dex plus vit D3 for 7 days. Percentages of the respective cytokine-producing T cells are indicated in each dot blot profile. The results show that OX40L inhibits the generation of Tr1 cells from memory CD4+ T cells under a condition with Dex plus vit D3. FIG. 6A shows that large numbers of Tr1 cells (>20%) were generated from CD4+ memory T cells in culture with Dex plus vit D3. The addition of OX40L completely blocked the generation of Tr1 cells and promoted generation of TNF-α-producing cells from memory CD4+ T cells.

Figure 6B:
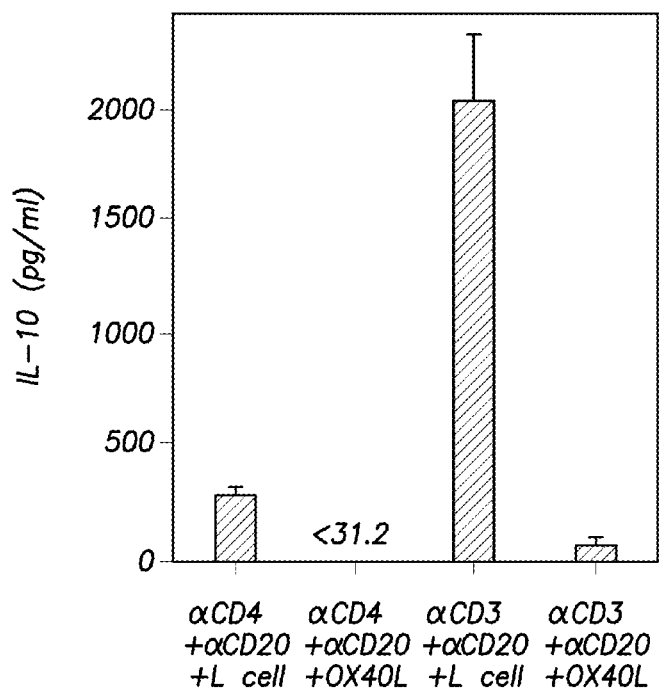
FIG. 6B shows IL-10 production by memory CD4$^+$ T cells as determined by ELISA according to an embodiment of a method of the present invention.
Figure 6A:
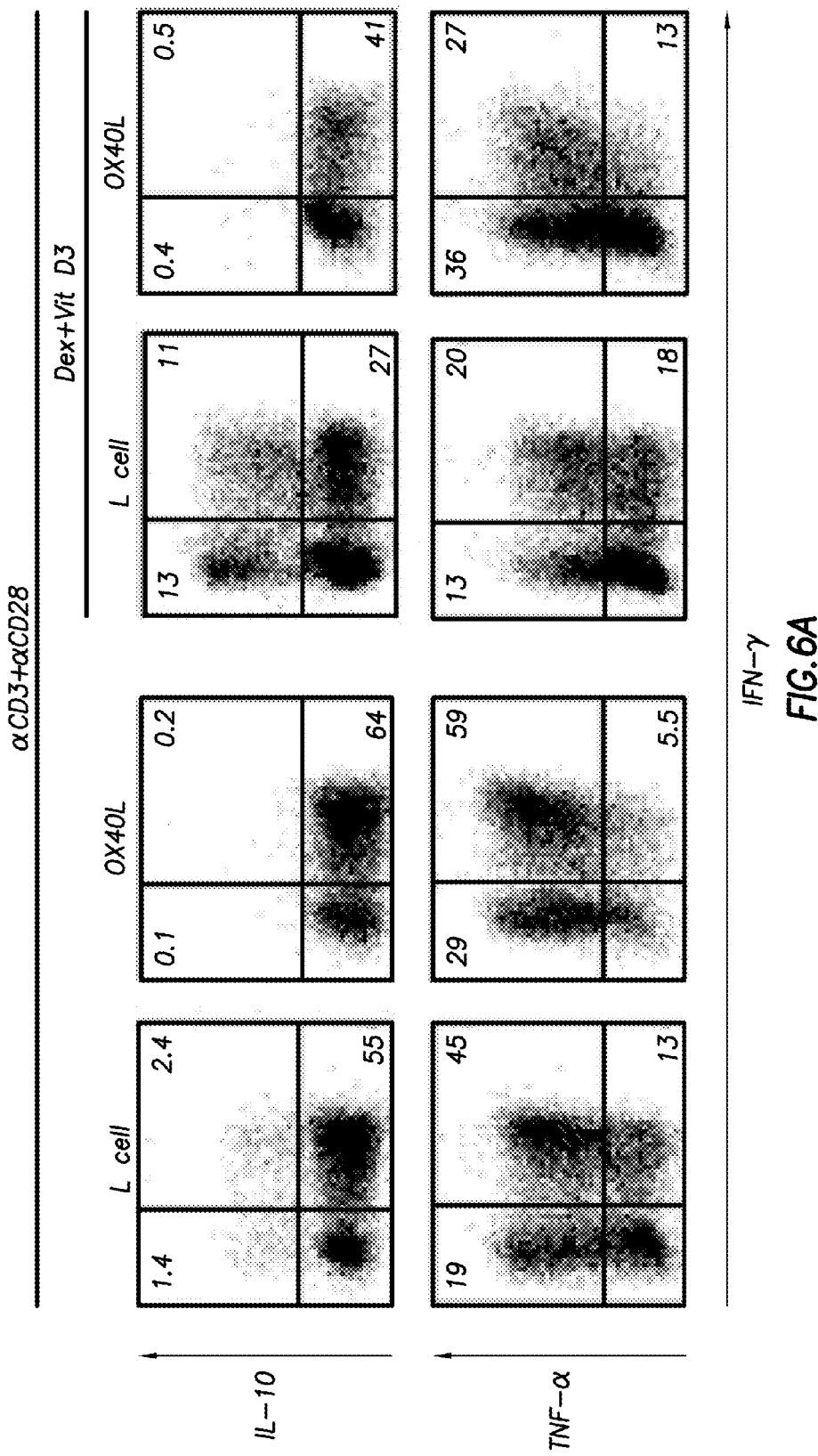
FIG. 6A shows the intracellular analysis of cytokine production by memory CD4$^+$ T cells as determined by flow cytometry according to an embodiment of a method of the present invention.

The ability of Dex plus vit D3 to promote IL-10 production from memory CD4+ T cells, and that this ability can be inhibited by OX40L, were confirmed by IL-10 ELISA analyses (FIG. 6B). In the experiments of FIG. 6B, IL-10 production by memory CD4+ T cells was measured in supernatants after restimulation with anti-CD3 and anti-CD28 monoclonal antibodies for 24 h by ELISA. The data are shown as mean±SEM of four independent experiments. The results show that OX40L inhibits the generation of Tr1 cells from memory CD4+ T cells under a condition with Dex plus vit D3.

It was further discovered that OX40L inhibits the generation of Tr1 cells, while other TNF-family members (GITRL and 4-1BBL) do not. Within the TNF-superfamily, OX40L, glucocorticoid-induced TNF receptor-ligand (GITRL), and 4-1BB-ligand (4-1BBL) have costimulatory function for T cells. To investigate whether OX40L was unique in the inhibition of Tr1 cells, naïve CD4+ T cells were cultured with anti-CD3 plus anti-CD28 monoclonal antibodies with Dex plus vit D3, with parental L cells or L cells transfected with OX40L, GITRL, or 4-1BBL for 7 days. While OX40L, GITRL, and 4-1BBL all promoted the generation of TNF-α-producing cells, only OX40L inhibited the generation of Tr1 cells (FIGS. 7A and 7B).

In the experiments of FIG. 7A, an intracellular analysis of cytokine production by naïve CD4+ T cells was conducted by flow cytometry. Naïve CD4+ T cells were cultured with anti-CD3, anti-CD28 monoclonal antibodies, and IL-2 on parental L cells, OX40L-L cells, GITRL-L cells, or 4-1BBL-L cells in the presence of Dex plus vit D3 for 7 days. Percentages of the respective cytokine-producing T cells are indicated in each dot blot profile. The results show that OX40L but not GITRL nor 4-1BBL inhibits the generation of Tr1 cells.

In the experiments of FIG. 7B, IL-10 by naïve CD4+ cells was measured in supernatants after restimulation with anti-CD3 and anti-CD28 monoclonal antibodies for 24 h by ELISA. The data are shown as mean±SEM of four independent experiments. The results show that OX40L but not GITRL nor 4-1BBL inhibits the generation of Tr1 cells.

OX40L, GITRL, and 4-1BBL all promoted the expansion of total T cell numbers (FIG. 7C). In the experiments of FIG. 7C, the number of viable T cells was counted. The data are shown as mean±SEM of four independent experiments.

As understood by those of skill in the art, the results of FIGS. 7A, 7B, and 7C show that OX40L, but not GITRL nor 4-1BBL, inhibits the generation of Tr1 cells. These data suggest that among the three members of TNF-superfamily known to costimulate T cells, OX40L has a novel and unique function in inhibiting the generation of Tr1 cells.

It was further discovered that OX40L inhibits the generation of Tr1 cells induced by ICOSL or immature DCs. ICOS and CD28 represent the two positive costimulatory receptors within the CD28 family expressed on T cells. Signaling through ICOS by agonistic antibodies or ICOSL has been shown to promote CD4+ T cells to produce IL-10. To investigate whether OX40L can inhibit the ability of ICOS to induce IL-10 production by CD4+ T cells, naïve and memory CD4+ T cells were cultured with anti-CD3 in the presence of ICOSL-transfected L cells, or ICOSL-transfected L cells in the presence of OX40L for 7 days.

In the experiments of FIG. 8A, an intracellular analysis of cytokine production by naïve CD4+ T cells was conducted by flow cytometry. Naïve CD4+ T cells were cultured for 7 days on parental L cells, on a mixture of ICOSL-L cells and L cells, or on a mixture of ICOSL-L cells and OX40L-L cells, which were pre-coated with anti-CD3 monoclonal antibody. Percentages of the respective cytokine-producing T cells are indicated in each dot blot profile. The results show that OX40L inhibits the generation of Tr1 cells from naïve CD4+ T cells induced by ICOSL.

In the experiments of FIG. 8B, IL-10 production by naïve CD4+ cells was measured in supernatants after restimulation with anti-CD3 and anti-CD28 monoclonal antibodies for 24 h was measured by ELISA. Naïve CD4+ T cells were cultured for 7 days on parental L cells, on a mixture of ICOSL-L cells and L cells, or on a mixture of ICOSL-L cells and OX40L-L cells, which were pre-coated with anti-CD3 monoclonal antibody. The data are shown as mean±SEM of three independent experiments. The results show that OX40L inhibits the generation of Tr1 cells from naïve CD4+ T cells induced by ICOSL.

In the experiments of FIG. 8C, an intracellular analysis of cytokine production by memory CD4+ T cells was conducted by flow cytometry. Memory CD4+ T cells were cultured for 7 days on parental L cells, on a mixture of ICOSL-L cells and L cells, or on a mixture of ICOSL-L cells and OX40L-L cells, which were pre-coated with anti-CD3 monoclonal antibody. Percentages of the respective cytokine-producing T cells are indicated in each dot blot profile. The results show that OX40L inhibits the generation of Tr1 cells from memory CD4+ T cells induced by ICOSL.

In the experiments of FIG. 8D, IL-10 production by memory CD4+ T cells in supernatants after restimulation with anti-CD3 and anti-CD28 monoclonal antibodies for 24 h was measured by ELISA. Memory CD4+ T cells were cultured for 7 days on parental L cells, on a mixture of ICOSL-L cells and L cells, or on a mixture of ICOSL-L cells and OX40L-L cells, which were pre-coated with anti-CD3 monoclonal antibody. The data are shown as mean±SEM of three independent experiments. The results show that OX40L inhibits the generation of Tr1 cells from memory CD4+ T cells induced by ICOSL.

The results of the experiments of FIGS. 8A, 8B, 8C, and 8D show that ICOSL significantly promoted the generation of Tr1 cells from both naïve and memory CD4+ T cells. The addition of OX40L completely inhibited the generation of Tr1 cells from both naïve and memory CD4+ T cells, while strongly promoting the generation of cells producing TNF-α.

Figure 8E:
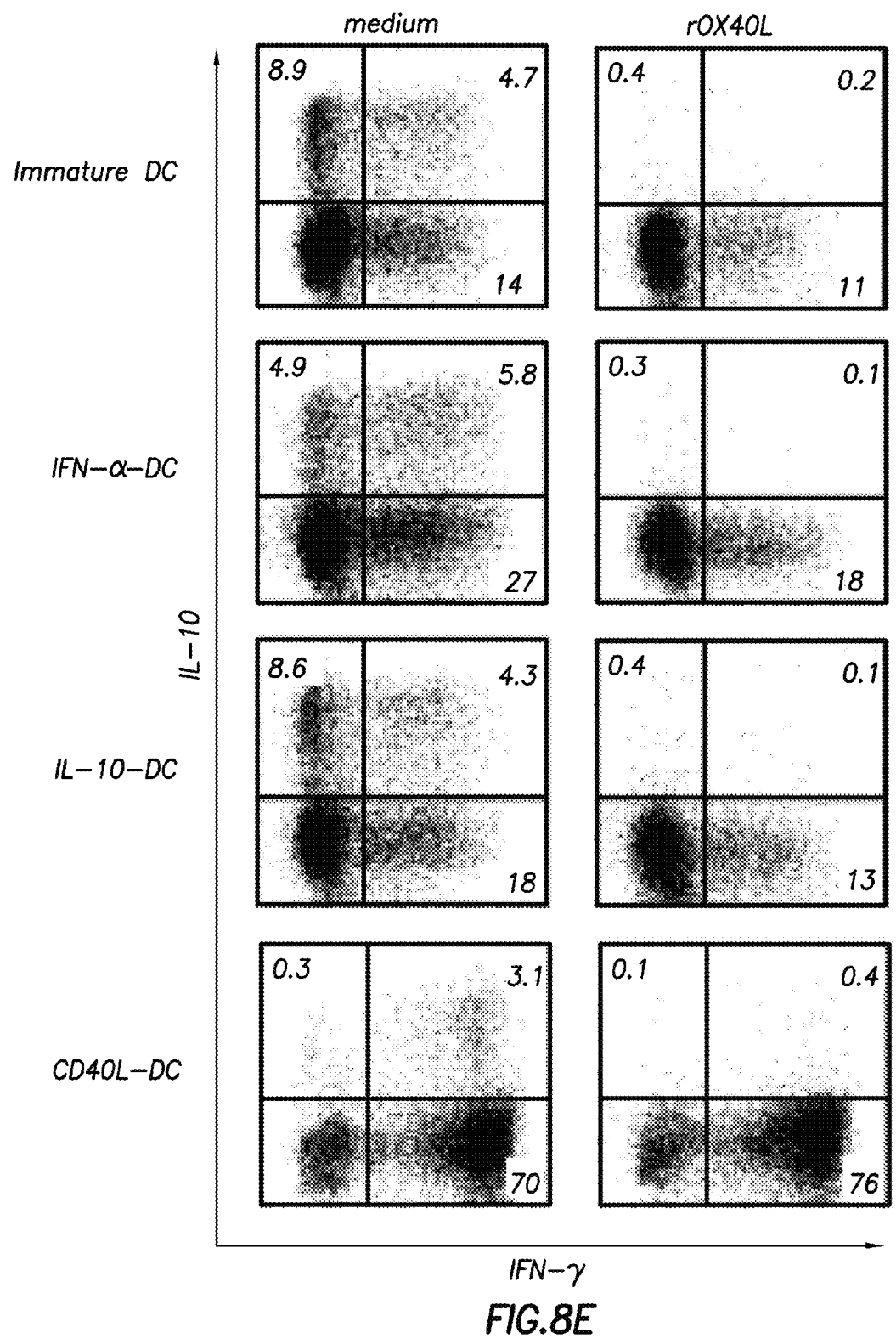
FIG. 8E shows the intracellular analysis of cytokine production by naïve CD4$^+$ T cells as determined by flow cytometry according to an embodiment of a method of the present invention.
Figure 8F:
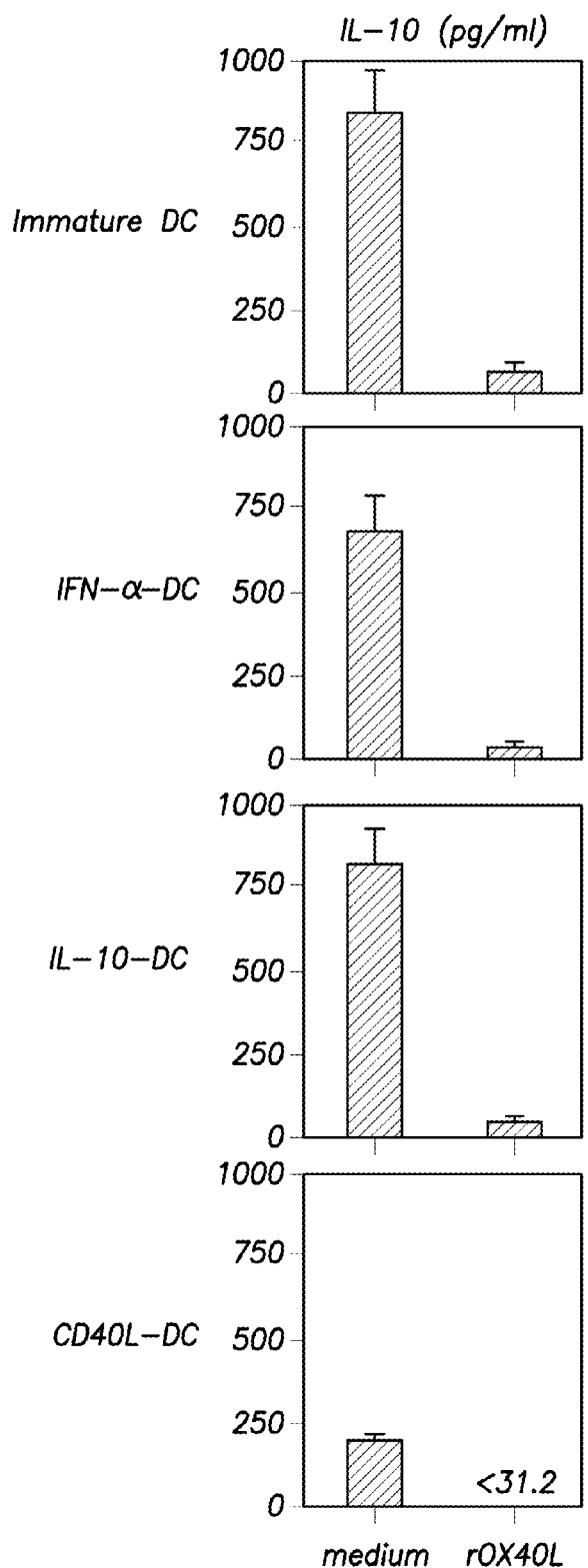
FIG. 8F shows IL-10 production by naïve CD4$^+$ T cells as determined by ELISA according to an embodiment of a method of the present invention.

It is known that immature DCs or DCs treated with IFN-α or IL-10 can induce naïve CD4+ T cells to differentiate into Tr1 cells. It was investigated whether OX40L could inhibit the generation of Tr1 cells induced by DCs. As shown in FIG. 8E, immature DCs or DCs treated with IL-10 or IFN-α all induced the generation of more than 10% of Tr1 cells from naïve CD4+ T cells. By contrast, DCs activated by CD40L induce a strong TH1 response, accompanied by the generation of about 3% Tr1 cells. Addition of recombinant OX40L in DC-T cell cultures completely inhibited the generation of Tr1 cells induced by immature DCs and DCs treated with IL-10 and IFN-α. In addition, OX40L also inhibited the generation of the residual number of Tr1 cells induced by the CD40L activated mature DCs. In the experiments of FIG. 8E, an intracellular analysis of cytokine production by CD4+ naïve T cells was conducted by flow cytometry. Naïve CD4+ T cells were cocultured in the presence or absence of soluble recombinant OX40L for 7 days with immature DCs or DCs cultured with IFN-α, IL-10, and CD40L. Percentages of the respective cytokine-producing T cells are indicated in each dot blot profile. The results show that OX40L inhibits the generation of Tr1 cells from CD4+ T cells induced by DCs The ability of OX40L to inhibit the generation of Tr1 cells induced by DCs was confirmed by ELISA data (FIG. 8F). In the experiments of FIG. 8F, IL-10 production by naïve CD4+ cells was measured in supernatants after restimulation with anti-CD3 and anti-CD28 monoclonal antibodies for 24 h by ELISA. Naïve CD4+ T cells were cocultured in the presence or absence of soluble recombinant OX40L for 7 days with immature DCs or DCs cultured with IFN-α, IL-10, and CD40L. The data are shown as mean±SEM of three independent experiments. The results show that OX40L inhibits the generation of Tr1 cells from CD4+ T cells induced by DCs. Thus, these data demonstrate that OX40L could inhibit the generation of Tr1 cells induced by more physiological signals provided by ICOSL and DCs.

Figure 9:
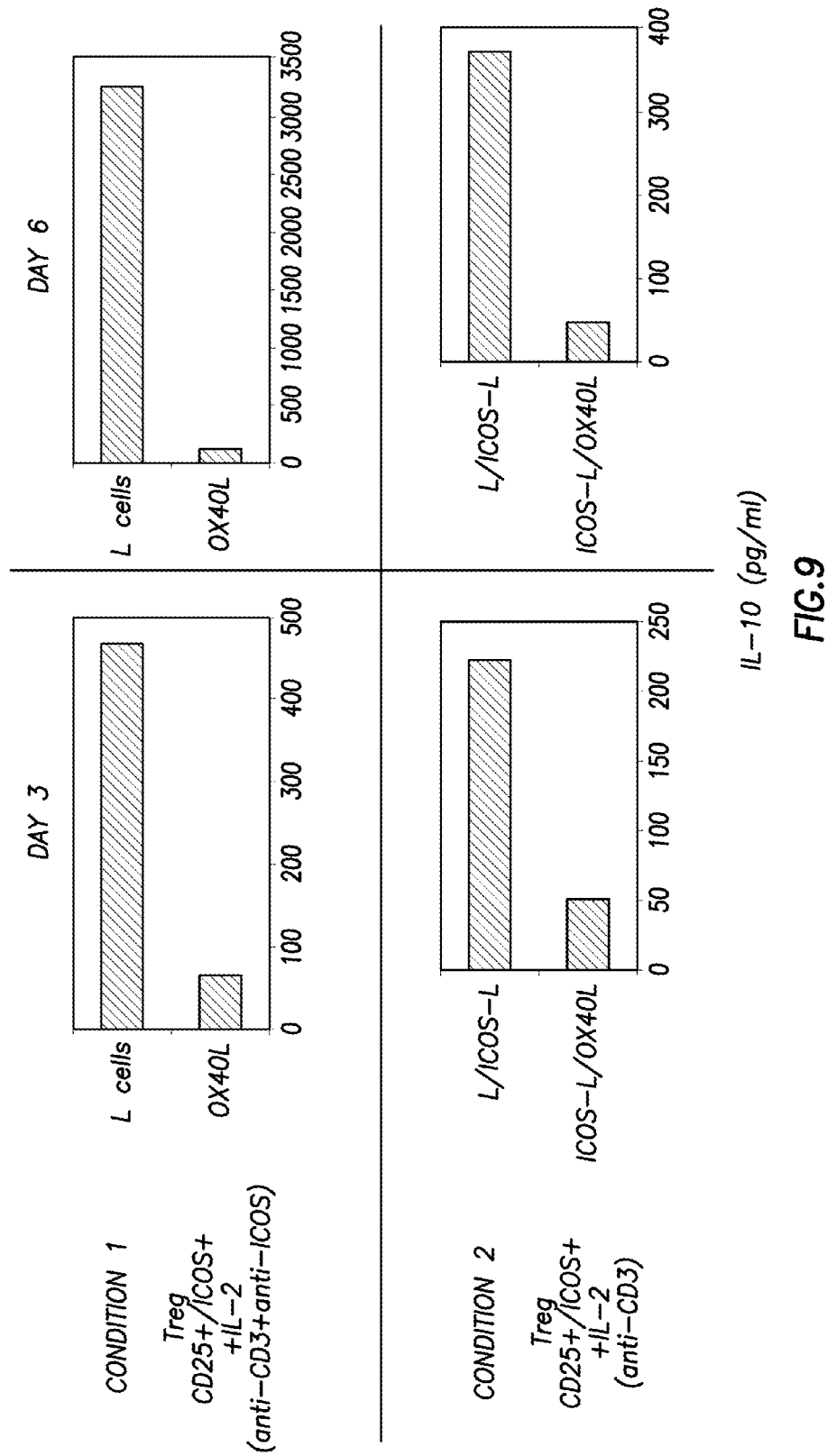
FIG. 9 shows IL-10 production by regulatory T cells as determined by ELISA according to an embodiment of a method of the present invention.

It has been previously suggested that regulatory T cells are highly represented in the area of B cell non-Hodgkin's lymphoma and that B cells are involved in the recruitment of regulatory T cells into the area of the lymphoma. It was investigated whether influencing the signaling of OX40-receptors, such as by OX40L, could provide a therapy against B cell lymphoma. Cryopreserved samples from B cell lymphoma patients were used to estimate the ability of OX40L to shut down Tr1 cells. The samples used were follicular lymphoma obtained from a spleen specimen prior to any treatment. The cells were thawed, with 400×10$^6$ frozen cells yielding 127×10$^6$ live cells and 33.9×10$^6$ dead cells (79% viability). A sufficient number of CD25+ cells were identified by FACS staining. In the experiments of FIG. 9, IL-10 secretion of ICOS+IL-10 producing Tregs was determined by ELISA. Treg cells were cultured under two different conditions. In condition 1, CD25+/ICOS+ cells were cultured with anti-CD3 in the presence of IL-2 (900 μl/ml) on parental L cells or OX40L-L cells with anti-ICOS antibody for 3-6 days. In condition 2, CD25+/ICOS+ cells were cultured with anti-CD3 in the presence of IL-2 (900 μl/ml) on ICOS-L-L cells or a mixture of OX40L-L can ICOS-L-L cells for 3 to 6 days. Cytokine production in the supernatants was measured by ELISA. The results show that OX40L greatly inhibited IL-10 production by Treg cells.

The findings, that OX40L has the capacity to inhibit the generation and function of Tr1 cells induced by the immunosuppressive drugs Dex plus vit D3, ICOSL, or DCs, highlights a novel mechanism by which OX40L promotes immunity and breaks tolerance during different forms of CD4- or CD8-mediated immune responses, as would be understood by one of skill in the art. The ability of OX40L to inhibit the generation of Tr1 cells during both IL-12 induced TH1 or IL-4 induced TH2 responses suggest that OX40L may control the magnitude of TH1- or TH2-mediated immune responses. Furthermore, the ability of OX40L to inhibit the generation of Tr1 cells appears to be a unique property of OX40L, because the two other TNF-family members GITRL and 4-1BBL do not have this functional property. Moreover, the ability of OX40L to inhibit IL-10 production by Treg cells identifies OX40L as a potent treatment for B cell lymphoma and other cancers.

Many molecules have been identified that promote the generation of Tr1 cells, including IL-10, IFN-α, ICOSL, and immunosuppressive compounds such as Dex plus vit D3. OX40L represents a potent inhibitor for the generation of Tr1 cells not only from naïve CD4+ T cells, but also from memory CD4+ T cells and regulatory T cells. This novel property of OX40/OX40L may explain a recent report showing that OX40 signaling allows anergic autoreactive T cells to acquire effector cell functions. Targeting OX40/OX40L thus provides for treatments for human allergic and autoimmune diseases and as well as for the development of treatments for human infectious diseases and cancer including but not limited to melanoma, brain cancer, bone cancer, a leukemia, a lymphoma, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreatic cancer, ovary cancer, cervical cancer, lung cancer, breast cancer and skin cancer, such as squamous cell and basal cell cancers, prostate cancer, renal cell carcinoma, and other known cancers.

Disorders or conditions that can be prevented or treated by antibodies and methods described herein include the prevention or treatment of cancer, such as cutaneous T-cell leukemia, head and neck tumors, pancreatic cancer, bladder cancer, high grade gliomas, brain metastasis, melanoma, skin cancer, lung cancer, breast cancer, prostate cancer, colon cancer, leukemia, myelodysplastic syndrome (a pre-leukemia condition), and multiple myeloma. In general, metastasis of any cancer can be prevented or treated with the compounds and methods described herein. The antibodies may also be used to prevent or treat proliferative angiogenic conditions including telangectasia, venous angiomas, hemangioblastoma. Other disorders, diseases or conditions include viral diseases, some of which may traditionally considered "untreatable." The antibodies, for example, may also be used to classify strains of a single pathogen. Researchers can use the antibodies described herein to identify and to trace specific cells or molecules in an organism.

Generally, the terms "cancer" and "cancerous" refer to or describe the physiological condition in mammals that is typically characterized by unregulated cell growth. More specifically, cancers which can be treated or prevented using any one or more of the antibodies described herein or a variant thereof, include, but are not limited to, carcinoma, lymphoma, blastoma, sarcoma, and leukemia. More particular examples of such cancers include, but are not limited to, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, melanoma, superficial spreading melanoma, lentigo maligna melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

Methods for treating or preventing an immune disorder are also provided herein. These methods comprising administering an effective amount of the antibody to a subject in need of such treatment. In some embodiments, the immune disorder is an immune disorder or an autoimmune disorder. The disorder is asthma, atopic dermatitis, allergic rhinitis, inflammatory bowel disease, multiple sclerosis, GVHD, and/or systemic lupus erythematosus. In some embodiments, the disorder is a disease associated with virus, bacteria or other infectious agent.

Moreover, the antibodies and methods that are described herein can be used to prevent or treat inflammatory diseases and conditions, such as osteoarthritis, Rheumatoid arthritis, Crohn's disease, ulcerative colitis, and auto-immune diseases such as lupus and mixed auto-immune disease. For example, the antibodies described herein may be useful in treating a variety of autoimmune and inflammatory disease comprising the step of administering a therapeutically effective amount of the antibody to a subject in need thereof, wherein the autoimmune disease or inflammatory disease is any one or more of the following diseases: insulin-dependent diabetes mellitus (IDDM), diabetes mellitus, multiple sclerosis, experimental autoimmune encephalomyelitis, acute disseminated encephalomyelitis, arthritis, rheumatoid arthritis, experimental autoimmune arthritis, myasthenia gravis, thyroiditis, Hashimoto's disease, primary myxedema, thyrotoxicosis, pernicious anemia, autoimmune atrophic gastritis, Addison's disease, premature menopause, male infertility, juvenile diabetes, Goodpasture's syndrome, *pemphigus vulgaris*, pemphigoid, sympathetic ophthalmia, phacogenic uveitis, autoimmune haemolyticanaemia, idiopathic leucophenia, primary biliary cirrhosis, active chronic hepatitis $Hb_{s-ve}$, cryptogenic cirrhosis, ulcerative colitis, Sjogren's syndrome, scleroderma, Wegener's granulomatosis, Poly/Dermatomyositis, discoid LE, systemic Lupus erythematosus, Chron's disease, psoriasis, Ankylosingspondylitisis, Antiphospholipid antibody syndrome, Aplastic anemia, Autoimmune hepatitis, Coeliac disease, Graves' disease, Guillain-Barre syndrome (GBS), Idiopathic thrombocytopenic purpura, Opsoclonus myoclonus syndrome (OMS), Optic neuritis, ORd's thyroiditis, *Pemphigus*, Polyarthritis, Primary biliary cirrhosis, Reiter's syndrome, Takayasu's, Temporal arteritis, Warm autoimmune hemolytic anemia, Wegener's granulomatosis, Alopecia universalis, Behcet's disease, Chagas' disease, Chronic fatigue syndrome, Dysautonomia, Endometriosis, Hidradenitis suppurativa, Interstitial cystitis, Neuromyotonia, Sarcoidosis, Scleroderma, Ulcerative colitis, Vitiligo, Vulvodynia, inflammatory skin diseases, allergic contact dermatitis, *H. pylory* gastritis, chronic nasal inflammatory disease, arteriosclerosis and graft versus host disease.

More specifically, an "autoimmune disease" as referred herein is a disease or disorder arising from and directed against an individual's own tissues or organs or a co-segregate or manifestation thereof or resulting condition there from. Autoimmune disease may refer to a condition that results from, or is aggravated by, the production by B cells of antibodies that are reactive with normal body tissues and antigens. Also, an autoimmune disease is one that may involve the secretion of an autoantibody that is specific for an epitope from a self antigen (e.g. a nuclear antigen).

Autoimmune diseases or disorders that are treatable and/or preventable by any one or more of the antibodies described herein include, but are not limited to, arthritis (rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, atopy including atopic diseases such as hay fever and Job's syndrome, dermatitis including contact dermatitis, chronic contact dermatitis, exfoliative dermatitis, allergic dermatitis, allergic contact dermatitis, dermatitis herpetiformis, nummular dermatitis, seborrheic dermatitis, non-specific dermatitis, primary irritant contact dermatitis, and atopic dermatitis, x-linked hyper IgM syndrome, allergic intraocular inflammatory diseases, urticaria such as chronic allergic urticaria and chronic idiopathic urticaria, including chronic autoimmune urticaria, myositis, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, ataxic sclerosis, neuromyelitis optica (NMO), inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), bowel inflammation, pyoderma gangrenosum, erythema nodosum, primary sclerosing cholangitis, respiratory distress syndrome, including adult or acute respiratory distress syndrome (ARDS), meningitis, inflammation of all or part of the uvea, iritis, choroiditis, an autoimmune hematological disorder, rheumatoid spondylitis, rheumatoid synovitis, hereditary angioedema, cranial nerve damage as in meningitis, herpes gestationis, pemphigoid gestationis, pruritis scroti, autoimmune premature ovarian failure, sudden hearing loss due to an autoimmune condition, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, proliferative nephritis, autoimmune polyglandular endocrine failure, balanitis including balanitis circumscripta plasmacellularis, balanoposthitis, erythema annulare centrifugum, erythema dyschromicum perstans, eythema multiform, granuloma annulare, lichen nitidus, lichen sclerosus et atrophicus, lichen simplex chronicus, lichen spinulosus, lichen planus, lamellar ichthyosis, epidermolytic hyperkeratosis, premalignant keratosis, pyoderma gangrenosum, allergic conditions and responses, allergic reaction, eczema including allergic or atopic eczema, asteatotic eczema, dyshidrotic eczema, and vesicular palmoplantar eczema, asthma such as asthma bronchiale, bronchial asthma, and autoimmune asthma, conditions involving infiltration of T cells and chronic inflammatory responses, immune reactions against foreign antigens such as fetal A-B-O blood groups during pregnancy, chronic pulmonary inflammatory disease, autoimmune myocarditis, leukocyte adhesion deficiency, lupus, including lupus nephritis, lupus cerebritis, pediatric lupus, non-renal lupus, extra-renal lupus, discoid lupus and discoid lupus erythematosus, alopecia lupus, systemic lupus erythematosus (SLE) such as cutaneous SLE or subacute cutaneous SLE, neonatal lupus syndrome (NLE), and lupus erythematosus disseminatus, juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, diabetic retinopathy, diabetic nephropathy, diabetic large-artery disorder, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis, large-vessel vasculitis (including polymyalgia rheumatica and giant-cell (Takayasu's) arteritis), medium-vessel vasculitis (including Kawasaki's disease and polyarteritis nodosa/periarteritis nodosa), microscopic polyarteritis, immunovasculitis, CNS vasculitis, cutaneous vasculitis, hypersensitivity vasculitis, necrotizing vasculitis such as systemic necrotizing vasculitis, and ANCA-associated vasculitis, such as Churg-Strauss vasculitis or syndrome (CSS) and ANCA-associated small-vessel vasculitis, temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, Alzheimer's disease, Parkinson's disease, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Behcet's disease/syndrome, Castleman's syndrome, Goodpasture's syndrome, Reynaud's syndrome, Sjogren's syndrome, Stevens-Johnson syndrome, pemphigoid such as pemphigoid bullous and skin pemphigoid, *pemphigus* (including *pemphigus vulgaris, pemphigus foliaceus, pemphigus* mucus-membrane pemphigoid, and *pemphigus erythematosus*), autoimmune polyendocrinopathies, Reiter's disease or syndrome, thermal injury, preeclampsia, an immune complex disorder such as immune complex nephritis, antibody-mediated nephritis, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP), post-transfusion purpura (PTP), heparin-induced thrombocytopenia, and autoimmune or immune-mediated thrombocytopenia such as idiopathic thrombocytopenic purpura (ITP) including chronic or acute ITP, scleritis such as idiopathic cerato-scleritis, episcleritis, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant-cell hepatitis, chronic active hepatitis or autoimmune chronic active hepatitis, lymphoid interstitial pneumonitis (LIP), bronchiolitis obliterans (non-transplant) vs NSIP, Guillain-Barre syndrome, Berger's disease (IgA nephropathy), idiopathic IgA nephropathy, linear IgA dermatosis, acute febrile neutrophilic dermatosis, subcorneal pustular dermatosis, transient acantholytic dermatosis, cirrhosis such as primary biliary cirrhosis and pneumonocirrhosis, autoimmune enteropathy syndrome, Celiac or Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, polychondritis such as refractory or relapsed or relapsing polychondritis, pulmonary alveolar proteinosis, Cogan's syndrome/nonsyphilitic interstitial keratitis, Bell's palsy, Sweet's disease/syndrome, rosacea autoimmune, zoster-associated pain, amyloidosis, a non-cancerous lymphocytosis, a primary lymphocytosis, which includes monoclonal B cell lymphocytosis (e.g., benign monoclonal gammopathy and monoclonal gammopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal or segmental or focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases and chronic inflammatory demyelinating polyneuropathy, Dressler's syndrome, alopecia greata, alopecia totalis, CREST syndrome (calcinosis, Raynaud's phenomenon, esophageal dysmotility, sclerodactyly, and telangiectasia), male and female autoimmune infertility, e.g., due to anti-spermatozoan antibodies, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, parasitic diseases such as leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, pulmonary fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis (acute or chronic), or Fuch's cyclitis, Henoch-Schonlein purpura, human immunodeficiency virus (HIV) infection, SCID, acquired immune deficiency syndrome (AIDS), echovirus infection, sepsis, endotoxemia, pancreatitis, thyroxicosis, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant-cell polymyalgia, chronic hypersensitivity pneumonitis, keratoconjunctivitis sicca, epidemic keratoconjunctivitis, idiopathic nephritic syndrome, minimal change nephropathy, benign familial and ischemia-reperfusion injury, transplant organ reperfusion, retinal autoimmunity, joint inflammation, bronchitis, chronic obstructive airway/pulmonary disease, silicosis, aphthae, aphthous stomatitis, arteriosclerotic disorders, asperniogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, non-malignant thymoma, vitiligo, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, autoimmune polyglandular syndrome type I, adult-onset idiopathic hypoparathyroidism (AOIH), cardiomyopathy such as dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia syndrome, angiectasis, autoimmune disorders associated with collagen disease, rheumatism, neurological disease, lymphadenitis, reduction in blood pressure response, vascular dysfunction, tissue injury, cardiovascular ischemia, hyperalgesia, renal ischemia, cerebral ischemia, and disease accompanying vascularization, allergic hypersensitivity disorders, glomerulonephritides, reperfusion injury, ischemic re-perfusion disorder, reperfusion injury of myocardial or other tissues, lymphomatous tracheobronchitis, inflammatory dermatoses, dermatoses with acute inflammatory components, multiple organ failure, bullous diseases, renal cortical necrosis, acute purulent meningitis or other central nervous system inflammatory disorders, ocular and orbital inflammatory disorders, granulocyte transfusion-associated syndromes, cytokine-induced toxicity, narcolepsy, acute serious inflammation, chronic intractable inflammation, pyelitis, endarterial hyperplasia, peptic ulcer, valvulitis, and endometriosis.

The antibodies described herein may have a variety of academic, medical and commercial uses. The antibodies may be used in different types of diagnostic tests, for example, to detect a wide variety of diseases or the presence of drugs (pharmaceuticals), toxins or other proteins including hormones, either in vitro or in vivo. The antibodies described herein may be useful in testing for disease, for example, in serum or blood of patients. The disease may including OX40 related diseases or disease or indications not related to OX40 including various cancers, inflammatory or autoimmune disease. Antibodies may also be used in the radioimmuno-detection and radioimmuno-therapy of cancer, and some new testing methods can utilize these described antibodies to target only the cell membranes of specific cell types, i.e., cancer.

The antibodies described herein could be made part of a kit or other diagnostic package. As such, provided herein is a diagnostic kit, or article of manufacture for use with the pretreatment method herein. The diagnostic kit may comprise any one or more of the following: antagonist/antibody/drug reference material; positive control neutralizing antibody (preferably goat of cyno monkey); Protein A+G column (e.g. Protein A/G column); delipidation reagent; immunoglobulin affinity purification buffer(s) (for example binding, elution and neutralization buffers); complement serum; assay diluent for cells; instruction manual or literature; vial of frozen cells (for example, WIL2 cells); cell labeling reagent (such as CELL TITER GLO®), etc. By way of example, the diagnostic kit may include but is not limited to: (a) delipidation reagent; (b) buffers (e.g. binding and elution buffers) for affinity purification of immunoglobulins; and (c) instruction manual instructing the user of the diagnostic kit to use the kit to pre-treat a biological sample from an autoimmune disease or cancer subject prior to conducting a cell based bioassay (such as a neutralizing antibody assay) on the sample (e.g. to avoid the problem of serum interference). The diagnostic kit optionally further comprises any one or more of: drug reference material, positive control neutralizing antibody, complement serum, assay diluent for cells, and cell labeling reagent, etc.

The antibodies and other discoveries described herein also provide for high throughput screening methods. More specifically, and as understood by those skilled in the art, high throughput methods to screen for antagonistic or agonistic monoclonal antibodies or small molecules that bind to OX40-receptors, and that can inhibit the generation and function of Tr1 cells or promote the generation and function of Tr1 cells, are made possible. In one such method, a human T cell line (SU-DHL-1) having the ability to produce IL-10 was transfected with the human OX40-gene (SUOX40). 100,000 SUOX40 cells were cultured with either 100,000 mouse fibroblast cells (L cells) or 100,000 mouse fibroblast cells expressing the human OX40-ligand (OX40-ligand L cells) in 96 well-plates. After 48 hours of culture, culture supernatants were collected for the measurement of IL-10 by IL-10-specific ELISA. In a representative experiment, 100,000 SUOX40 cells produced up to 6,000 pg/ml IL-10 cultured in the absence of OX40-ligand. In the presence of OX40-ligand, 100,000 SUOX40 cells produced less than 1,000 pg/ml IL-10. This culture method may be used to screen for, inter alia, antagonistic monoclonal antibodies or small molecules that block the ability of OX40-ligand to inhibit IL-10 production by SUOX40 cells. Alternatively, this culture method may be modified by replacing OX40-ligand expressing L cells with potential agonistic monoclonal antibodies or small molecules specific to OX40 to determine, inter alia, their ability to inhibit IL-10 production by SUOX40 cells.

The anti-OX40 antibodies described herein can be used as an assay or in an assay for testing or measuring the activity of a drug or other molecule found in an organism or organic sample. They could also be used in a quantitative assay to measure the amount of a substance in a sample. Bioassays and immunoassays are among the many varieties of specialized biochemical assays by which these antibodies might be used. The anti-OX40 antibodies taught herein can be used in other assays to measure processes such as enzyme activity, antigen capture, stem cell activity, and competitive protein binding.

Human GITRL, OX40L, 4-1BBL, ICOSL expressing L cells were generated by retroviral mediated transduction, as understood by those of skill in the art. Briefly, full-length coding sequence for human GITRL (Accession#NM 005092), OX40L (Accession#NM_003326), 4-1BBL (Accession#NM_003811), ICOSL (Accession#NM_015259) was amplified by RT-PCR with RNA prepared from HSV-1 stimulated PBMCs. Subsequently the cDNAs were cloned into an MSCV based retroviral vector pMIGW2 and the resulting plasmids were verified by restriction enzyme digestion and DNA sequencing. To produce recombinant retrovirus, each vector was co-transfected with packaging constructs pCL-gp (gag/pol) and pHCMV-VSVg (VSV glycoprotein envelop) in HEK293T cells. Two days later, the virus containing culture supernatants were harvested and used to infect CD32 L cells at moi 100. Under this condition >95% cells were productively transduced.

Isolated $CD14^+$ monocytes (purity >94%) were cultured in the presence of 100 ng/ml GM-CSF and 50 ng/ml IL-4 (both from R&D) for 5 days, as understood by those of skill in the art. The resulting immature DCs were washed and cultured for 24 h with IFN-α (1000 U/ml, PBL Biomedical Laboratories), IL-10 (10 ng/ml, R&D), and irradiated CD40L-transfected L cells (DC to L cell ratio, 4:1) to obtain mature DCs, as understood by those of skill in the art.

Naïve $CD4^+$ T cells and memory $CD4^+$ T cells (each purity >99%) were isolated from PBMCs using $CD4^+$ T cell Isolation Kit II (Miltenyi Biotec) followed by cell sorting ($CD4^+CD45RA^+CD45RO^-CD25-$ fraction as naïve T cells and $CD4^+CD45RA^-CD45RO^+CD25^-$ fraction as memory T cells), as understood by those of skill in the art. $4 \times 10^4$ freshly purified allogeneic naïve CD4+ T cells were co-cultured with immature or cultured DCs (DC to T ratio, 1:10) in the presence or absence of recombinant human OX40L (R&D, 100 ng/ml) in round-bottomed 96-well culture plates for 7 days, as understood by those of skill in the art. Purified $CD4^+$ T cells were also cultured with IL-12 (10 ng/ml, R&D), IL-4 (25 ng/ml, R&D), or combination of dexamethasone ($5 \times 10^{-8}$ M, Life Technologies) and 1alpha, 25-dihydroxyvitamin D3 ($10^{-7}$ M) for 7 days in the presence of soluble anti-CD28 monoclonal antibody (CD28.2, 1 µg/ml) and IL-2 (50 U/ml, R&D) on the irradiated CD32/OX40L-L cells, CD32/GITRL-L cells, CD32/4-1BBL-L cells, or parental CD32-L cells which had been pre-coated with anti-CD3 monoclonal antibody (OKT3, 0.2 µg/ml) in 48-well culture plates (T cell to L cell ratio, 2.5:1), as understood by those of skill in the art. In some experiments, $CD4^+$ T cells were cultured for 7 days on the CD32-L cells, mixture of CD32-L cells and CD32/ICOSL-L cells (ratio 1:1), or mixture of CD32/ICOSL-L cells and CD32/OX40L-L cells (ratio 1:1) pre-coated with anti-CD3 monoclonal antibody (0.2 µg/ml) in 48-well culture plates, as understood by those of skill in the art. RPMI 1640 was used and supplemented with 10% FCS, 2 mM L-glutamine, 1 mM sodium pyruvate, penicillin G, and streptomycin for the cultures, as understood by those of skill in the art.

The cultured T cells were collected and washed, and then restimulated with plate-bound anti-CD3 (5 µg/ml) and soluble anti-CD28 (2 µg/ml) at a concentration of $1 \times 10^6$ cells/ml for 24 h, as understood by those of skill in the art. The levels of IL-4, IL-10, TNF-$\alpha$, and IFN-$\alpha$ in the supernatants were measured by ELISA (all kits from R&D), as understood by those of skill in the art. For intracellular cytokine production, the cultured T cells were restimulated with 50 ng/ml of PMA plus 2 µg/ml of ionomycin for 6 h. Brefeldin A (10 µg/ml) was added during the last 2 h, as understood by those of skill in the art. The cells were stained with a combination of PE-labeled monoclonal antibodies to IL-4 or TNF-$\alpha$ FITC-labeled monoclonal antibodies to IFN-$\alpha$ and APC-labeled anti-IL-10 (all from BD) using FIX and PERM kit (CALTAG), as understood by those of skill in the art.

T cells were collected and re-suspended in an EDTA-containing medium to dissociate the clusters, as understood by those of skill in the art. Viable cells were counted by trypan-blue exclusion of the dead cells, as understood by those of skill in the art. For suppressive function assay, naïve CD4$^+$ T cells (A) and Tr1 cells generated from naïve CD4$^+$ T cells by anti-CD3 monoclonal antibody, anti-CD28 monoclonal antibody, IL-2, Dex, and vit D3 in the presence of parental L cells (B) or OX40L-L cells (C), these three cell types and their mixtures at a 1:1 ratio were then restimulated for 5 days by culturing in the presence of 5 µg/ml anti-CD3 monoclonal antibody and 1 µg/ml anti-CD28 monoclonal antibody, after which time the cellular proliferation was assessed by [$^3$H]thymidine incorporation, as understood by those of skill in the art.

Generation of Anti-Human OX40-Specific Monoclonal Antibodies

Figure 10:
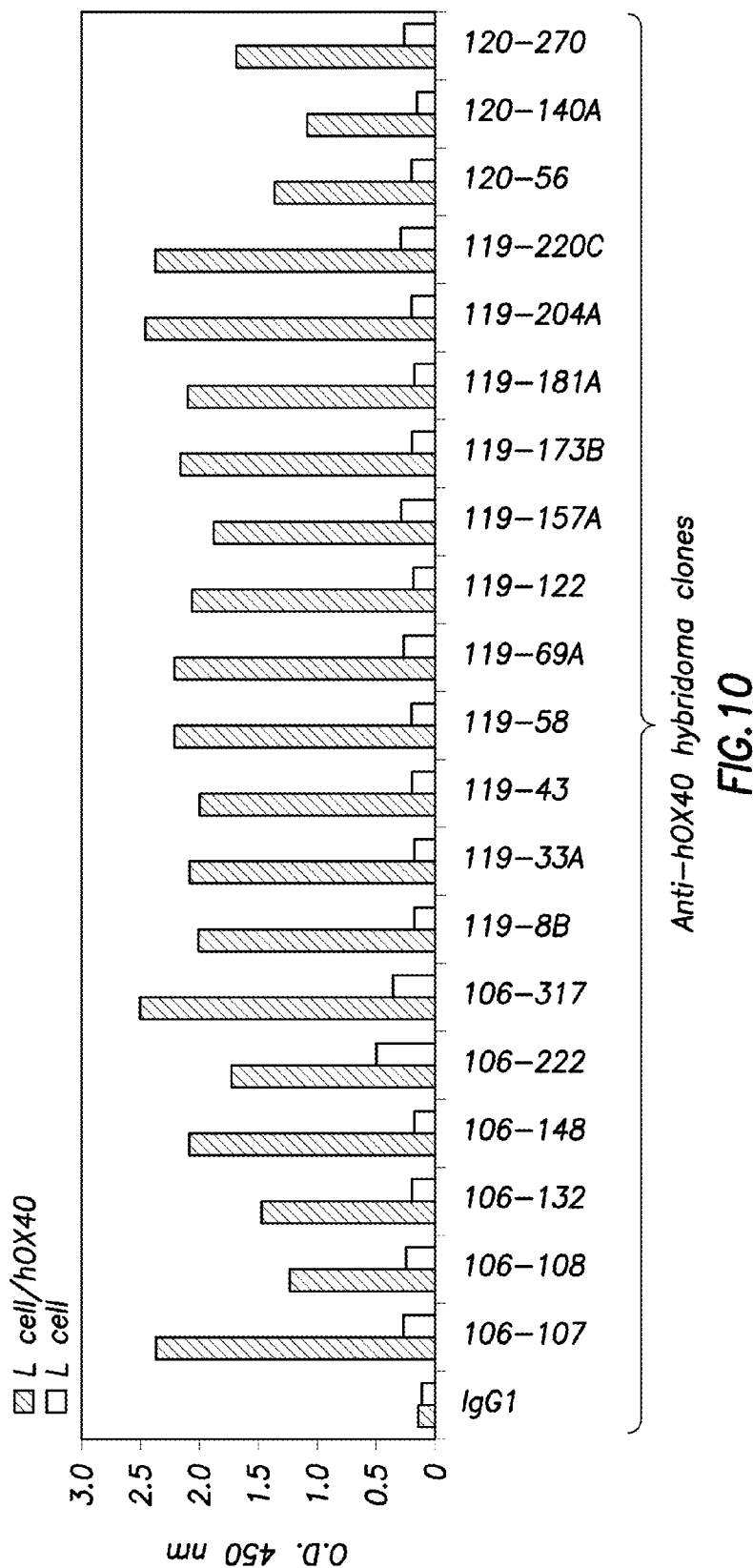
FIG. 10 shows the results of screening of anti-human OX40 hybridoma supernatants against L-OX40 versus L parental cells as determined by ELISA.
Figure 11:
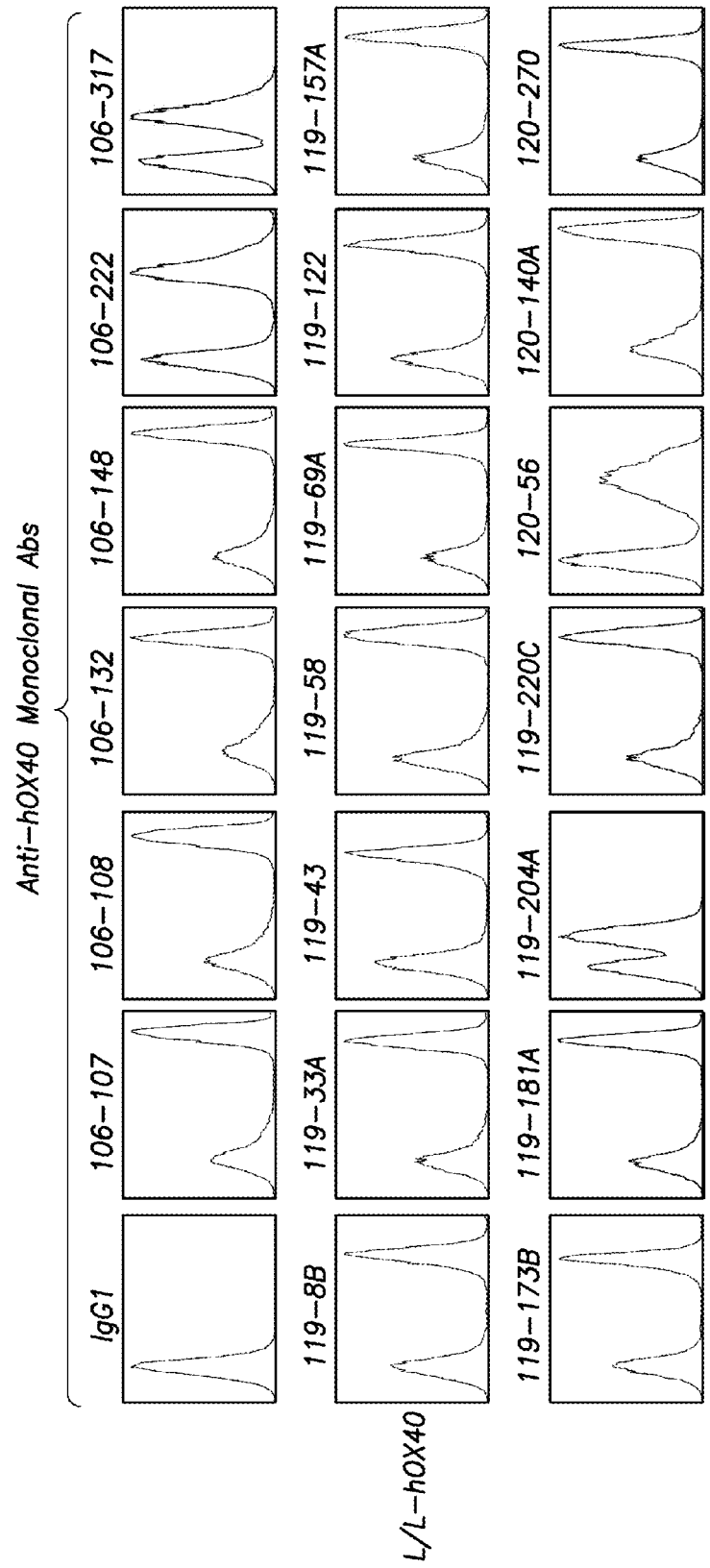
FIG. 11 shows the screening of human OX40-specific monoclonal antibodies as determined by flow cytometry analysis according to an embodiment of a method of the present invention.
Figure 12:
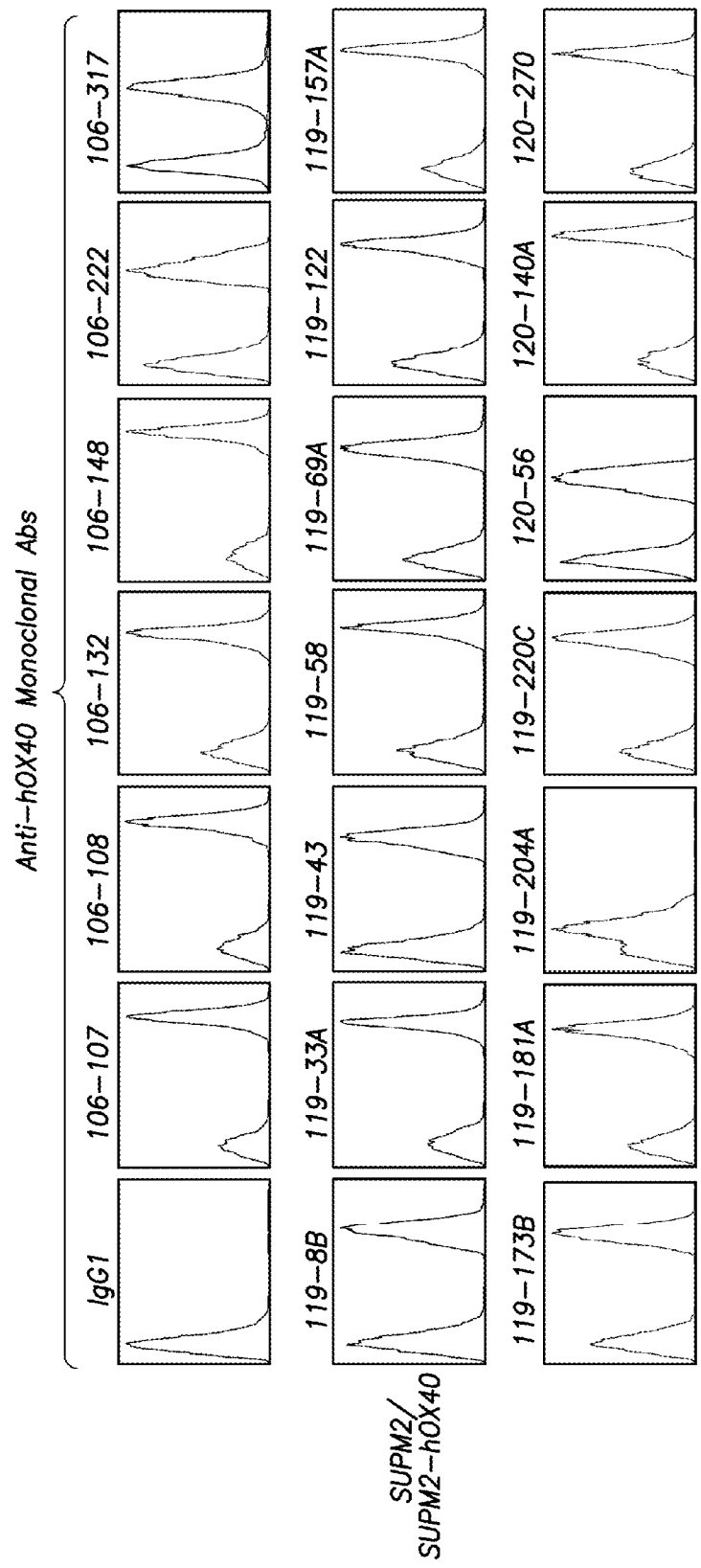
FIG. 12 shows the confirmation of anti-hOX40 monoclonal antibodies specificity by using SUPM2 cells expressing OX40 (SUPM2-OX40) according to an embodiment of a method of the present invention.

We generated multiple agonist mouse monoclonal antibodies against human OX40. The antigen binding specificity of the antibodies was confirmed by flow cytometry (FIGS. 10-12). The agonist activity of the antibodies was validated through functional assays. We found that nine of the 20 OX40-specific antibodies could block vitamin D3/dexamethasone-mediated generation of Tr1 cells from CD4$^+$ T cells (FIG. 13), enhance CD4$^+$ T-cell proliferation (FIG. 14), and suppress ICOS$^+$CD4$^+$CD25$^{high}$FOXP3$^+$ Treg IL-10 production (FIG. 16). We titrated the antibodies and found that five possessed potent activity in suppressing Tr1 cell generation at concentrations as low as 4 ng/ml (FIG. 15).

OX40 Antibodies Inhibit CD4$^+$CD25$^{high}$FOXP3$^+$ Treg Function

Figure 18:
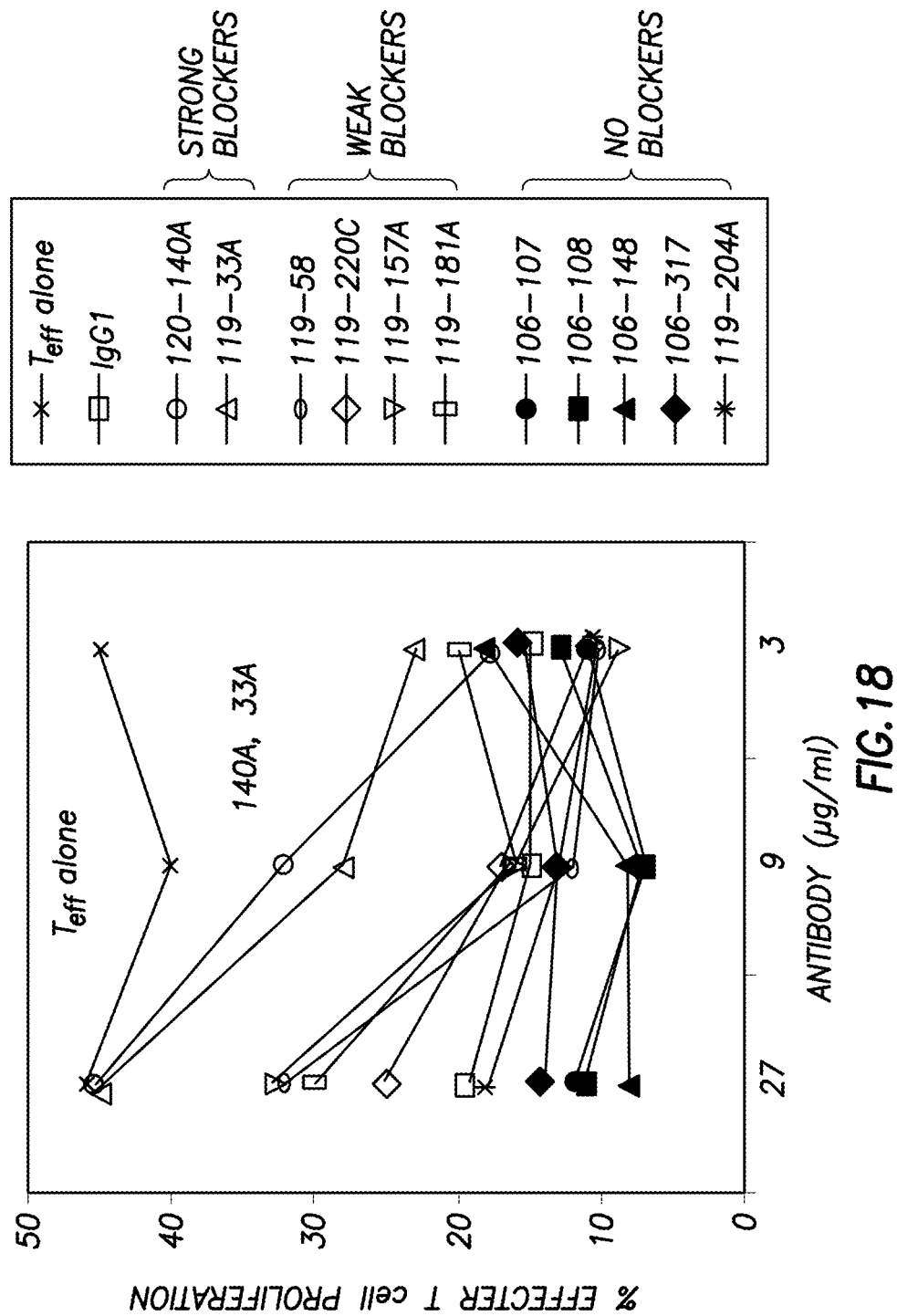
FIG. 18 demonstrates the identification of anti-hOX40 monoclonal antibodies that do not inhibit Tr1 cell generation but block FOXP3$^+$CD4$^+$CD25$^{high}$ Treg function according to an embodiment of a method of the present invention.

Some of the OX40 monoclonal antibodies inhibit the suppressive function of FOXP3$^+$ Treg (FIG. 17). Of the five antibodies (119-8B, 119-43, 119-122, 119-173B, and 106-222) that potently inhibit IL-10 production from Tr1 cells and CD4$^+$CD25$^{high}$CD127$^-$FOXP3$^+$ Tregs, three (119-43, 119-122, and 106-222) were potent in blocking CD4$^+$CD25$^{high}$CD127$^-$FOXP3$^+$ Treg function (FIG. 17). However, two (119-33 and 120-140A) of the 11 antibodies that have no activity against IL-10 production, but block CD4$^+$CD25$^{high}$FOXP3$^+$ Treg function (FIG. 18).

Anti-Human OX40 Monoclonal Antibodies

Generation of anti-human OX40 monoclonal antibodies was performed for example, by immunizing 6-8-wk-old BALB/c mice with a mouse cell line transfected with human-OX40 following established protocols. Hybridoma clones secreting monoclonal antibody that specifically stained OX40$^+$ cells were established and further analyzed.

We design an exhaustive screening to detect those clones that trigger OX40 signaling (i.e., agonists antibodies) by inhibiting the generation and function of Tr1 cells. Those clones were further purified. Agonist antibodies against hOX40 may be humanized and use in clinical protocols for human anti tumor therapy, either alone or in combination with anti tumor vaccination and other adjuvants. Several different tumor types could be the target of these antibodies, including melanoma, lymphoma and breast cancer.

In another embodiment, 6-8 week-old BALB/c female mice were used for footpad or subcutaneous immunization. Each mouse was injected with 5 million murine L cells transfected with human-OX40 (L-OX40) 6 times at 3 days intervals. Three days after the sixth injection, mice were sacrificed and popliteal lymph nodes (from footpad immunization) or spleen (from subcut immunization) were removed and cells were fused with SP2.0 myeloma or NSO myeloma cells at a ratio of 1 to 1 to generate hybridoma clones using established protocols. Hybridoma clones secreting monoclonal antibody were then screened for their binding specificity to L-hOX40 cells by ELISA assays. Hybridoma supernatants that bind to L-hOX40 cells and not L parental cells were further confirmed for binding on L-hOX40 and SUPM2-hOX40 cells by flow cytometry analysis.

In the experiment of FIG. 10, hOX40 hybridoma supernatants were screened against L-hOX40 versus L parental cells by ELISA. Twenty hOX40-specific monoclonal antibodies were selected. Twenty million L cells or L cells expressing human OX40 (L-hOX40) were coated on a 96-well plate by mixing cells with 0.01% magnesium calcium chloride in PBS and let dried overnight in a laminar hood. Plates were then frozen at $-20°$ C. for at least one day before use. For antibody binding assays, frozen cells were rehydrated with PBS and washed with wash buffer containing PBS plus 0.05% Tween 20, and blocked with 2% BSA in wash buffer. Conditioned cells were then used for binding to OX40 antibody supernatants. Antibody binding to cells was then detected with a secondary antibody, anti-mouse IgG FC HRP. hOX40-specific hybridoma supernatants recognize L cell expressing OX40 but not parental L cells.

In the experiment of FIG. 11, hOX40-specific monoclonal antibodies were screened by flow cytometry analysis. Equal number (100 k) of L cells and L-hOX40 were mixed in FACS buffer (1% FCS/2 mM EDTA/PBS) and incubated with 0.5 µg of FPLC (Protein A HiTrap/Gentle Ag/Ab elution buffer) purified antibodies. Cells were then washed and stained with a secondary antibody, PE-conjugated anti-mouse IgG. Two peaks indicate positive and negative stain by anti-hOX40 monoclonal antibody. A single peak suggests no binding or none-specific binding of antibodies. Twenty hOX40-specific monoclonal antibodies were confirmed by flow cytometry analysis.

In the experiment of FIG. 12, hOX40 monoclonal antibodies specificity was confirmed by using SUPM2 cells expressing hOX40 (SUPM2-hOX40). Equal number (100 k) of SUPM2 and SUPM2-hOX40 cells were mixed in FACS buffer (1% FCS/2 mM EDTA/PBS) and used for hOX40 monoclonal antibody binding as in FIG. 11. The binding specificity of each antibody was analyzed by flow cytometry. Two peaks indicate positive and negative stain by anti-hOX40 monoclonal antibody, while a single peak suggests no binding or none-specific binding by antibodies. Twenty hOX40-specific monoclonal antibodies were reconfirmed.

In the experiment of FIG. 13, we sought to indentify human OX40-specific monoclonal antibodies that can inhibit the generation of Tr1 cells from CD4+ T cells stimulated by VitD$_3$ (10 microMole mM)/Dex (50 nanoM), CD32L/ICOSL and anti-CD3/CD28 (0.2 microgram/ml). Anti-hOX40 monoclonal antibodies were added on day 0 of cell culture and CD4+ T cells after 7 days of stimulation were subjected to IL-10 intracellular staining followed by flow cytometry analysis. Representative Fluorescence Activated Cell Sorting (FACS) data are shown in A and the percentages of Tr1 cells for all anti-hOX40 monoclonal antibodies treatments are shown in B. Using cells obtained from this experiment, we sought to identify hOX40-specific monoclonal antibodies that stimulate CD4+ T cell proliferation (FIG. 14, cells were counted on day 7 after stimulation) and inhibit Tr1 generation from CD4+ (FIG. 13).

In order to indentify such hOX40 monoclonal antibodies for their ability to inhibit the generation of Tr1 cells from CD4+ T cells, Tr1 cells were generated and cultured as described in the experiments for FIG. 13 above. Representative FACS data are shown in A and percentage of Tr1 cells after treatment with nine anti-hOX40 monoclonal antibodies are shown in B. Five hOX40-specific monoclonal antibodies strongly inhibited the generation of Tr1 cells at 4 ng/ml concentration (FIG. 15).

Figure 16B:
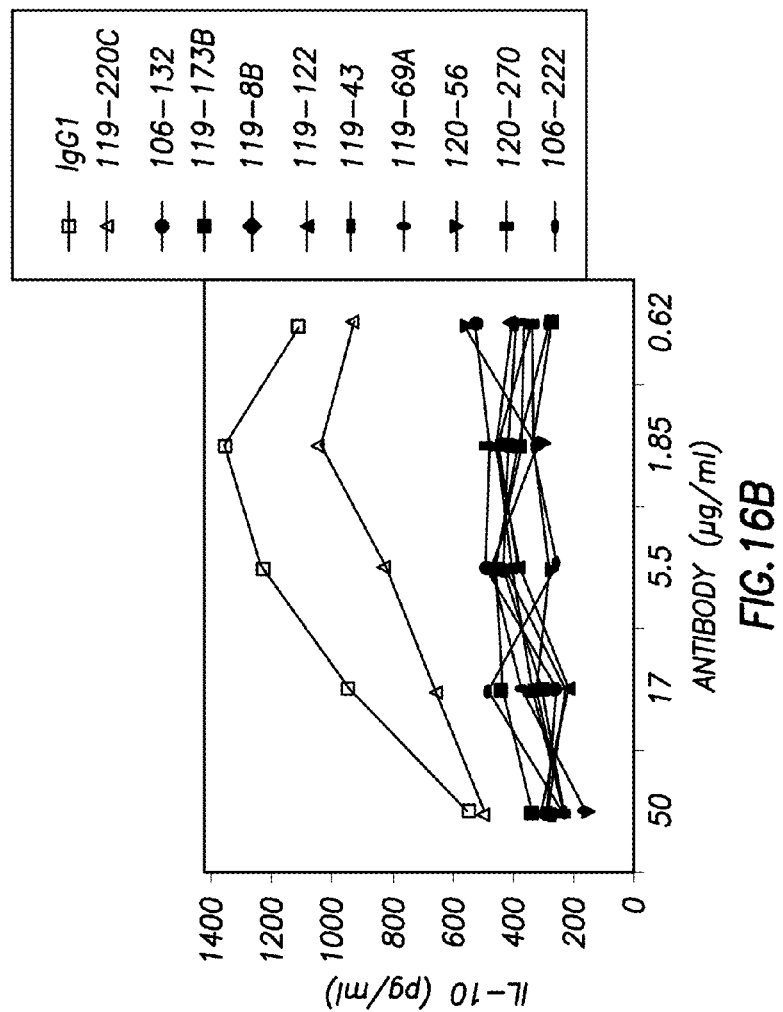
FIGS. 16A, 16B, and 16C shows OX40-specific monoclonal antibodies that inhibit IL-10 producing Tr1 cell generation from CD4$^+$ T cells also inhibit ICOS$^+$CD4$^+$CD25$^{high}$CD127$^-$ Treg IL-10 production and immunosuppressive function. Freshly sorted ICOS$^+$CD4$^+$CD25$^{high}$CD127$^-$ Tregs (ICOS$^+$Tregs) were stimulated with anti-CD3 (0.2 μg/ml) in the presence of CD32L/ICOSL cells and CD32L/OX40L cells (FIG. 16A) or OX40 monoclonal antibodies or control antibody (FIG. 16B) for five days. Cells were then restimulated with anti-CD3/CD28 for 24 hours and the supernatants were assayed for IL-10 by enzyme-linked immunosorbent assay (ELISA).
Figure 16A:
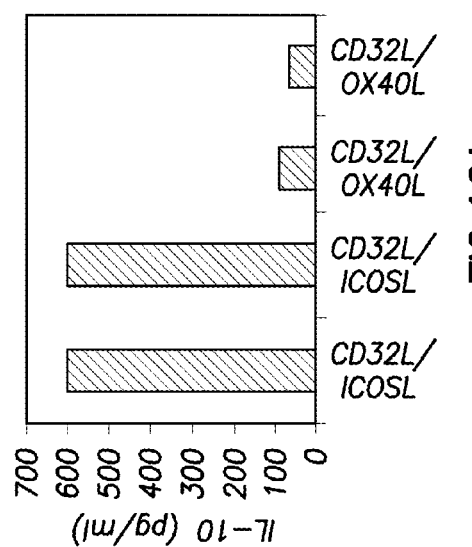
Figure 16C:
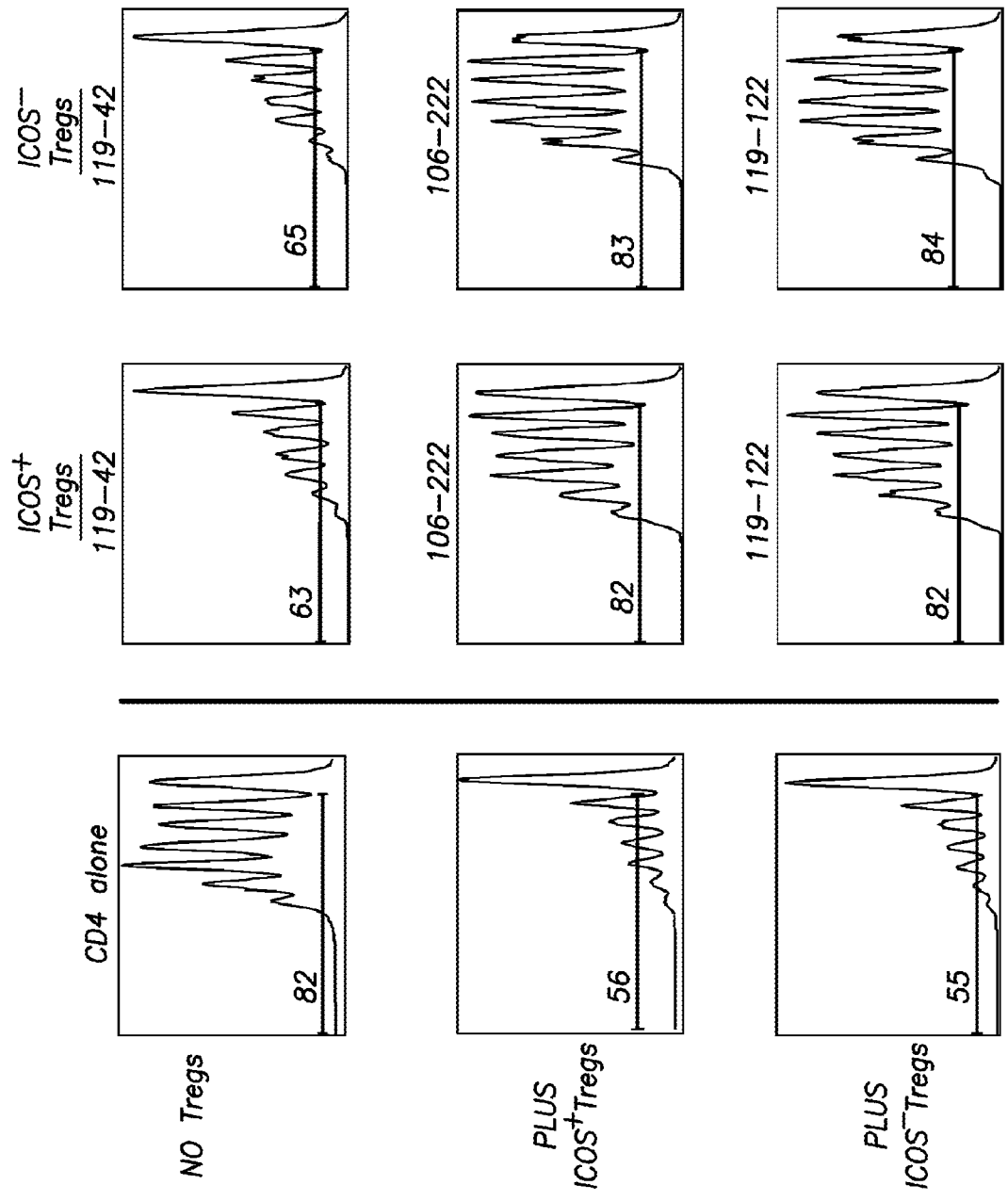

In the experiment of FIGS. 16A, 16B, and 16C, freshly sorted ICOS+CD4+CD127−CD25$^{high}$ T cells were stimulated with anti-CD3 (0.2 μg/ml) in the presence of CD32L/ICOSL cells and CD32L/hOX40L cells or anti-hOX40 monoclonal antibodies or control antibody for 5 days. Then, cells were counted and 5×10$^4$ cells were restimulated with anti-CD3/CD28 for 24 hrs and supernatants were assayed for IL-10 secretion with an Elisa kit. We identified hOX40-specific monoclonal antibodies that inhibit Tr1 generation from CD4+ T cells also inhibit IL-10 production from naturally ICOS+CD4+CD25$^{high}$ T cells. Freshly sorted ICOS+ ICOS− CD4+CD127−CD25$^{high}$ Tregs were cultured with CFSE-labeled CD4+CD25$^{low}$ cells in the presence of irradiated monocytes and anti-CD3 (0.3 μg/ml) and anti-hOX40 mAbs. After 3.5 days of culture, cell proliferation was assessed for dilution of CFSE in cells by FACS (FIG. 16C).

FIGS. 17 A and 17B shows the identification of anti-hOX40 monoclonal antibodies that inhibit the generation of Tr1 cells and block FOXP3+CD4+CD25$^{high}$ Treg function. Freshly sorted FOXP3+CD4+CD127−CD25$^{high}$ T cells (3.5×10$^4$) were cultured with CFSE-labeled CD4+CD25$^{low}$ cells (7×10$^4$) in the presence of Irradiated monocytes (7×10$^4$, 6000 rad) and 0.3 μg/ml anti-CD3 and various concentrations of anti-hOX40 monoclonal antibody. After 3 to 4 days of culture, cell proliferation was assessed for dilution of CFSE in cells by Flow cytometry analysis. Percentage of divided cells is indicated. Representative flow cytometry analyses are shown in FIG. 17A. Data for 6 monoclonal antibodies are shown in FIG. 17B.

In the experiment of FIG. 18, freshly sorted FOXP3+ CD4+CD127−CD25$^{high}$ T cells (3.5×10$^4$) were cultured with CFSE-labeled CD4+CD25$^{low}$ cells (7×10$^4$) in the presence of irradiated monocytes (7×10$^4$, 6000 rad) and 0.3 μg/ml anti-CD3 and various concentrations of OX40 monoclonal antibody. After 3 to 4 days of culture, cell proliferation was assessed for dilution of CFSE dye in cells by FACS. Data are representative of two experiments. We identified anti-hOX40 monoclonal antibodies that do not inhibit Tr1 generation but block FOXP3+CD4+CD25$^{high}$ Treg function.

In the experiment of FIGS. 19A and 19B, lymphoma-derived CD4+CD25$^{high}$ T cells were cultured with CFSE-labeled CD4+CD25$^{low}$ cells (7×10$^4$) isolated from healthy donor in the presence of irradiated allogenic monocytes (7×10$^4$, 6000 rad) and 0.3 microgram/ml anti-CD3 and 25 μg/ml of anti-hOX40 monoclonal antibody. After 3 to 4 days of culture, cell proliferation was assessed for CFSE dilution by FACS. Representative FACS analyses are shown in FIG. 19A and data for all experiments are shown in FIG. 19B. We discovered that the hOX40 agonist antibodies block lymphoma-derived CD4+CD25$^{high}$ Treg function.

Figure 20:
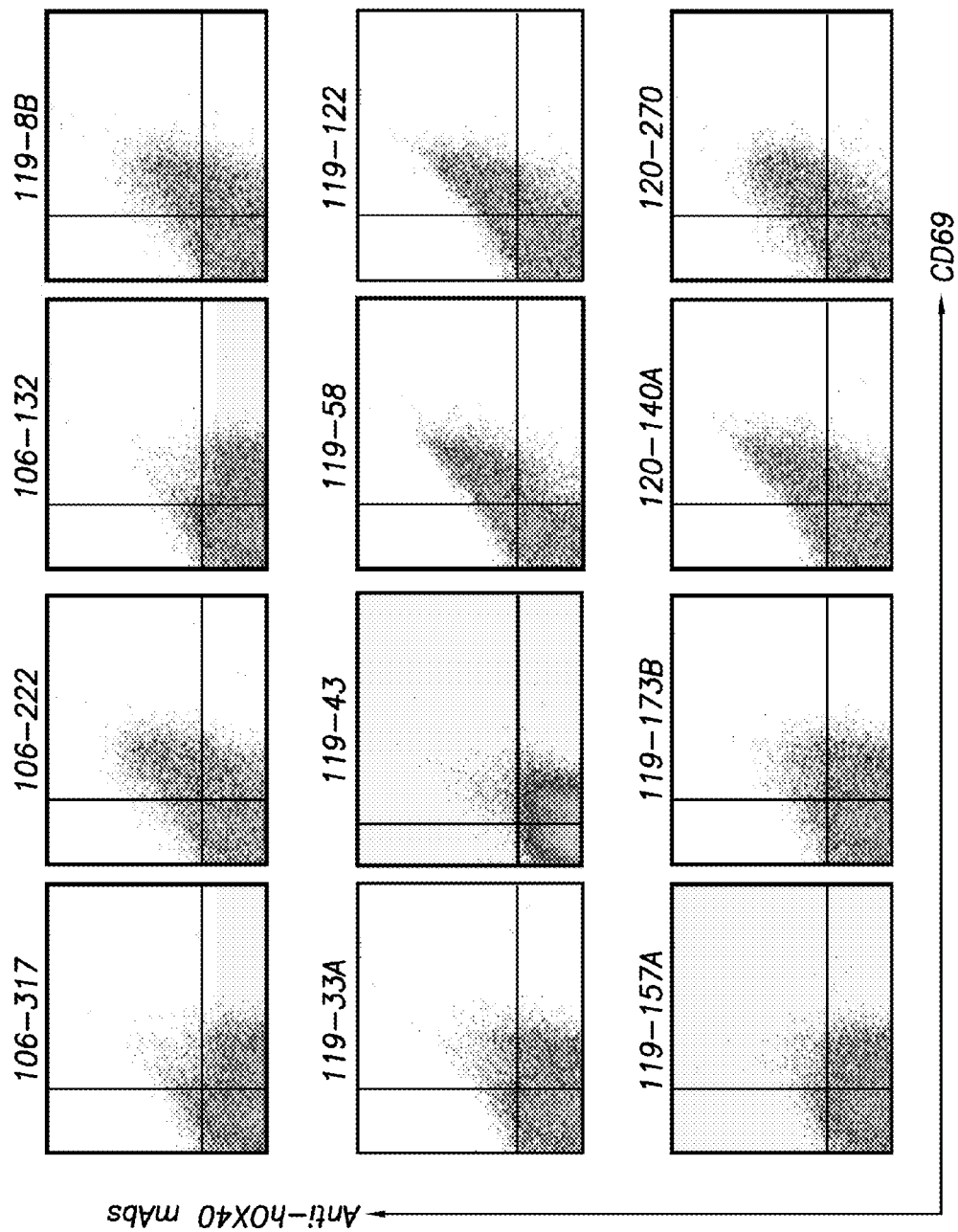
FIG. 20 shows that anti-hOX40 monoclonal antibodies can bind to rhesus CD4+ T cells. As shown, six of the anti-hOX40 mAbs can bind to rhesus activated CD4+ T cells and will bind to rhesus OX40 and activate OX40 signaling.

FIG. 20 shows the identification of OX40 agonistic antibodies that bind specifically to human and rhesus OX40. Rhesus peripheral blood mononuclear cells were obtained by ficoll centrifugation. CD4+ T cells were obtained by CD4 microbeads. CD4+ T cells were stimulated with 10 μg/ml of lectin *phaseolus vulgaris* (PHA). Two days after stimulation, cells were stained with anti-hOX40 mAbs followed by goat anti-mouse IgG-APC and CD69-PE. 106-317 served as a negative control. Six anti-hOX40 mAbs that strongly activate T cell proliferation could bind activated rhesus CD4+ T cells, is shown. These results indicate that the toxicity of these six anti-hOX40 monoclonal bodies can be tested in monkeys.

Only seven out of 500 anti-human OX40 positive clones obtained using the conventional fusion protocols, exhibited the properties of triggering OX40, including but not limited to, the ability to block IL-10 producing Tr1 generation and nTreg suppressive function as disclosed in Table 1.

TABLE 1

List of OX40-specific monoclonal antibodies

| | Monoclonal antibody clone | Block IL-10 | Block nTreg |
|---|---|---|---|
| 1 | 106-108 | − | − |
| 2 | 106-317 | − | − |
| 3 | 106-107 | − | − |
| 4 | 106-148 | − | − |
| 5 | 119-204A | − | − |
| 6 | 119-220C | − | + |
| 7 | 119-33A | − | + |
| 8 | 119-58 | − | + |
| 9 | 119-181A | − | + |
| 10 | 119-157A | − | + |
| 11 | 120-140A | − | + |
| 12 | 119-8B | + | − |
| 13 | 119-173B | + | − |
| 14 | 106-132 | + | + |
| 15 | 106-222 | + | + |
| 16 | 119-43 | + | + |
| 17 | 119-122 | + | + |
| 18 | 119-69A | + | + |
| 19 | 120-56 | + | + |
| 20 | 120-270 | + | + |

Hybridoma clones 106-222 and 119-122 were selected based on three criteria
1. They inhibit Tr1 cell generation from CD4+ T cells (inducible Treg)
2. They reverse the suppressive function of FOXP3+nTreg cells
3. They exhibit dose-dependent inhibition of Tr1 cells shut down and reversal of FOXP3+Treg function Chimeric and Humanized Antibodies Humanization (also called Reshaping or CDR-grafting) is an established technique for reducing the immunogenicity of monoclonal antibodies from xenogeneic sources (including but not limited to rodents) and for improving their activation of the human immune system. Although the mechanics of producing the engineered monoclonal antibody using the techniques of molecular biology are known, simple grafting of the rodent complementary-determining regions (CDRs) into human frameworks does not always reconstitute the binding affinity and specificity of the original monoclonal antibody.

In order to humanize an antibody, the design of the humanized antibody becomes the critical step in reproducing the function of the original molecule. This design includes various choices: the extents of the CDRs, the human frameworks to use and the substitution of residues from the rodent monoclonal antibody into the human framework regions (backmutations). The positions of these backmutations have been identified principally by sequence/structural analysis or by analysis of a homology model of the variable regions' 3D structure.

Recently, phage libraries have been used to vary the amino acids at chosen positions. Similarly, many approaches have been used to choose the most appropriate human frameworks in which to graft the rodent CDRs. Early experiments used a limited subset of well-characterized human monoclonal antibodies (often but not always where the structure was available), irrespective of the sequence identity to the rodent monoclonal antibody (the so-called fixed frameworks approach). Some groups use variable regions with high amino acid sequence identity to the rodent variable regions (homology matching or best-fit); others use consensus or germline sequences while still others select fragments of the framework sequences within each light or heavy chain variable region from several different human monoclonal antibodies. There are also approaches to humanization developed which replace the surface rodent residues with the most common residues found in human monoclonal antibodies ("resurfacing" or "veneering") and those which use differing definitions of the extents of the CDRs. Humanzied antibodies are described below. However, a chimeric antibody comprising the variable heavy and light regions of SEQ ID NOs: 4 and 10, or, SEQ ID NOs: 16 and 22 are also described herein.

Humanized monoclonal antibodies were be derived from the murine anti-OX40 antibody.

The isolated humanized anti-OX40 antibody may have a variable heavy chain CDR1 comprising the amino acid sequence of SEQ ID NO: 1 or 13. The isolated humanized anti-OX40 antibody may have a variable heavy chain CDR2 comprising the amino acid sequence of SEQ ID NO: 2 or 14. The isolated humanized anti-OX40 antibody may have a variable heavy chain CDR3 comprising the amino acid sequence of SEQ ID NO: 3 or 15.

The isolated humanized anti-OX40 antibody may have a variable light chain CDR1 comprising the amino acid sequence of SEQ ID NO: 7 or 19. The isolated humanized anti-OX40 antibody may have a variable light chain CDR2 comprising the amino acid sequence of SEQ ID NO: 8 or 20. The isolated humanized anti-OX40 antibody may have a variable light chain CDR3 comprising the amino acid sequence of SEQ ID NO: 9 or 21.

The isolated humanized anti-OX40 antibody may have a variable light chain comprising the amino acid sequence of SEQ ID NO: 11 or 23, or an amino acid sequence with at least 90 percent identity to the amino acid sequences of SEQ ID NO: 11 or 23. The isolated humanized anti-OX40 antibody may have a variable heavy chain comprising the amino acid sequence of SEQ ID NO.: 5 or 17, or an amino acid sequence with at least 90 percent identity to the amino acid sequences of SEQ ID NO: 5 or 17.

The isolated humanized anti-OX40 antibody may have variable light chain encoded by the nucleic acid sequence of SEQ ID NO: 12 or 24, or a nucleic acid sequence with at least 90 percent identity to the amino acid sequences of SEQ ID NO: 12 or 24. The isolated humanized anti-OX40 antibody may have variable heavy chain encoded by a nucleic acid sequence of SEQ ID NO: 6 or 18, or a nucleic acid sequence with at least 90 percent identity to the amino acid sequences of SEQ ID NO: 6 or 18.

Expression of Humanized Anti-OX40 Antibodies

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397 by Boss et al Antibodies and antibody fragments and variants can be produced from a variety of animal cells, preferably from mammalian cells, with murine and human cells being particularly preferred. Also, recombinant DNA expression systems could include those that utilize host cells and expression constructs that have been engineered to produce high levels of a particular protein. Such host cells and expression constructs may include *Escherichia coli*; harboring expression constructs derived from plasmids or viruses (bacteriophage); yeast such as *Saccharomyces cerevisieae* or *Pichia pastoras* harboring episomal or chromosomally integrated expression constructs; insect cells and viruses such as Sf9 cells and baculovirus; and mammalian cells harboring episomal or chromosomally integrated (including but not limited to, retroviral) expression constructs (such methods, for example, can be seen from the manuscript Verma et al., *J. Immunol. Methods* 216:165-181, 1998). Antibodies can also be produced in plants (such methods, for example, can be seen from U.S. Pat. No. 6,046,037; Ma et al., *Science* 268:716-719, 1995) or by phage display technology (such methods, for example, can be seen from Winter et al., *Annu. Rev. Immunol.* 12:433-455, 1994).

Human anti-OX40 antibodies that displayed a level of activity and binding specificity/affinity that are desirable can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

In another aspect, the isolated DNA encoding the VH region can be converted to a full-length heavy chain gene by operatively linking the VH-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG-1, IgG2, IgG3, IgG4, IgA, IgE, IgM or IgD constant region and any allotypic variant therein as described in Kabat, (Kabat, E. A., et al. (1991) Sequences of Proteins of Immunological Interest, Fifth Edition, U.S. Department of Health and Human Services, NIH Publication No. 91-3242), but most preferably is an IgG1 or IgG4 constant region. For a Fab fragment heavy chain gene, the VH-encoding DNA can be operatively linked to another DNA molecule encoding only the heavy chain CH1 constant region.

Also, a humanized antibody bound to surface antigen can interact with FcR-bearing cells. Such interaction can elicit effector function such as ADCC and/or enhance signaling because of Fc-mediated cross-linking. The interaction can be beneficial or harmful for therapy. Such harmful side effects include chills, fever, hypotension, and in some cases, dyspnea (Thistlethwaite J R Jr., Cosimi A B, Delmonico F L, et al.).

Certain harmful effects can originate in the protein complex found on the surface of a T cell. Upon activation of the T cell, the protein complex becomes involved in the transduction of signals generated via an antigen receptor. In short, activation of the T cell starts a cascade of events which include the enhanced cross-linking of the antigen receptor. The cross-linking of the receptor can contribute to strong mitogenic signaling that leads to the inducement of certain cytokines such as tumour necrosis factor alpha (TNF-$\alpha$), interleukin-2 (IL-2) and interferon gamma (IFN-$\gamma$). These cytokines are known to be toxic if generated in large amounts.

For example, anti-CD3 mAbs are currently used in the treatment of autoimmune disease including as Type I diabetes mellitus in which T cells mediated attack against pancreatic islets, producers of insulin (Kaufman A, and Herold K. Anti-CD3 mAbs for treatment of type 1 diabetes *Diabetes Metab Res Rev* 2009; 25: 302-306). Anti-CD3 antibodies are known to inhibit lysis of targets by T cells and enhance cross-linking of the antigen receptor CD3. In addition, together with its potent mitogenic activity, the anti-CD3 antibody is known to be a potent inducer of cytokines, specifically, tumour necrosis factor alpha (TNF-$\alpha$), interleukin-2 (IL-2) and interferon gamma (IFN-$\gamma$). The enormous release of cytokines, particularly TNF-$\alpha$ from T cells in response to the drug (Chatenoud L.) produce toxic effects. These undesirable side effects have been attributed to the cross-linking of T cells bearing CD3 molecules and the FcR bearing cells that bind to the Fc portion of the antibodies. The cross-linking activates both the T cell and the FcR bearing cells leading to the massive release of cytokines as previously mentioned.

Similarly, potential undesirable side effects could result using anti-OX40 antibodies. For instance, the anti-OX40 antibodies which bind to OX40 expressing T cells may also bind to FcR bearing cells and trigger the production of cytokines that may be beneficial or harmful for the patients treated with the antibody. To overcome this potential problem, we have designed and present herein methods of mutating the FcR portion of the anti-OX40 antibodies to avoid toxics effects and provide mutations to the FcR portion which may be desirable.

The site of human IgG1 that interacts with FcR (CD16, CD32 and CD64) is known. It maps to the upper CH2 domain. The most important amino acids are the two Leu residues at positions 234 and 235. By mutating these two residues to two Ala residues, interactions of IgG1 to all FcRs are abolished. Humanized anti-CD3 incorporated these mutations (HuOKT3AA), is a much safer drug and has a mechanism of action that is different than that of HuOKT3. See e.g., U.S. Pat. No. 6,491,916, incorporated by reference in its entirety herein.

The positions of the AA mutant are shown as followed:

```
Wild type IgG1 upper CH2
                                        (SEQ ID NO: 29)
            234 235
---A---P---E---L---L---G---G---P---

AA Mutant IgG1 upper CH2
                                        (SEQ ID NO: 30)
---A---P---E---A---A---G---G---P---
```

Hu222AA and Hu122AA described herein may contain these mutations. If the assay system contains FcR-bearing cells, you may see the difference between the wild type and the AA mutant. Otherwise, the two antibodies should behave the same.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

To create a scFv gene, the VH- and VL-encoding DNA fragments are operatively linked to another fragment encoding a flexible linker, e.g., encoding the amino acid sequence (Gly$_4$-Ser)$_3$, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., Nature (1990) 348:552-554.

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody. Another type of amino acid variant of the antibody alters the original glycosylation pattern of the antibody. Such altering includes deleting one or more carbohydrate moieties found in the antibody, and/or adding one or more glycosylation sites that are not present in the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 of U.S. Pat. No. 7,812,133, Col. 43, ls. 55 to Col. 44 l. 49, incorporated herein by reference, and under the heading of "preferred substitutions". If such substitutions result in a change in biological activity, then more substantial changes, denominated "exemplary substitutions" in the Table 1, or as further described below in reference to amino acid classes, may be introduced and the products screened.

Furthermore, substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: Cys, Ser, Thr, Asn, Gln; (3) acidic: asp, glu; (4) basic: his, lys, arg; (5) residues that influence chain orientation: gly, pro; and (6) aromatic: trp, tyr, phe. Non-conversative substitutions will entail exchanging a member of one of these classes for another class.

To express the antibodies, or antibody portions described herein, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used.

The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present).

Figure 23:
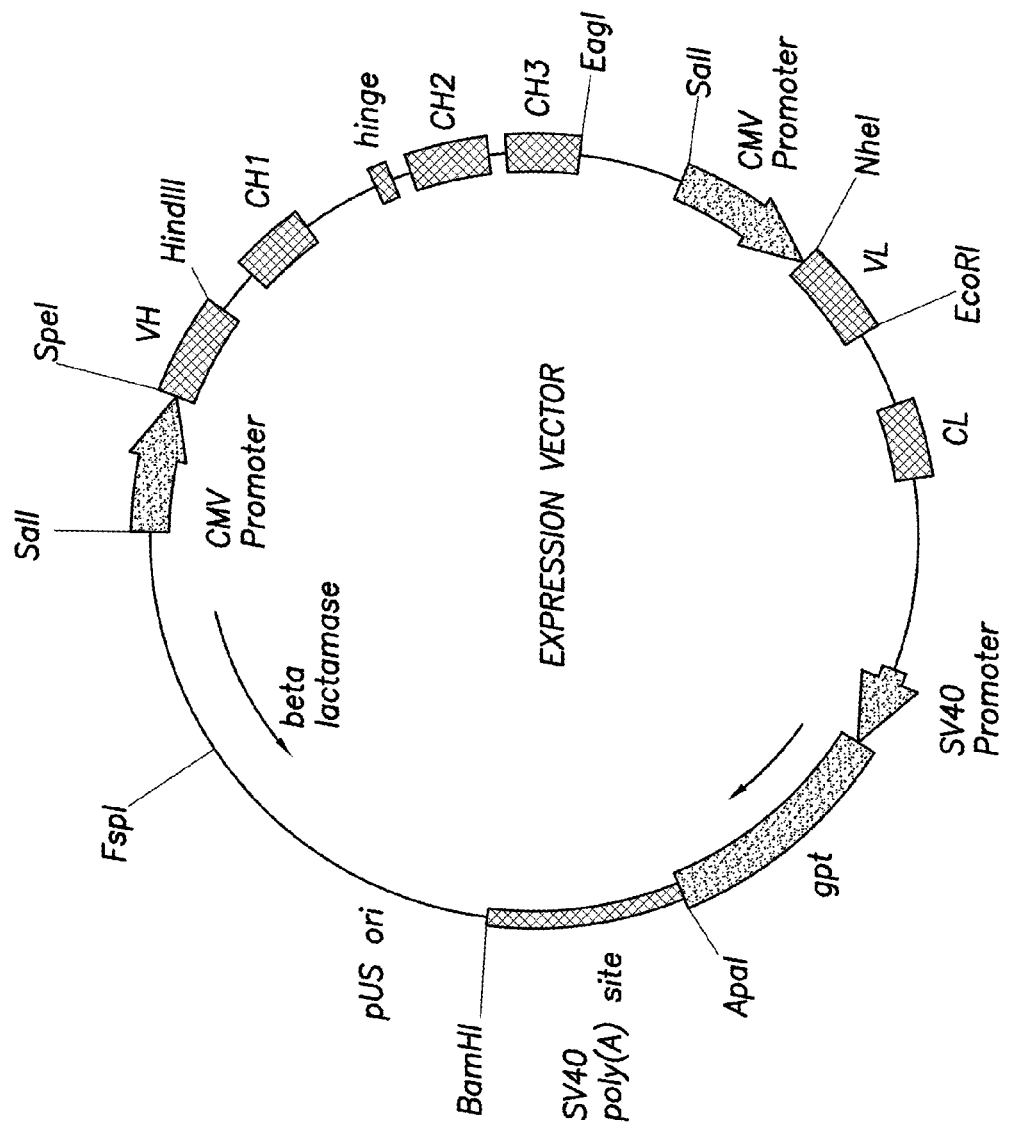
FIG. 23 depicts the schematic structure of the expression vector for Hu106 IgG1/kappa antibody (Expression Vector). Proceeding clockwise from the SalI site at the top, the plasmid contains the heavy chain transcription unit starting with the human cytomegalovirus (CMV) major immediate early promoter and enhancer (CMV promoter) to initiate transcription of the antibody heavy chain gene. The CMV promoter is followed by the VH exon, a genomic sequence containing the human gamma-1 heavy chain constant region including the CH1, hinge, CH2 and CH3 exons with the intervening introns, and the polyadenylation site following the CH3 exon. After the heavy chain gene sequence, the light chain transcription unit begins with the CMV promoter, followed by the VL exon and a genomic sequence containing the human kappa chain constant region exon (CL) with part of the intron preceding it, and the polyadenylation site following the CL exon. The light chain gene is then followed by the SV40 early promoter (SV40 promoter), the *E. coli* xanthine guanine phosphoribosyl transferase gene (gpt), and a segment containing the SV40 polyadenylation site (SV40 poly(A) site). Finally, the plasmid contains a part of the plasmid pUC 19, comprising the bacterial origin of replication (pUC ori) and beta-lactamase gene (beta lactamase). Locations of relevant restriction enzyme sites are shown in the figure.

As shown in FIG. 23, one such schematic structure of the expression vector for Hu106-222 IgG1/kappa antibody. Proceeding clockwise from the SalI site at the top, the plasmid contains the heavy chain transcription unit starting with the human cytomegalovirus (CMV) major immediate early promoter and enhancer (CMV promoter) to initiate transcription of the antibody heavy chain gene. The CMV promoter is followed by the VH exon, a genomic sequence containing the human gamma-1 heavy chain constant region including the CH1, hinge, CH2 and CH3 exons with the intervening introns, and the polyadenylation site following the CH3 exon. After the heavy chain gene sequence, the light chain transcription unit begins with the CMV promoter, followed by the VL exon and a genomic sequence containing the human kappa chain constant region exon (CL) with part of the intron preceding it, and the polyadenylation site following the CL exon. The light chain gene is then followed by the SV40 early promoter (SV40 promoter), the E. coli xanthine guanine phosphoribosyl transferase gene (gpt), and a segment containing the SV40 polyadenylation site (SV40 poly (A) site). Finally, the plasmid contains a part of the plasmid pUC 19, comprising the bacterial origin of replication (pUC ori) and beta-lactamase gene (beta lactamase). Locations of relevant restriction enzyme sites are shown in the figure.

The recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

As noted above, in addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology: Methods in Enzymology 185, Academic Press, San Diego, Calif. (1990). It will be appreciated that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al., U.S. Pat. No. 5,464,758 by Bujard et al. and U.S. Pat. No. 5,654,168 by Bujard et al.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr.sup.-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Mammalian host cells for expressing the recombinant antibodies described herein include Chinese Hamster Ovary (CHO cells) (such as dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It will be understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to OX40 The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than OX40 by crosslinking an antibody of the invention to a second antibody by standard chemical crosslinking methods Pharmaceutical Compositions and Pharmaceutical Administration The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The antibodies and antibody-portions of the invention can be incorporated into a pharmaceutical composition suitable for parenteral administration (e.g., intravenous, subcutaneous, intraperitoneal, intramuscular). The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical compositions are in the form of injectable or infusible solutions, such as compositions similar to those used for passive immunization of humans with other antibodies. The antibody can be administered by intravenous infusion or injection or intramuscular or subcutaneous injection.

The route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Supplementary active compounds can also be incorporated into the compositions. In certain embodiments, an antibody or antibody portion of the invention is co-formulated with and/or co-administered with one or more additional therapeutic agents that are useful for treating disorders in which OX40 inactivation is detrimental. For example, an anti-OX40 antibody or antibody portion of the invention may be co-formulated and/or co-administered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies. It will be appreciated by the skilled practitioner that when the antibodies of the invention are used as part of a combination therapy, a lower dosage of antibody may be desirable than when the antibody alone is administered to a subject (e.g., a synergistic therapeutic effect may be achieved through the use of combination therapy which, in turn, permits use of a lower dose of the antibody to achieve the desired therapeutic effect.

Antibodies described herein, or antigen binding portions thereof can be used alone or in combination to treat such diseases. It should be understood that these antibodies or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody taught herein. The additional agent also can be an agent which imparts a beneficial attribute to the therapeutic composition e.g., an agent which effects the viscosity of the composition.

The pharmaceutical compositions described herein may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual; and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

Example I

Chimeric and humanized 106-222 IgG1/kappa monoclonal antibodies (Ch222 and Hu222, respectively) were purified from culture supernatants of the corresponding NS0 stable transfectants using a protein A column as described in Appendices A and B. Hu222 was eluted from the column by two different ways. Briefly, Hu222 Lot I was eluted with low pH buffer and Lot II with Pierce's Gentle Ag/Ab Elution Buffer. The yield of Hu222 was better when the low pH buffer was used for elution. Ch222 was eluted from the column with Gentle Ag/Ab Elution Buffer.

Figure 21:
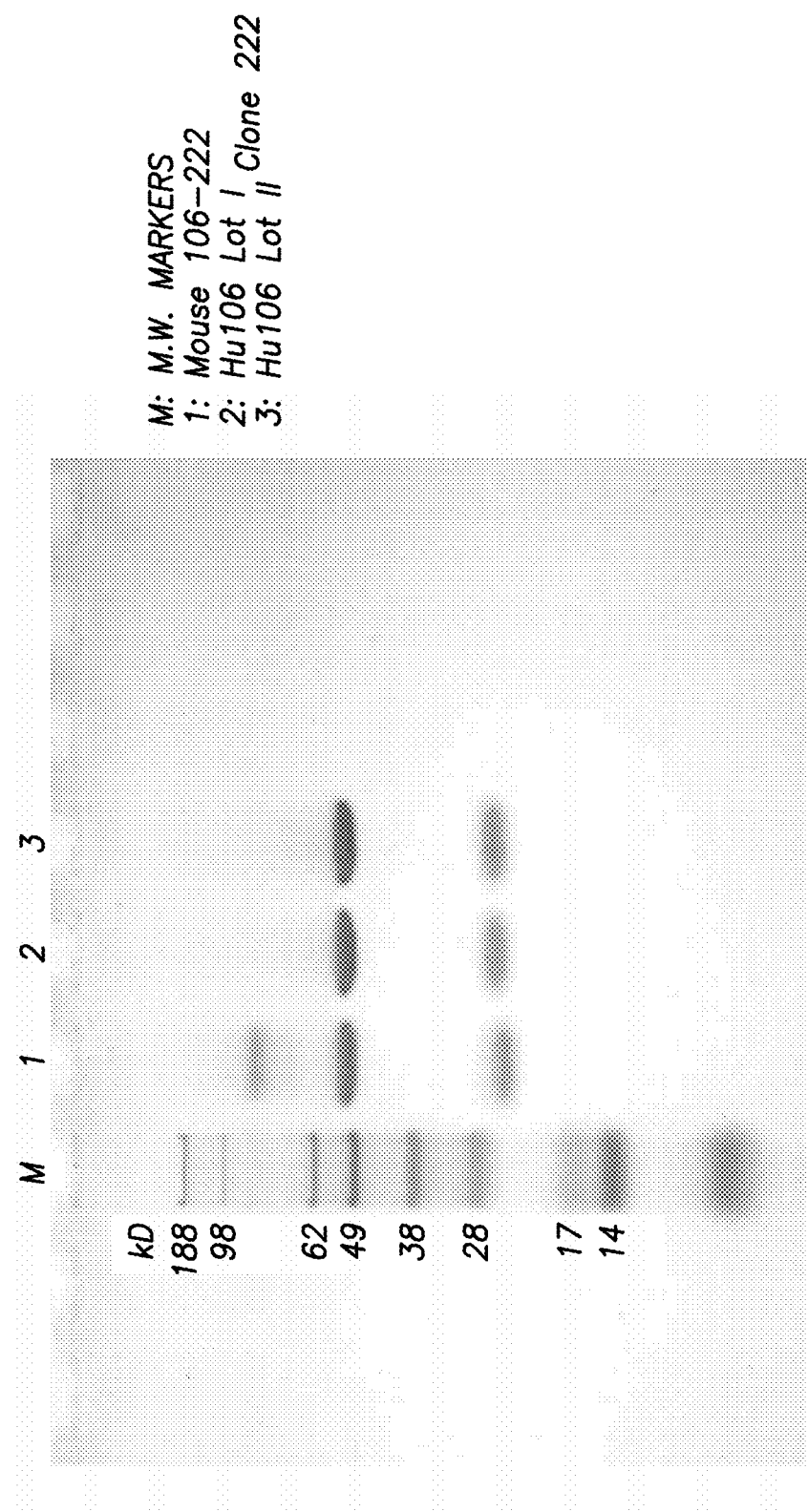
FIG. 21 shows that each of Hu106-222 Lot I and II antibodies of Example I is comprised of a heavy chain with a molecular weight of about 50 kD and a light chain with a molecular weight of about 25 kD. The purity of Hu106-222 Lot I and II antibodies appeared to be more than 95%.

Purified Hu222 Lot I and II antibodies were characterized by SDS-PAGE alongside with mouse 106-222 according to standard procedures. Five µg of each antibody was analyzed under reducing conditions. As shown in FIG. 21, each of Hu222 Lot I and II antibodies is comprised of a heavy chain with a molecular weight of about 50 kD and a light chain with a molecular weight of about 25 kD. The purity of Hu222 Lot I and II antibodies appeared to be more than 95%.

Endotoxin contamination in the humanized antibodies was analyzed with Lonza's Limulus Amebocyte Lysate (LAL) QCL-1000 kit. The endotoxin level was less than 0.5 EU/mg protein for both Hu222 Lot I and II antibodies.

Characterization of Hu106-222 for Binding to L/OX40 Cells

Binding of mouse 106-222, Ch106-222 and Hu106-222 antibodies to OX40 was examined in a FACS binding assay with L/hOX40 cells essentially according to the protocol supplied by Dr. Laura Bover. Antibodies bound to L/hOX40 cells were detected with PE-labeled goat anti-mouse IgG antibody (for mouse 106-222) or PE-labeled goat anti-human IgG antibody (for Ch106 and Hu106).

Figure 22:
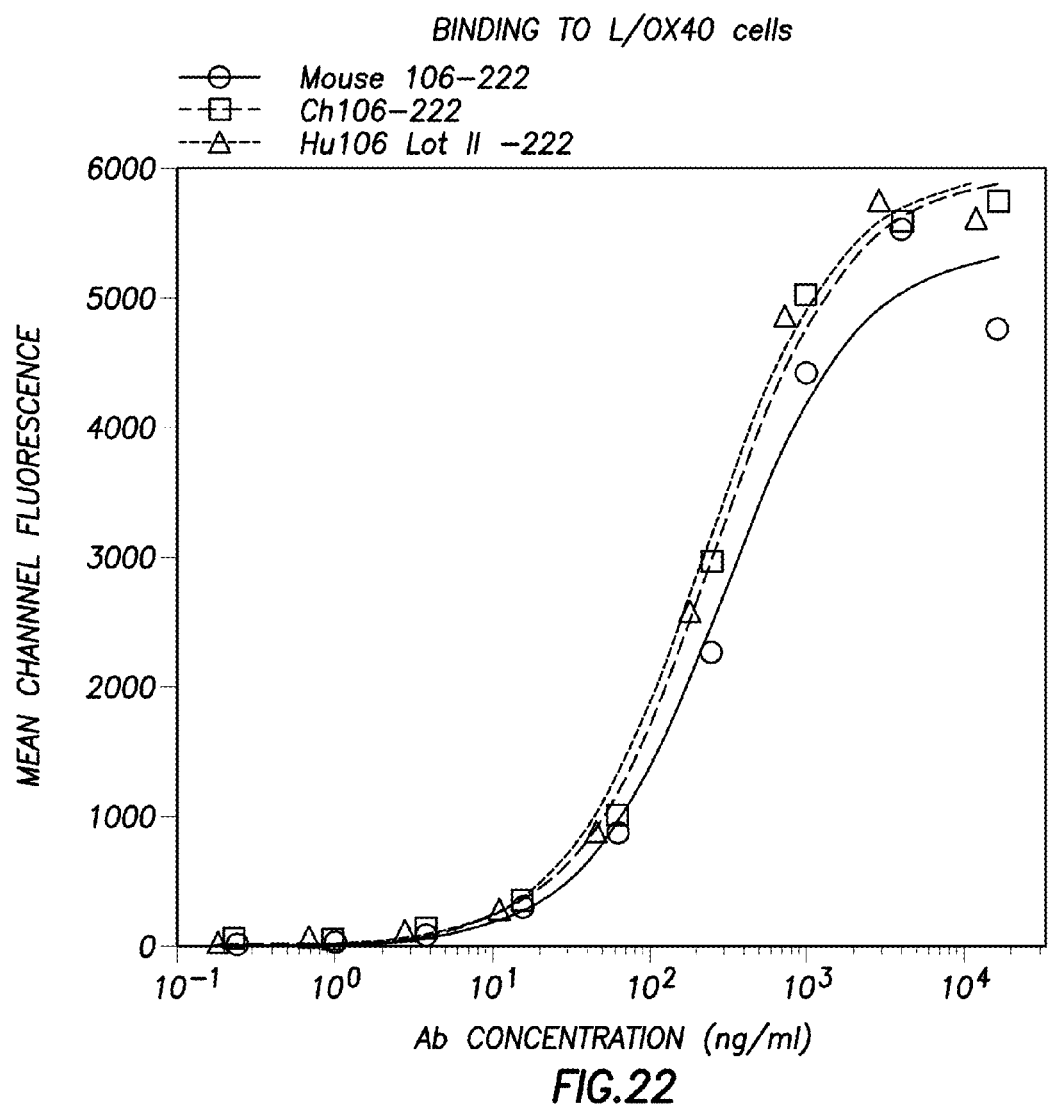
FIG. 22 shows the analysis of mouse 106-122, Ch106 and Hu106-222 (Lot II) antibodies for binding to L/OX40 cells (Example I).

FIG. 22 shows the analysis of mouse 106-222, Ch106 and Hu106-222 (Lot II) antibodies for binding to L/OX40 cells. The titration curve of Hu106-222 (Lot II) was nearly identical to that of Ch106-222, indicating that the antigen binding affinity of mouse 106-222 is retained in Hu106-222. The titration curve of mouse 106-222 was similar to those of Ch106 and Hu106; however, due to the difference of the secondary antibodies, the data only indicates that the affinity of mouse 106-222 is similar to that of Hu106-222.

Figure 24:
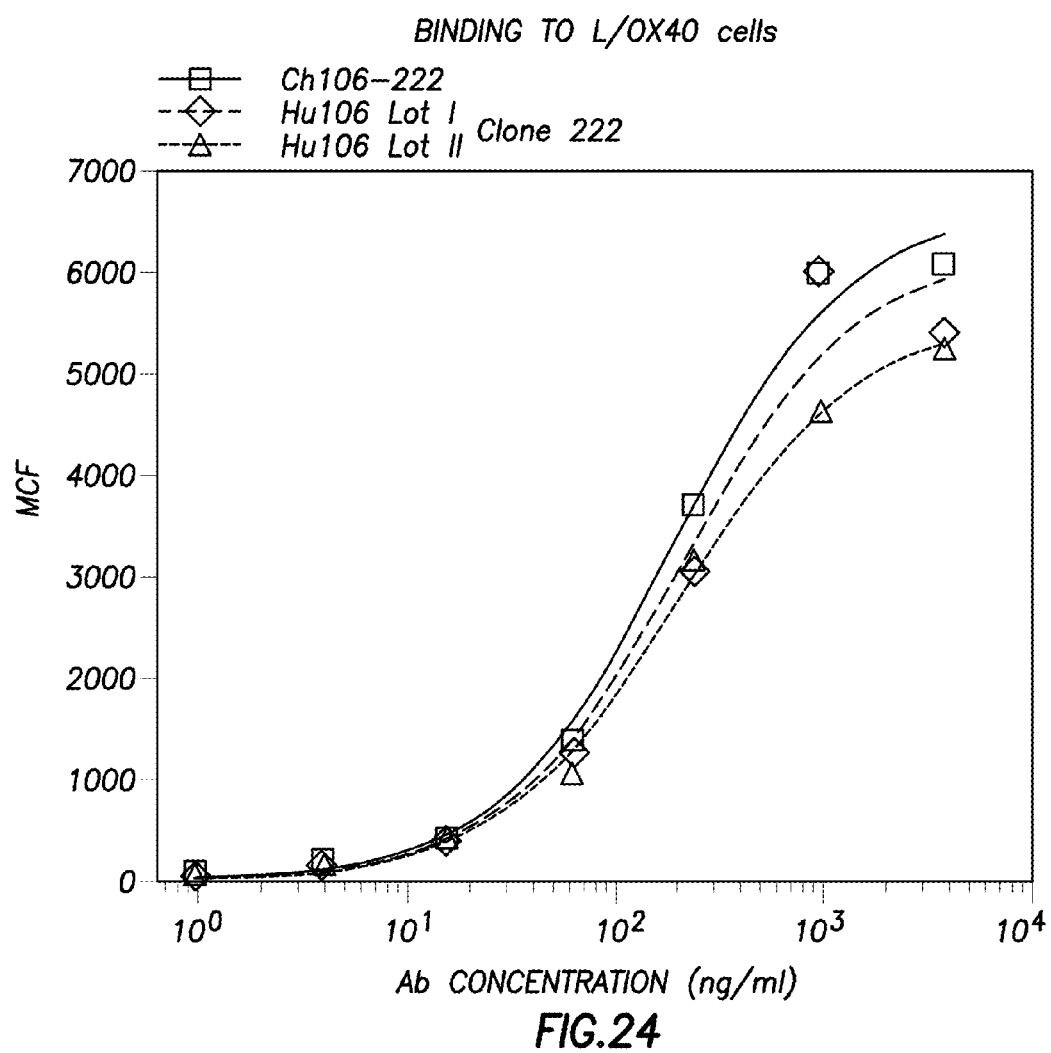
FIG. 24 shows the comparison between Hu 106-222 Lot I and II antibodies for binding to L/OX40 cells (Example I below).

FIG. 24 shows the comparison between Hu106-222 Lot I and II antibodies for binding to L/hOX40 cells. Although further analysis is needed, the affinity of the two lots of Hu106-222 appeared to be similar, if not identical, to each other. Hence, acid elution of Hu106-222 from a protein A column does not seem to affect its affinity.

Purification of Ch106-222

NS0 stable transfectant C8 was grown in 500 ml of Invitrogen's Hybridoma SFM medium in a roller bottle to exhaustion. The culture was spun down in Corning's 250 ml Centrifuge Tube (Cat#430776) in Beckman Coulter's Allegra X-12R Centrifuge (2000 RPM for 15 min). The culture supernatant was loaded onto a 1 ml GE Healthcare HiTrap MabSelect SuRe column (Cat#11-034-95) using a Pharmacia P1 pump. The column was washed with Tris-buffered saline (Pierce, Cat#28379) and eluted with Pierce's Gentle Ag/Ab Elution Buffer (Cat #21027). Fractions (about 1 ml) were collected and their OD at 280 nm read.

| Fraction # | OD at 280 nm |
|---|---|
| 3 | 0.12 |
| 4 | 0.30 |
| 5 | 0.18 |
| 6 | 0.11 |

Fractions 3 to 6 were pooled (volume=3.0 ml, OD at 280 nm=0.14). Pooled fractions were desalted onto a 10 ml Sephadex G25 medium column in PBS. Fractions of 1 ml were collected.

| Fraction # | OD at 280 nm |
|---|---|
| 5 | 0.09 |
| 6 | 0.19 |
| 7 | 0.12 |
| 8 | 0.12 |
| 9 | 0.00 |

Fractions 6 to 9 were pooled (volume=3.0 ml, OD at 280 nm=0.11). Pooled fractions were dialyzed overnight in PBS. After dialysis, the volume was 3.0 ml and OD at 280 nm was 0.19. This preparation is called Ch106, lot 8/31/09, with a concentration of 0.13 mg/ml.

Purification of Hu106-222

NS0 stable transfectant 1-C6 was grown in 500 ml of Invitrogen's Hybridoma SFM medium in a roller bottle to exhaustion. The culture was spun down in Corning's 250 ml Centrifuge Tube (Cat#430776) in Beckman Coulter's Allegra X-12R Centrifuge (2000 RPM for 15 min).

Lot 1: 150 ml of the culture supernatant was loaded onto a 1 ml GE Healthcare HiTrap MabSelect SuRe column (Cat#11-034-95) using a Pharmacia P1 pump. The column was washed with PBS and bound antibody was eluted with 0.1M glycine-HCl, 0.1 M NaCl (pH 3.0). Eluted fractions (1 ml each) were collected into tubes containing 50 μl 1M Tris-HCl (pH 8.0).

| Fraction # | OD at 280 nm |
|---|---|
| 2 | 0.88 |
| 3 | 2.84 |
| 4 | 1.29 |
| 5 | 0.63 |
| 6 | 0.18 |

Fractions 2 to 5 were pooled (volume=4.2 ml, OD at 280 nm=1.59). Pooled fractions were dialyzed overnight in PBS. After dialysis, the volume was 4.2 ml and OD at 280 nm was 1.54. The antibody solution (lot 9/18/09 I; 1.1 mg/ml) was filter-sterilized.

Lot II:

The remaining culture supernatant (350 ml) was loaded onto a 1 ml GE Healthcare HiTrap MabSelect SuRe column using a Pharmacia P1 pump. The column was washed with Tris-buffered saline and eluted with Gentle Ag/Ab Elution Buffer. Fractions (about 1 ml) were collected and their OD read at 280 nm.

| Fraction # | OD at 280 nm |
|---|---|
| 2 | 0.12 |
| 3 | 0.85 |
| 4 | 2.17 |
| 5 | 1.47 |
| 6 | 1.02 |
| 7 | 0.81 |
| 8 | 0.66 |
| 9 | 0.54 |
| 10 | 0.44 |
| 11 | 0.46 |

Fractions 3 to 7 were pooled (volume=4.2 ml, OD at 280 nm=1.22). The column was washed again with Tris-buffered saline and antibody eluted with 0.1M glycine-HCl, 0.1M NaCl (pH 3.0) to examine if elution by GentleAg/Ab Elution Buffer was efficient.

| Fraction # | OD at 280 nm |
|---|---|
| 1 | 0.05 |
| 2 | 0.05 |
| 3 | 1.23 |
| 4 | 0.49 |
| 5 | 0.10 |

Fractions 3 to 7 eluted with GentleAg/Ab Elution Buffer were pooled and desalted onto a 10 ml Sephadex G25 medium column in PBS. Fractions of 1 ml were collected.

| Fraction # | OD at 280 nm |
|---|---|
| 4 | 0.38 |
| 5 | 0.96 |
| 6 | 1.38 |
| 7 | 1.33 |
| 8 | 1.10 |
| 9 | 0.12 |

Fractions 5 to 8 were pooled (volume=4.0 ml, OD at 280 nm=1.12). Pooled fractions were dialyzed overnight in PBS. After dialysis, the volume was 4.0 ml and OD at 280 nm was 1.12. The antibody solution (lot 9/18/09 II; 0.8 mg/ml) was filter-sterilized.

The high salt elution method with Pierce's Gentle Ag/Ab Elution Buffer was not as efficient as the low pH method to elute bound human IgG1 antibody from the protein A column. As antibodies were not eluted in a sharp peak with Gentle Ag/Ab Elution Buffer, it was necessary to pool many fractions for collection of eluted IgG and desalt the pooled fractions before dialysis. The poor elution profile with Gentle Ag/Ab Elution Buffer and the extra purification step affected the yield of antibody. It is advised that the high salt elution method is used only if IgG to be purified is acid labile.

Example II

Purification of Ch119-122 and Hu119-122 Antibodies

Chimeric 119-122 IgG1/kappa monoclonal antibody (Ch119) was purified from culture supernatant of the corresponding NS0 stable transfectant (clone G11) grown in Hybridoma-SFM media (Invitrogen) using a protein A column. After elution with Pierce's Gentle Ag/Ab Elution Buffer, the buffer of Ch119 was exchanged to PBS by gel filtration and then dialysis. The concentration of Ch119 was 0.21 mg/ml.

Humanized 119-122 IgG1/kappa monoclonal antibody (Hu122) was purified from culture supernatant of the corresponding NS0 stable transfectant (clone 2F5) grown in Hybridoma-SFM media using a protein A column. Hu106-222 was eluted from the column with low pH buffer, neutralized with 1 M Tris-HCl (pH 8.0), and dialyzed in PBS. The concentration of Hu122 was 1.6 mg/ml.

Figure 25:
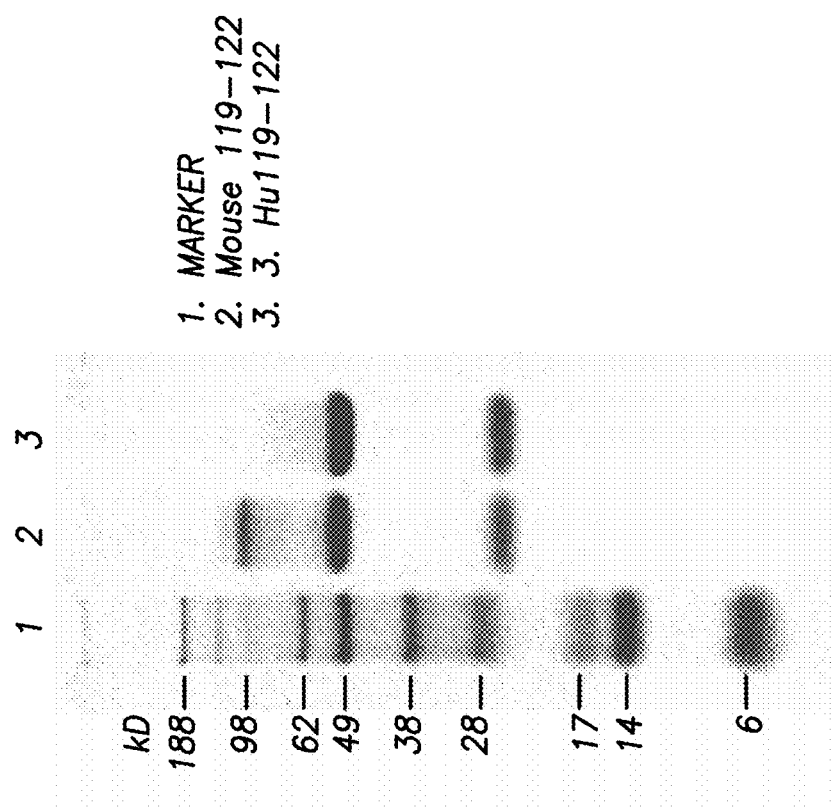
FIG. 25 shows Hu119-122 is comprised of a heavy chain with a molecular weight of about 50 kD and a light chain with a molecular weight of about 25 kD. The purity of Hu119 appeared to be more than 95% (Example II below).

Purified Hu106-222 was characterized by SDS-PAGE alongside with mouse 119-122 according to standard procedures. Five μg of each antibody was analyzed under reducing conditions. As shown in FIG. 25, Hu119-122 is comprised of a heavy chain with a molecular weight of about 50 kD and a light chain with a molecular weight of about 25 kD. The purity of Hu119 appeared to be more than 95%.

Characterization of Hu119-122 for Binding to L/hOX40 Cells

Binding of mouse 119-122, Ch119-122 and Hu119-122 antibodies to OX40 was examined in a FACS binding assay with L/OX40 cells essentially according to the protocol supplied by Dr. Laura Boyer. Antibodies bound to L/OX40 cells were detected with PE-labeled goat anti-mouse IgG antibody (for mouse 119-122) or PE-labeled goat anti-human IgG antibody (for Chi 19-122 and Hu119-122).

Figure 26:
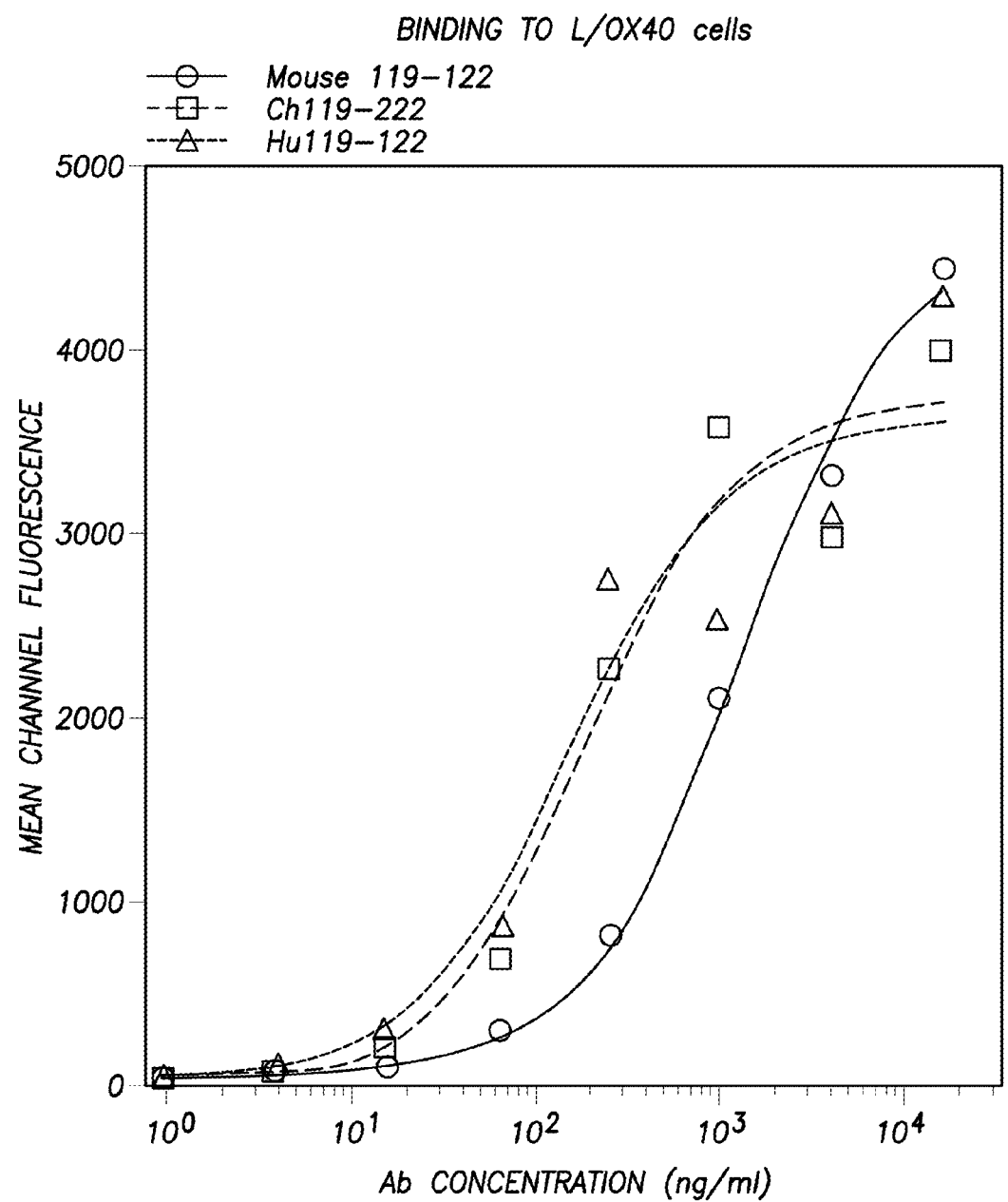
FIG. 26 shows the result of the FACS analysis of Ch119-122 and Hu119-122 antibodies described herein (Example II below).

FIG. 26 shows the result of the FACS analysis. The titration curve of Hu119-122 was similar to that of Ch119-122, suggesting that the antigen binding affinity of mouse 119-122 is retained in Hu119-122. However, the MCF values at higher antibody concentrations of Ch109-122 and Hu119-122 do not fall right on the corresponding curves. After adjusting the experimental conditions, the FACS analysis should be repeated.

Example III

Figure 27:
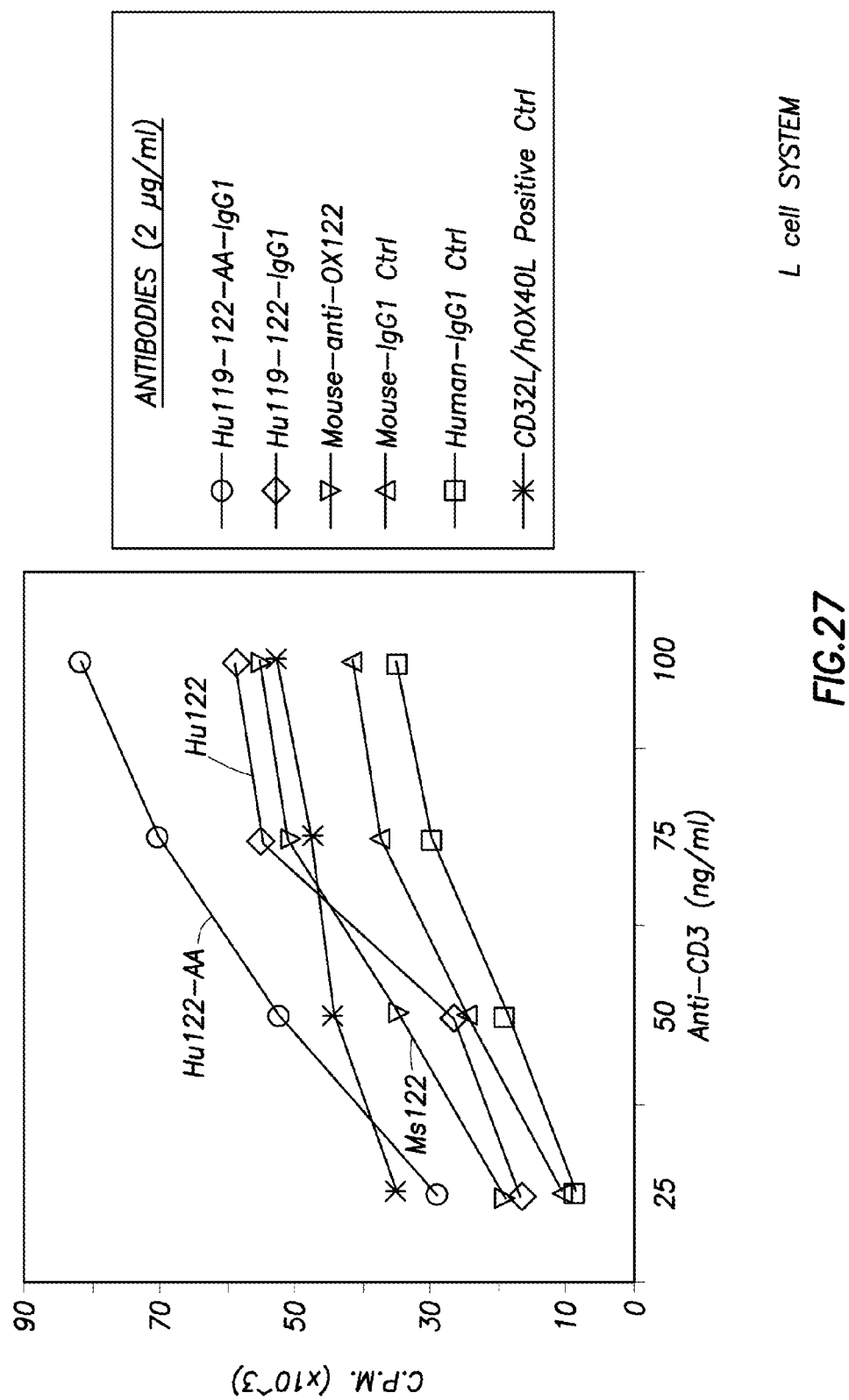
FIG. 27 shows that humanized anti-human OX40 mAb clone 119-122 (Hu119), and its FcR binding mutated antibody (Hu119-AA) enhanced naïve CD4+ T cell proliferation. Hu119-122 yielded better T cell stimulatory activity compared to parental mouse anti-human OX40 mAb (Mouse119-122). However, chimeric anti-human OX40 mAb (Ch119, mouse VH and VL but human gamma-1 and kappa constant regions) failed to enhance T cell proliferation.

To evaluate the ability of our humanized anti-human OX40 antibodies to enhance T cell proliferation, we performed proliferation assays using anti-CD3 coated CD32-L cells and freshly sorted naïve CD4$^+$ T cells. FIG. 27 shows that humanized anti-human OX40 mAb clone 119-122 (Hu122), and its FcR binding mutated antibody (Hu122-AA) enhanced naïve CD4$^+$ T cell proliferation. Hu122 yielded better T cell stimulatory activity compared to parental mouse anti-human OX40 mAb (Mouse122). (FIG. 27)

FcR binding mutated humanized anti-human OX40 mAb clone 106-222 (Hu222-AA) and chimeric anti-human OX40 mAb clone 106-222 (Ch222) enhanced anti-CD3 stimulated naïve CD4$^+$ T cell proliferation. These antibodies have similar stimulatory activity compared to parental mouse anti-human OX40 mAb (Mouse106-222). However, the fully humanized anti-human OX40 Ab, Hu106, did not enhance T cell proliferation. (FIG. 28)

To evaluate the ability of humanized anti-human OX40 antibodies to block CD4$^+$ regulatory T cell (Tregs) suppressive function, we performed proliferation assays using freshly sorted naïve CD4$^+$ T cells and CD4$^+$CD25$^{high}$CD127$^{low}$ Tregs. We found that the chimeric antibody Ch122 and Fc binding mutated humanized antibody (Hu122-AA) exhibited better potency than parental mouse anti-human OX40 mAb (Mouse122) in blocking CD4$^+$ Treg suppressive function. (FIG. 29 A-B)

In the experiment of FIG. 27, freshly sorted CD4$^+$CD25$^{high}$CD127$^+$CD45RO$^-$CD45RA$^+$ naïve T cells were stimulated with L cells expressing CD32 (CD32-L) coated with 4 concentrations of anti-CD3 antibodies plus 2 µg/ml of anti-human OX40 Ab clone 119 antibodies or control antibodies. Three days after stimulation, radioisotope tritium was added and cultured for additional 16-18 hrs before cell harvest. Data are a representative of experiments from two donors. CD32-L cells-expressing hOX40 ligand (CD32-L/hOX40L) serves as positive control, while human and mouse IgG1 serve as negative controls.

Figure 28:
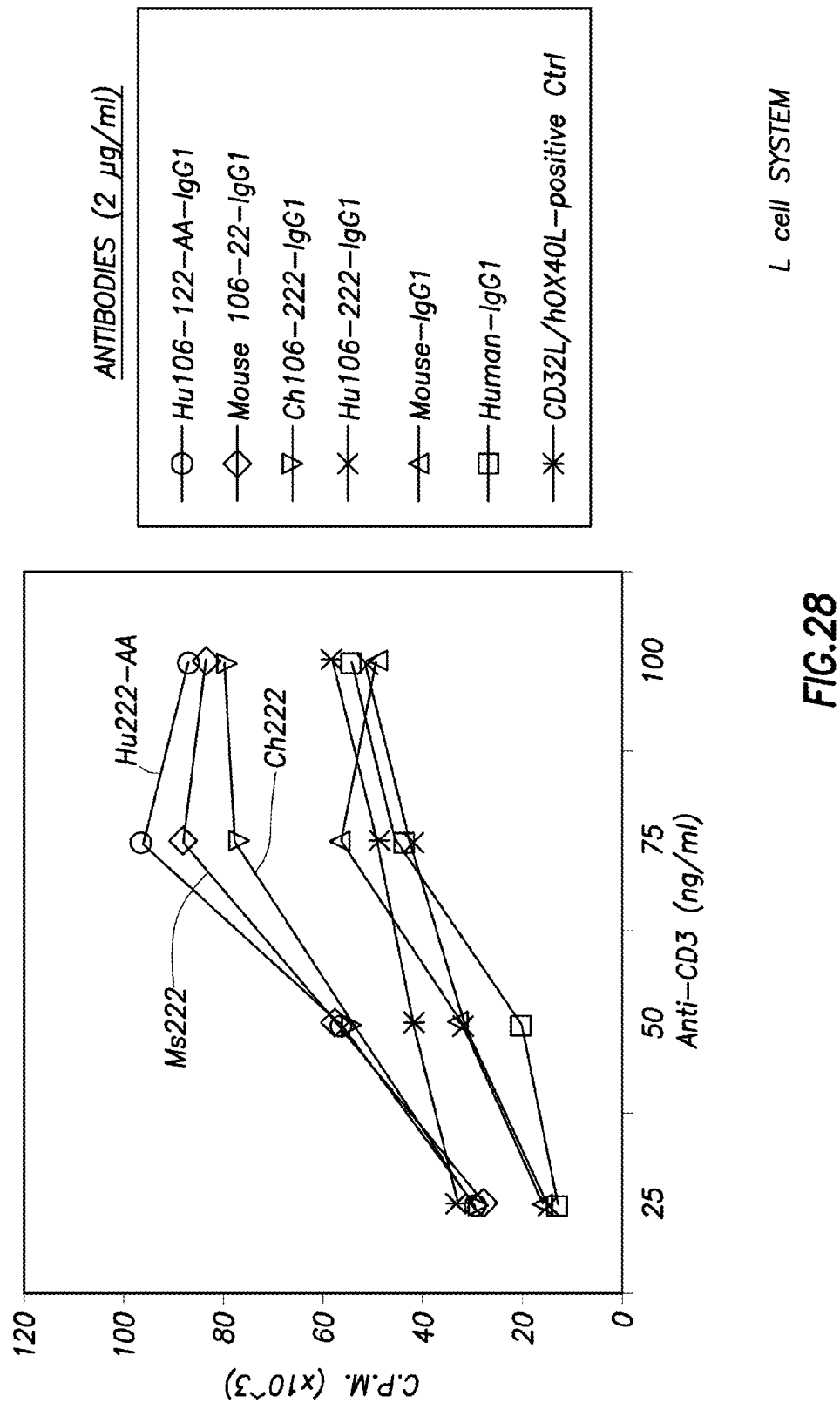
FIG. 28 shows FcR binding mutated humanized anti-human OX40 mAb clone 106-222 (Hu222AA) and chimeric anti-human OX40 mAb clone 106-222 (Ch222) enhanced anti-CD3 stimulated naïve CD4+ T cell proliferation. These antibodies have similar stimulatory activity compared to parental mouse anti-human OX40 mAb (Mouse222). However, the fully humanized anti-human OX40 Ab, Hu222, did not enhance T cell proliferation compared to human IgG1.

In the experiment of FIG. 28, freshly sorted naïve CD4$^+$ T cells were stimulated with CD32-L cells coated with 4 concentrations of anti-CD3 antibodies plus 2 µg/ml of anti-human OX40 mAb clone 106-222 (Hu222) antibodies or control antibodies. Three days after stimulation, radioisotope tritium was added and cultured for additional 16-18 hrs before cell harvest. Data are representative of experiments from two donors. CD32-L/hOX40L serves as positive control, while human and mouse IgG1 serve as negative controls.

Figure 29B:
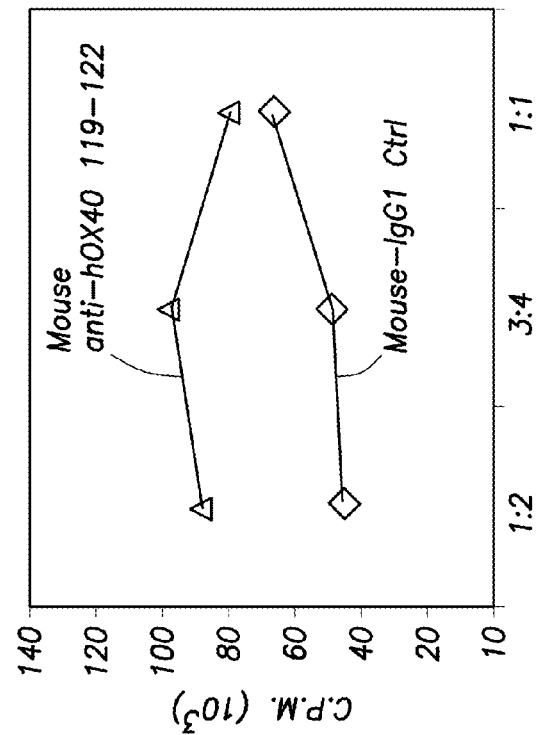
FIGS. 29A and B shows that the humanized and mouse anti-human OX40 mAb clone 119-122 blocks CD4+ Treg suppressive function.
Figure 29A:
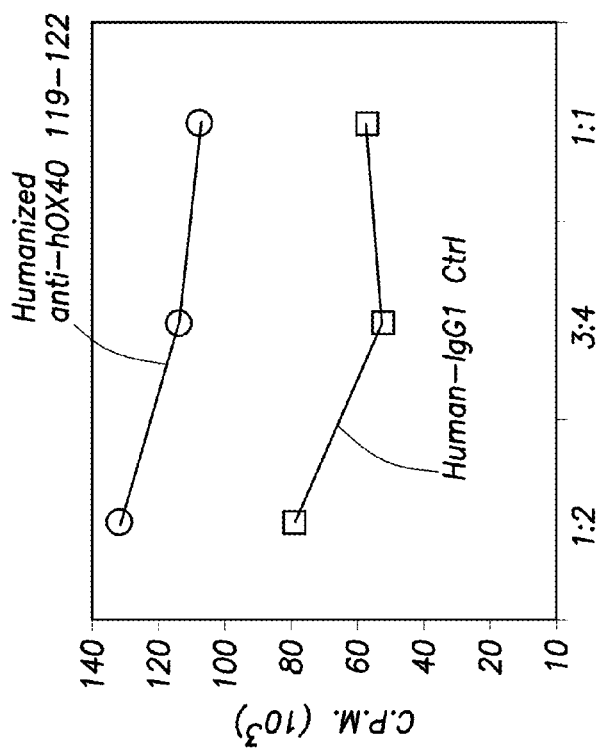

In the experiment of FIG. 29. freshly sorted CD4$^+$ naïve T cells were cultured in the presence of CD4$^+$CD25$^{high}$CD127$^{low}$Tregs at three Tregs: T effector ratios and were stimulated with CD32-L cells coated with 0.41 g/ml of anti-CD3 antibodies plus 10 µg/ml of anti-human OX40 mAb clone 119-122 antibodies or control antibodies. Three days after stimulation, radioisotope tritium was added and cultured for additional 16-18 hrs before cell harvest. Data are representative of three experiments. CD32-L/hOX40L serves as positive control, while human and mouse IgG1 serve as negative controls.

Example IV

Figure 30A:
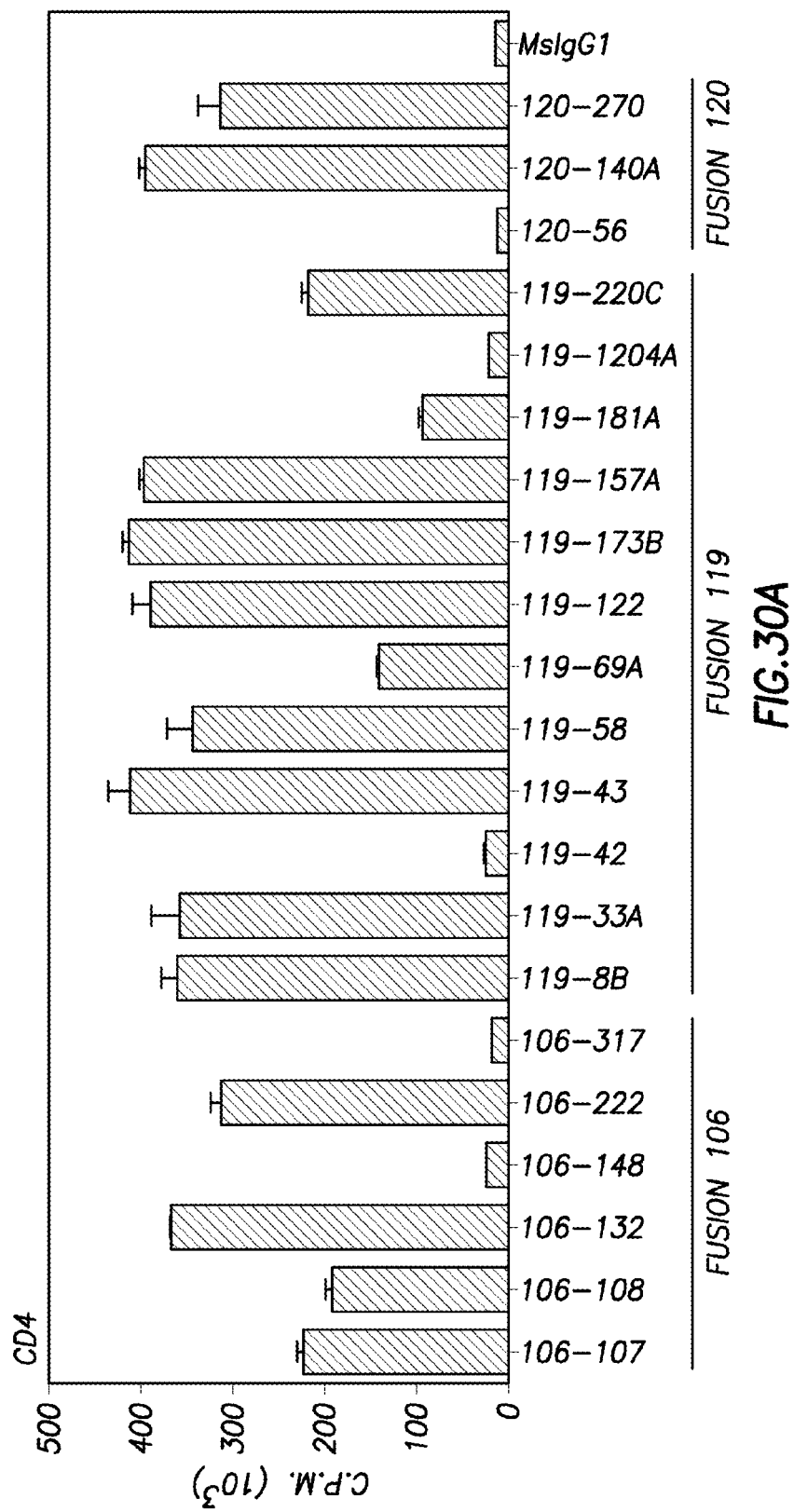
FIGS. 30A-C provide data showing anti-human OX40 antibodies enhance CD4+ and CD8+ T cell proliferation using plate-bound antibodies.

Since antibodies will encounter total peripheral blood mononuclear cells (PBMCs) when they are given to patients via intravenous injection, we tested the ability of our anti-human OX40 antibodies to stimulate T cell proliferation using PBMCs as antigen-presenting cells (APCs) in our proliferation assays. However, we obtained highly variable data with our mouse anti-human OX40 mAbs when using PBMCs as APCs that is not seen when using monocytes as APCs, suggesting that our antibodies require some kind of cross-linking for activity. To test this possibility, plates were coated with our anti-human OX40 mAbs and anti-CD3, washed, and used to stimulate CD4$^+$ or CD8$^+$ T cell proliferation in the absence of accessory cells. FIG. 30 shows the results that anti-human OX40 antibodies enhance CD4$^+$ and CD8$^+$ T cell proliferation.

Freshly sorted 1×10$^5$ of CD4$^+$CD25$^{low}$CD45RO$^-$CD45RA$^+$ naïve T cells (FIG. 30A) or CD3$^+$CD8$^+$ T cells (FIG. 30B) were stimulated with plate-bound anti-CD3 (3 µg/ml) and anti-human OX40 mouse mAb (2 µg/ml). Tritiated thymidine was added on the third day of culture and cells were harvested after another 15 hours of incubation. Proliferation of T cells was evaluated by thymidine incorporation. Anti-human OX40 mAbs were derived from three hybridoma fusions. Numbers following fusion number denote a specific antibody. Mouse IgG1 and 119-42 served as negative controls. Each treatment was performed in triplicate. Representative data from 4 T cell donors are shown. (FIG. 30C) All three versions of humanized anti-human OX40 mAbs [Hu106-222 and Hu119-122; Hu106-222AA and Hu119-122AA (AA denotes two of the Fc binding residues were mutated to the amino acid alanine); and Ch119-122 (similar to humanized 119-122 except that the mouse variable region "paratope" was maintained)] stimulated naïve CD4$^+$ T cell proliferation. Anti-CD28 served as a positive control.

Figure 30C:
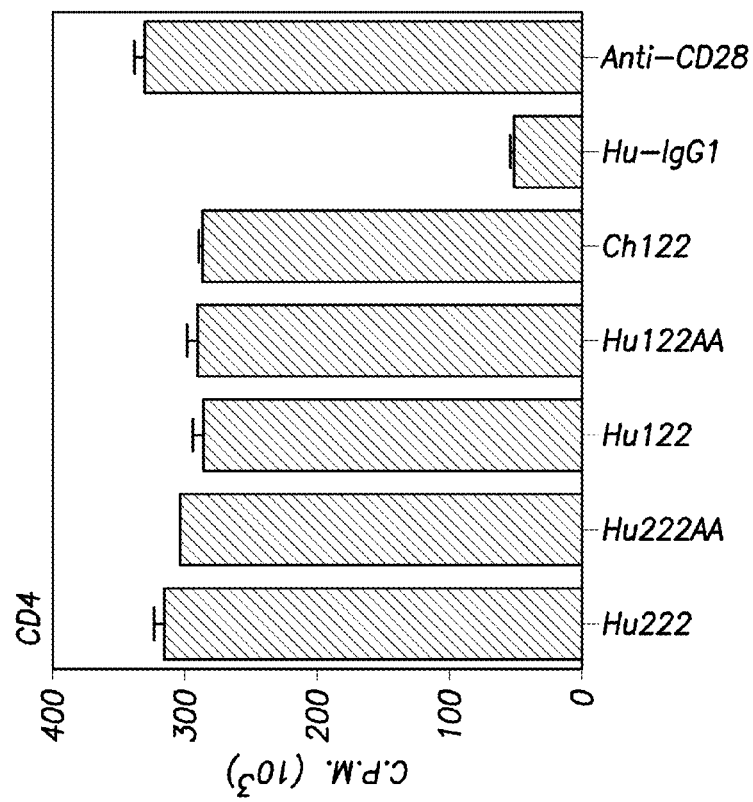
Figure 30B:
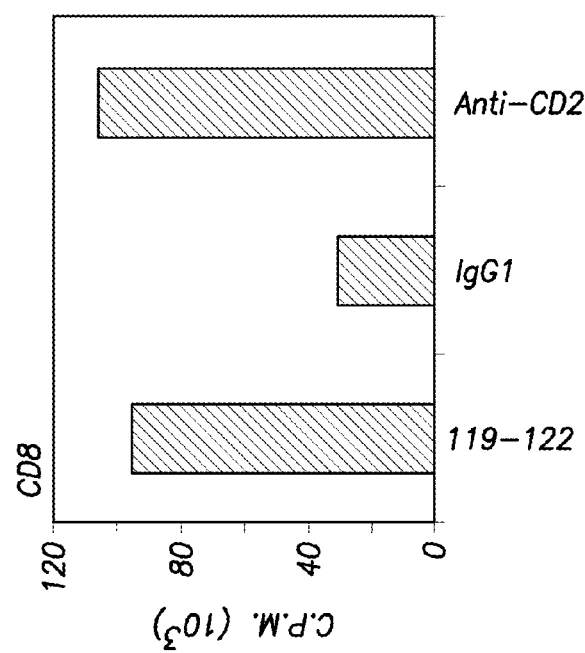

As shown in FIG. 30, panels A and B, show that plate-bound mouse anti-human OX40 mAbs potently stimulated proliferation of naive CD4$^+$ T cells and CD8$^+$ T cells by a range of 10 to 40 fold. We extended our studies to our humanized anti-human OX40 mAbs and found that the three versions of our humanized antibodies, whether it was fully humanized, chimeric or had AA mutants in which residues responsible for binding to the Fc receptor were altered to alanine, were potent stimulators of naive CD4$^+$ T cell proliferation (FIG. 30C).

FIG. 31 shows mouse and humanized anti-human OX40 antibodies require cross-linking in order to enhance T cell proliferation. Freshly sorted naïve CD4$^+$ T cells were stimulated with plate-bound anti-CD3 (3 µg/ml) plus plate-bound or soluble humanized anti-human OX40 mAbs (2 µg/ml) in the absence of accessory cells. Tritiated thymidine was added on the third day of culture and cells were harvested after another 15 hours of incubation. Proliferation of T cells was evaluated by thymidine incorporation. Mouse IgG1 and anti-CD28 served as negative and positive controls, respectively. Representative data from two donors are shown. Naïve CD4$^+$ T cells were stimulated with plate-bound anti- CD3 in the absence of accessory cells. The next day, anti-human OX40 mAb 119-122 (2 µg/ml) was added alone or in combination with equal amount of a secondary antibody against Fc. Cell proliferation was evaluated as described in panel A.

The potency of our humanized anti-human OX40 mAbs Hu106-222 and Hu119-122 was comparable to that of anti-CD28. In contrast, when soluble anti-human OX40 antibody was added to the T cell culture, the stimulatory effect was abolished. (FIG. 31A). However, when soluble anti-human OX40 mAb 119-122 was added together with a F(ab')$_2$ fragment goat anti-mouse IgG, Fc fragment specific secondary antibody, the stimulatory effect was restored (FIG. 31B). These results demonstrate that anti-human OX40 mAbs require cross-linking for their biological activities.

Figure 32C:
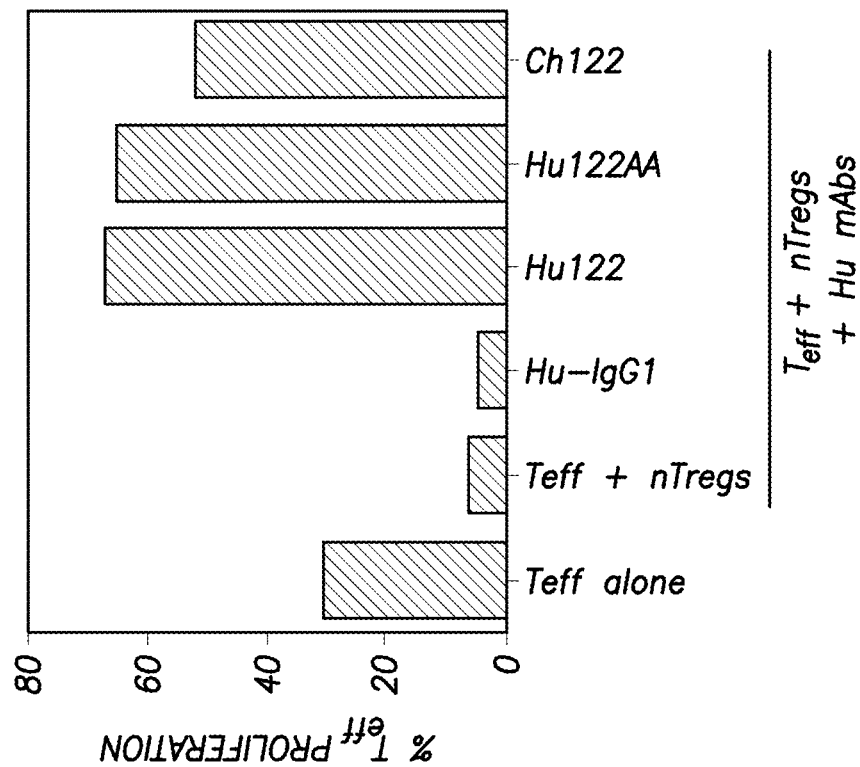
Figure 32A:
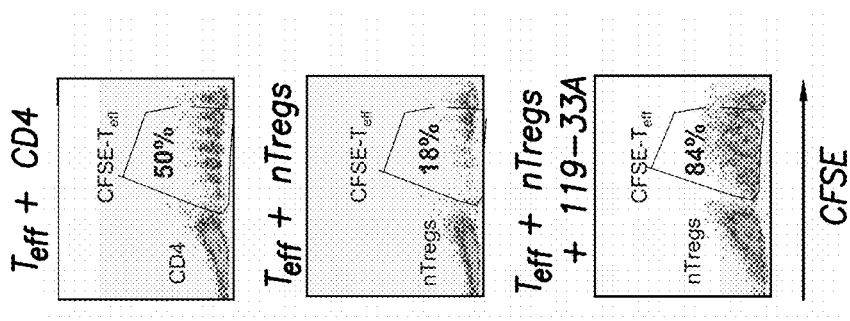

To evaluate the ability of our agonistic, anti-human OX40 mAbs to block the high suppressive function of CD4$^+$CD25 CD12T nTregs, we performed proliferation assays in the presence of CD4$^+$CD25$^{low}$CD127+CD45RO+ T effector cells (Teff) and CD4$^+$ nTregs. By using our plate-bound system in which anti-human OX40 mAbs together with anti-CD3 were coated on a plate and in the absence of accessory cells, twelve (222, 132, 8B, 33A, 43, 58B, 122, 157A, 173B, 220C, 140A, 270) of our anti-human OX40 mouse mAbs potently inhibited nTreg suppression (FIGS. 32A and 32B). Although the ratio of nTregs to T effector cell used in these assays was 1:1, these antibodies were able to stimulate T effector cells to proliferate 10 to 35 percent above the percentage achieved by T effector cells in the absence of nTregs. Our humanized anti-human OX40 mAbs also reversed the suppressive function of nTregs at similar levels (FIG. 32C). These results taken together suggest that our anti-human OX40 mouse mAbs are potent stimulators of OX40, resulting in significant enhancement of T cell proliferation and inhibition of nTreg suppressive function. Furthermore, our humanized anti-human OX40 mAbs maintained the potent biological activities of their parental mouse antibodies.

FIG. 32 shows anti-human OX20 mAb block the activity of CD4$^+$FOXP3$^+$nTregs. CFSE-labeled CD4$^+$CD25$^-$CD45RO$^+$ T effector cells and CD4$^+$FOXP3$^+$Tregs were derived from the same healthy donor. T cells were stimulated with soluble anti-CD28 (0.5 µg/ml) and plate-bound anti-CD3 (3 µg/ml) and anti-human OX40 mAbs (2 µg/ml). Proliferation of T effector cells was evaluated by flow cytometry for CFSE dilution. The ratio of nTregs to T effector cells was 1:1. Mouse IgG1 served as negative control. Naïve CD4$^+$ T cells served as control T cells to demonstrate specific inhibition of T effector cell proliferation by nTregs. FIG. 32A is a representative FACS data showing the proliferation of T effector cells in the presence of naïve CD4$^+$ T cells, nTregs or nTregs plus the anti-human OX40 mAb 119-33A. FIG. 32B shows the percentage of T effector cell proliferation in the presence of nTregs after treatment with a mouse anti-human OX40 mAb (20 tested). FIG. 32C shows all three versions of humanized anti-human OX40 mAbs restored proliferation of T effector cells.

A recent report suggests that OX40 triggering can induce apoptosis of a human T cell line expressing OX40 (Yoshiaki Takahashi et al., 200B, Aids Research and human Retroviruses, 24). We therefore tested the effect of increasing concentrations of the anti-human OX40 mAb 106-222 plus a fixed, low dose of anti-CD3 on the survival of three T cell subsets in the presence of monocytes. FIG. 33A shows that high concentrations of anti-human OX40 mAb 106-222 (20-30 µg/ml) preferentially killed activated FOXP3$^+$ nTregs while activated naïve and memory CD4$^+$ T cells were either resistant or less susceptible to this effort. To test whether the anti-human OX40 mAb acts directly on Tregs to induce cell death, we performed new experiments in the absence of accessory cells. FIG. 33B shows that strong OX40 signaling in combination with anti-CD3 specifically killed nTregs in the absence of accessory cells. To confirm if the killing effects mediated by anti-human OX40 mAb mimicked OX40 triggering by natural OX40 ligand, we used a mouse fibroblast L cell line that over-expressed hOX40L and used it to stimulate nTregs in the presence of a low dose of anti-CD3 and obtained similar killing effects on nTregs (FIG. 33C). These results suggest that strong OX40 triggering kills OX40-expressing Tregs cells.

Specifically, FIG. 33 shows high concentration of anti-human OX40 mAb preferentially kills FOXP3$^+$ Tregs. In FIG. 33A, T cell subsets (naïve, CD4$^+$CD25$^{low}$CD127$^+$ CD45RO$^-$CD45RA$^+$; memory, CD4$^+$CD25$^{low}$CD127$^+$ CD45RA$^-$CD45RO$^+$; and nTregs, CD4$^+$ CD25$^{high}$CD127$^{low}$) were each cultured with an equal ratio of CD14$^+$ monocytes in the presence of soluble anti-CD3 (0.3 µg/ml) and increasing concentrations of the mouse anti-human OX40 mAb 106-222. Cell viability was determined after 3 days of culture by flow cytometry analysis, gating on viable lymphocytes. Data from two T cell donors are shown. FIGS. 33B and 33C show strong triggering of OX40 kills CD4$^+$FOXP3$^+$ Tregs. FIG. 33B shows that CD4$^+$FOXP3$^+$ Tregs were stimulated with plate-bound anti-CD3 (2 µg/ml) plus soluble 119-122 mAb (30 µg per million cells) or mouse IgG1 control antibody. Trypan blue-negative live cells after one day of culture were counted with a hemacytometer. FIG. 33C shows that CD4$^+$FOXP3$^+$ Tregs were stimulated with soluble anti-CD3 (0.2 µg/ml) plus L cells or L cells expressing the hOX40 ligand (L/hOX40L). Live cells were counted after one day of stimulation.

We next sought to determine whether anti-human OX40 mAb acts directly on T cells to block nTreg suppressive function. Freshly sorted CD4+T effector cells or nTregs were preactivated overnight with anti-CD3 and then pulsed with anti-human OX40 mAbs for 4 hours. T effectors cells were then washed, labeled with CFSE, and co-cultured with nTregs in the presence of an equal number of CD14$^+$ monocytes and anti-CD3. Similarly, the pre-stimulated nTregs were washed and cultured with untreated CFSE-Labeled T effector cells.

Figure 34A:
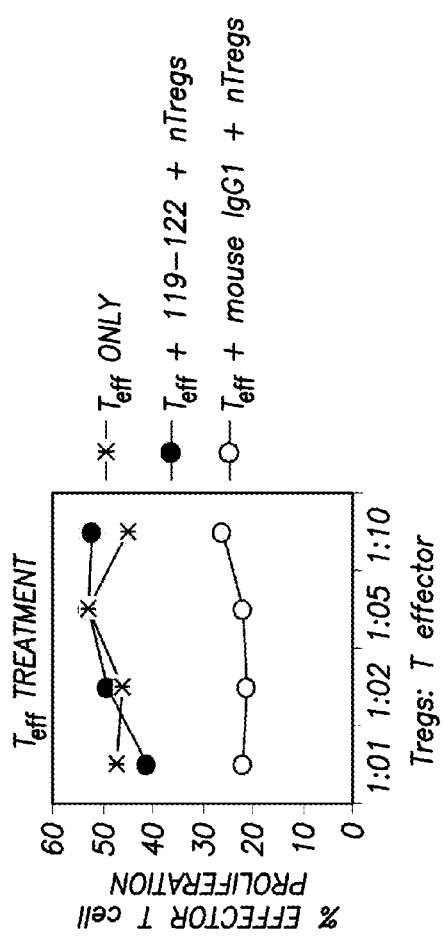
FIGS. 34A-B show mouse anti-human OX40 mAbs act directly on either effector T cells or nTregs to block the suppressive function of Tregs.
Figure 34B:
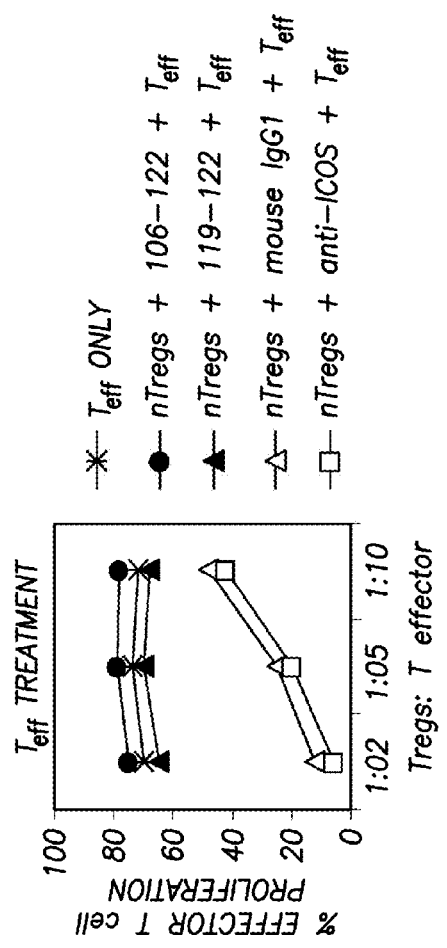

FIG. 34 shows anti-human OX40 mAbs act directly on T cells to block the suppressive function of Tregs. FIG. 34A shows anti-human OX40 mAb acts directly on effector memory T cells to confer them resistant to suppression by nTregs. CD4$^+$ CD25$^{low}$CD127$^+$CD45RA$^-$ CD45RO$^+$ memory T cells were stimulated with plate-bound anti-CD3 (0.8 µg/ml) in culture medium (RPMI/10% FCS/P/S plus IL-2 at 30 IU/ml) for 12 hours, then pulsed with anti-human OX40 mAb (119-122, 22 µg per 0.5 million cells) in culture medium for 4 hours, washed 3 times, and 8×10$^4$ of CFSE-labeled effector T cells were cultured with decreasing ratios of nTregs. Proliferation of effector T cells was evaluated by flow cytometry for CFSE dilution. Anti-human OX40 mAb acts on Tregs making them unable to suppress T effector cell proliferation (FIG. 34B). CD4$^+$CD25$^{high}$CD127$^{low}$ nTregs were pre-stimulated with plate-bound anti-CD3 (2 µg/ml) in culture medium for 12 hours, then pulsed with an anti-human OX40 mAb, 119-122 or 106-222, or a control antibody, anti-ICOS or mouse IgG1, as described in panel A, washed and cultured with CFSE-labeled T effector memory cells. Proliferation of T effector cells was evaluated by flow cytometry for CFSE dilution.

T effector cells treated with anti-human OX40 mAb became resistant to suppression by nTreg cells. (FIG. 34A) By contrast, proliferation of T effector cells treated with mouse IgG1 control antibody remained susceptible to suppression by nTregs. FIG. 34B shows that nTregs treated with anti-human OX40 mAbs were unable to suppress proliferation of T effector cells. By contrast, nTregs treated with control antibodies, such as anti-I COS or mouse IgG1, remained suppressive. These results suggest that our anti-human OX40 mAbs act directly on both T effector cells and nTregs to restore T effector cell proliferation.

Example V

Supplemental preliminary in vivo data showed that anti-human OX40 antibody works in mice enhances T cell expansion and tumor rejection in mice. It was previously shown that anti-human OX40 mAb can specifically activate the NF-κB cascade in mouse CD8$^+$ T cells transduced with human OX40. To determine whether the anti-hOX40 mAb can enhance tumor rejection by promoting effector CD8$^+$ T cell survival and clonal expansion in vivo, transgenic Pmel CD8$^+$ T cells transduced with the luciferase gene and hOX40 were adaptively transferred into C57BL/6 albino mice bearing non-pigmented MC38 tumors. After adoptive transfer of the transduced T cells, mice were treated with Abs. It was found that significantly more human OX40$^+$ luciferase$^+$ Pmel T cells migrated into the lung on day 4 in mice treated with anti-hOX40 mAb compared with mouse treated with IgG1 control antibody (FIG. 35B), indicating that hOX40 triggering in mice promoted CD8$^+$ T cell expansion. Upon day 8 (data not shown) and day 12 after treatment, it was found that the same group of mice treated with anti-hOX40 mAb retained significantly more luciferase$^+$Pmel T cells at the tumor site compared with the control group of mice treated with IgG1 (FIG. 35B), again indicating that hOX40 triggering in mice promoted CD8$^+$ T cell survival. Finally, tumor sizes of mice that received hOX40$^+$Pmel CD8$^+$ T cells and subsequently treated with anti-hOX40 mAb were significantly smaller compared with those of mice that received nontransduced Pmel T cells and treated with anti-hOX40 mAb or hOX40$^+$Pmel T cells followed by treatment with control mouse IgG1-match antibody. These results show that the triggering of human OX40 in mice results in biological effects similar to those of mouse OX40 (Gough M J et, 2008). Therefore, the data demonstrates the ability of anti-human OX40 mAb to stimulate CD$^+$T cell expansion and survival in vivo and enhance tumor rejection.

Anti-Human OX40 mAb Promotes T Cell Expansion and Survival In Vivo.

Figure 35C:
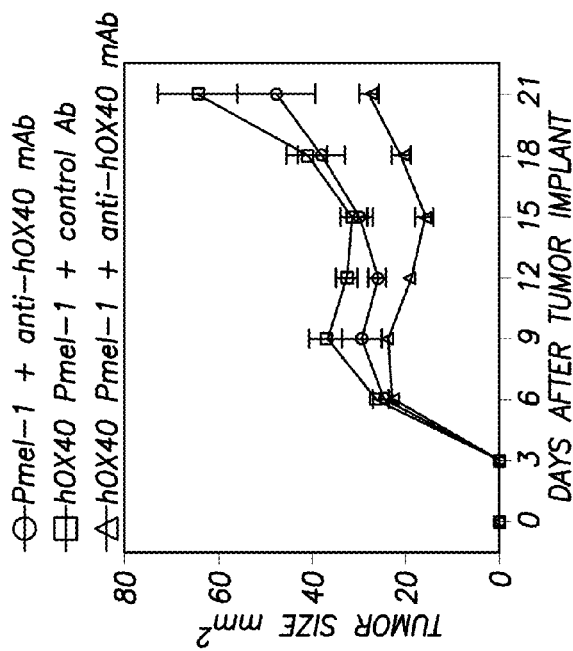
FIGS. 35A, 35B, and 35C show the results of anti-hOX40 mAb tumor treatment in mice adaptively transferred with hOX40+CD8+ T cells. The anti-human OX40 mAb promotes T cell expansion and survival in vivo. The therapeutic vaccination regimen is shown in FIG. 35A. Representative in vivo bioluminescence images are shown in FIG. 35B. Results of the antibody tumor treatment are shown in FIG. 35C.
Figure 35A:
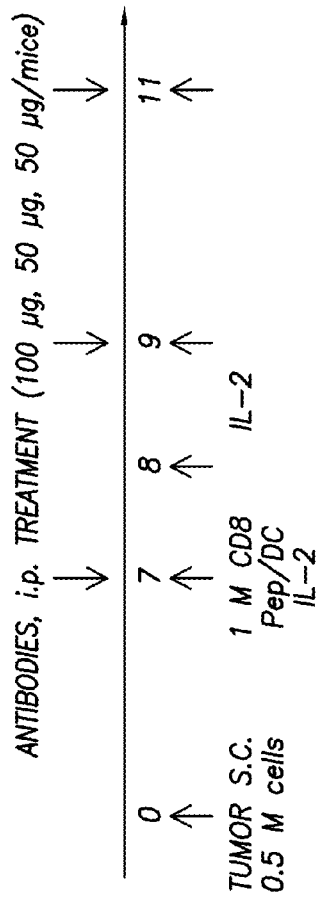
Figure 35B:
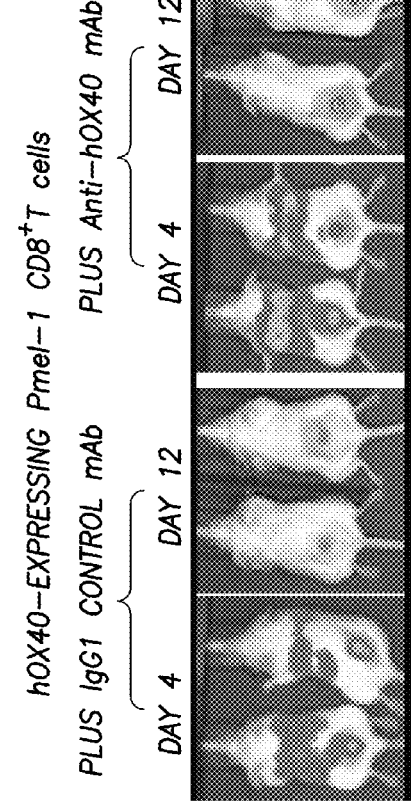

Our therapeutic vaccination regimen is shown in FIG. 35A. C57BL/6 albino mice in groups of 5 were subcutaneously (S.C) implanted with 5×10$^5$ non-pigmented MC38/gp100 tumor cells (day 0). On day 6, lymphopenia was induced by administering a 350 cGy dose of radiation. On day 7, 1×10$^6$ luciferase transduced Pmel-1 T cells with or without human OX40 expression were adoptively transferred into tumor-bearing mice (n=5 per group), followed by intravenous injection of 5×10$^5$ Gp100 peptide-pulsed DCs. Recombinant human IL-2 was intraperitoneally administered for 3 d after T cell transfer. Antibodies were administered on days 7, 9 and 11 with 100, 50 and 50 μg, respectively, per injection per mouse (FIG. 35B). In vivo bioluminescence images showed accumulation of luciferase-expressing CD8$^+$ pmel-1 T cells in the lung and tumor sites on days 4 and 12. Two of five mice per group on day 4 and day 12 are shown (FIG. 35C). Tumors responded to treatments using anti-hOX40 mAb. Tumor size was measured every 3 days. Pmel-1 and Pmel-1 plus mouse IgG1 served as controls.

We claim:

1. An isolated antibody or antigen-binding portion thereof which binds to and agonizes OX40 comprising:
   (a) a heavy chain variable region CDR1 comprising the amino acid sequence of SEQ ID NO:13;
   (b) a heavy chain variable region CDR2 comprising the amino acid sequence of SEQ ID NO:14;
   (c) a heavy chain variable region CDR3 comprising the amino acid sequence of SEQ ID NO:15;
   (d) a light chain variable region CDR1 comprising the amino acid sequence of SEQ ID NO:19;
   (e) a light chain variable region CDR2 comprising the amino acid sequence of SEQ ID NO:20;
   and (f) a light chain variable region CDR3 comprising the amino acid sequence of SEQ ID NO:21.

2. An isolated antibody or antigen-binding portion thereof according to claim 1, wherein the isolated antibody comprises a light chain variable region having a sequence at least 90% identical to the amino acid sequence of SEQ ID NO:22 and a heavy chain variable region having a sequence at least 90% identical to the amino acid sequence of SEQ ID NO:16.

3. The isolated antibody or antigen-binding portion thereof of claim 2, wherein the isolated antibody comprises a light chain variable region having the amino acid sequence of SEQ ID NO:22 and a heavy chain variable region having the amino acid sequence of SEQ ID NO:16.

4. The isolated antibody or antigen-binding portion thereof of claim 1, comprising a light chain variable region having a sequence at least 90% identical to the amino acid sequence of SEQ ID NO:23 and a heavy chain variable region having a sequence at least 90% identical to the amino acid sequence of SEQ ID NO:17.

5. The isolated of antibody or antigen-binding portion thereof of claim 4, comprising a light chain variable region having the amino acid sequence of SEQ ID NO:23 and a heavy chain variable region having the amino acid sequence of SEQ ID NO:17.

6. An isolated antibody or antigen-binding portion thereof of claim 1, wherein the isolated antibody is a monoclonal antibody.

7. The isolated antibody or antigen-binding portion thereof of claim 6, wherein the isolated monoclonal antibody is a humanized antibody.

8. An antigen-binding portion of an antibody according to claim 1, wherein the antigen-binding portion retains the ability to specifically bind and agonize OX40 receptor.

9. A pharmaceutical composition comprising the antibody or antigen-binding portion thereof of claim 1.

* * * * *

UNITED STATES PATENT AND TRADEMARK OFFICE
CERTIFICATE OF CORRECTION

PATENT NO. : 9,695,246 B2  Page 1 of 1
APPLICATION NO. : 14/684550
DATED : July 4, 2017
INVENTOR(S) : Liu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 270 days.

Signed and Sealed this
Twenty-fifth Day of September, 2018

Andrei Iancu
*Director of the United States Patent and Trademark Office*